United States Patent
Christopher et al.

(10) Patent No.: US 11,696,926 B2
(45) Date of Patent: Jul. 11, 2023

(54) METHODS AND COMPOSITIONS FOR TREATMENT OF CANCER

(71) Applicants: Matthew Christopher, St. Louis, MO (US); John F. DiPersio, St. Louis, MO (US); Timothy J. Ley, St. Louis, MO (US); Allegra Petti, St. Louis, MO (US); Michael P. Rettig, St. Louis, MO (US)

(72) Inventors: Matthew Christopher, St. Louis, MO (US); John F. DiPersio, St. Louis, MO (US); Timothy J. Ley, St. Louis, MO (US); Allegra Petti, St. Louis, MO (US); Michael P. Rettig, St. Louis, MO (US)

(73) Assignee: Washington University, St. Louis, MO (US)

( * ) Notice: Subject to any disclaimer, the term of this patent is extended or adjusted under 35 U.S.C. 154(b) by 454 days.

(21) Appl. No.: 16/774,425

(22) Filed: Jan. 28, 2020

(65) Prior Publication Data
US 2020/0237817 A1 Jul. 30, 2020

Related U.S. Application Data

(60) Provisional application No. 62/798,630, filed on Jan. 30, 2019.

(51) Int. Cl.
*A61K 35/14* (2015.01)
*A61P 35/02* (2006.01)
*C12N 5/0783* (2010.01)
*A61K 38/21* (2006.01)

(52) U.S. Cl.
CPC ............ *A61K 35/14* (2013.01); *A61K 38/217* (2013.01); *A61P 35/02* (2018.01); *C12N 5/0636* (2013.01)

(58) Field of Classification Search
CPC ...... A61K 35/14; A61K 38/217; A61K 35/17; A61K 35/28; A61P 35/02; C12N 5/0636
See application file for complete search history.

(56) References Cited

PUBLICATIONS

Christopher et al, New Eng J Med 379: 24, online published Oct. 31, 2018 (Year: 2018).*
Christopher et al, Blood 130(supple_1: 2678, abstract No. 617, Dec. 2017 (Year: 2017).*
Matte-Martone et al, J Clin Invest, 127: 2765, 2017. (Year: 2017).*
Albring JG, Inselmann S, Sauer T, et al. PD-1 checkpoint blockade in patients with relapsed AML after allogeneic stem cell transplantation. Bone Marrow Transplant 2017;52:317-20.
Anagnostou V, Smith KN, Forde PM, et al. Evolution of Neoantigen Landscape during Immune Checkpoint Blockade in Non-Small Cell Lung Cancer. Cancer Discov 2017;7:264-76.
Anderson DA, 3rd, Grajales-Reyes GE, Satpathy AT, Hueichucura CEV, Murphy TL, Murphy KM. Revisiting the specificity of the MHC class II transactivator CIITA in classical murine dendritic cells in vivo. Eur J Immunol 2017.
Bacher U, Haferlach T, Alpermann T, et al. Comparison of cytogenic clonal evolution patterns following allogeneic hematopoietic transplantation versus conventional treatment in patients at relapse of AML. Biol Blood Marrow Transplant 2010;16:1649-57.
Bray NL, Pimentel H, Melsted P, Pachter L. Near-optimal probabilistic RNA-seq quantification. Nat Biotechnol 2016;34:525-7.
Chen J, Bardes EE, Aronow BJ, Jegga AG. ToppGene Suite for gene list enrichment analysis and candidate gene prioritization. Nucleic Acids Res 2009;37:W305-11.
Christopher MJ, Petti AA, Rettig MP, et al. Immune Escape of Relapsed AML Cells after Allogeneic Transplantation. N Engl J Med 2018, 379(24):2230-2341.
Della Porta MG, Galli A, Bacigalupo A, et al. Clinical the outcomes of patients with myelodysplastic syndr hematopoietic stem-cell transplantation. J Clin Oncol 2015;34:3627-37.
Dermime S, Mavroudis D, Jiang YZ, Hensel N, Molldrem J, Barrett AL. Immune escape from a graft-versus-leukemia effect may play a role in the relapse of myeloid leukemias following allogeneic bone marrow transplantation. Bone Marrow Transplant 1997;19:989-99.
Dickinson AM, Norden J, Li S, et al. Graft-versus-leukemia effect following hematopoietic stem cell transplantation for leukemia. Front Immunol 2017;8:496.
Ding L, Ley TJ, Larson DE, et al. Clonal evolution in relapsed acute myeloid leukaemia revealed by whole-genome sequencing. Nature 2012; 481: 506-10.
Dunn GP, Bruce AT, Ikeda H, Old LJ, Schreiber RD. Cancer immunoediting: from immunosurveillance to tumor escape. Nat Immunol 2002;3:991-8.
Farrar JE, Schuback HL, Ries RE, et al. Genomic profiling of pediatric acute myeioid leukemia reveals a changing mutational landscape from disease diagnosis to relapse. Cancer Res 2016;76:2197-205.
Griffith M, Miller CA, Griffith OL, et al. Optimizing cancer genome sequencing and analysis. Cell Syst 2015;1:210-23.
Hamdi A, Cao K, Poon LM, et al. Are changes in HLA Ags responsible for leukemia relapse after HLA-matched allogeneic hematopoietic SCT? Bone Marrow Transplant 2015;50:411-3.
Harris AC, Kitko CL, Couriel DR, et al. Extramedullary relapse of acute myeloid leukemia following allogeneic hematopoietic stem cell transplantation: incidence, risk factors and outcomes, Haematologica 2013;98:179-84.
Hirsch P, Zhang Y, Tang R, et al. Genetic hierarchy and temporal variegation in the clonal history of acute myeloid leukaemia. Nat Commun 2016;7:12475.

(Continued)

Primary Examiner — Lei Yao

(57) ABSTRACT

Among the various aspects of the present disclosure is the provision of methods and compositions for upregulating MHC class II in cancer cells (e.g., a hematological cancer cell). Also provided are methods of treatment for subjects suffering from hematological cancers, comprising administration of interferon-γ (IFN-γ). The methods of treatment provided herein may be particularly suitable for subjects who have received an allogenic transplant or have suffered a relapse.

9 Claims, 32 Drawing Sheets

(56) References Cited

PUBLICATIONS

Hundal J, Carreno BM, Petti AA, et al. pVAC-Seq: A genome-guided in silico approach to identifying tumor neoantigens. Genome Med 2016;8:11.

Juhling F, Kretzmer H, Bernhart SH, Otto C, Stadler PF, Hoffmann S. metilene: fast and sensitive calling of differentially methylated regions from bisulfite sequencing data. Genome Res 2016;26:256-62.

Klco JM, Miller CA, Griffith M, et al. Association between mutation clearance after induction therapy and outcomes in acute myeloid leukemia. JAMA 2015;314: 811-22.

Klco JM, Spencer DH, Lamprecht TL, et al. Genomic impact of transient low-dose decitabine treatment on primary AML cells. Blood 2013;121:1633-43.

Klco JM, Spencer DH, Miller CA, et al. Functional heterogeneity of genetically defined subclones in acute myeloid leukemia. Cancer Cell 2014;25:379-92.

Koboldt DC, Zhang Q, Larson DE, et al. VarScan 2: somatic mutation and copy number alteration discovery in cancer by exome sequencing. Genome Res 2012;22:568-76.

Krönke J, Bullinger L, Teleanu V, et al. Clonal evolution in relapsed NPM1-mutated acute myeloid leukemia. Blood 2013; 122:100-8.

Larson DE, Harris CC, Chen K, et al. SomaticSniper: identification of somatic point mutations in whole genome sequencing data. Bioinformatics 2012;28:311-7.

Li H, Durbin R. Fast and accurate short read alignment with Burrows-Wheeler transform. Bioinformatics 2009;25:1754-60.

Li H, Handsaker B, Wysoker A, et al. The Sequence Alignment/Map format and SAMtools. Bioinformatics 2009;25:2078-9.

Luskin MR, Carroil M, Lieberman D, et al. Clinical utility of next-generation sequencing for oncogenic mutations in patients with acute myeloid leukemia undergoing allogeneic stem cell transplantation. Biol Blood Marrow Transplant 2016; 22:1961-7.

Manguso RT, Pope HW, Zimmer MD, et al. In vivo CRISPR screening identifies Ptpn2 as a cancer immunotherapy target. Nature 2017;547:413-8.

Masuda K, Hiraki A, Fujii N, et al. Loss or down-regulation of HLA class I expression at the allelic level in freshly isolated leukemic blasts. Cancer Sci 2007; 98:102-8.

Matsushita H, Vesely MD, Koboldt DC, et al. Cancer exome analysis reveals a T-cell-dependent mechanism of cancer immunoediting. Nature 2012;482:400-4.

McKenna A, Hanna M, Banks E, et al. The Genome Analysis Toolkit: a MapReduce framework for analyzing next-generation DNA sequencing data. Genome Res 2010;20:1297-303.

Mielcarek M, Storer BE, Flowers MED, Storb R, Sandmaier BM, Martin PJ. Outcomes among patients with recurrent high-risk hematologic malignancies after allogeneic hematopoietic cell transplantation. Biol Blood Marrow Transplant 2007;13:1160-8.

Morimoto Y, Toyota M, Satoh A, et al. Inactivation of class II transactivator by DNA methylation and histone deacetylation associated with absence of HLA-DR induction by interferon-gamma in haematopoietic tumour cells. Br J Cancer 2004;90:844-52.

Pollyea DA, Artz AS, Stock W, et al. Outcomes of patients with AML and MDS who relapse or progress after reduced intensity allogeneic hematopoietic cell transplantation. Bone Marrow Transplant 2007; 40:1027-32.

Quek L, Ferguson P, Metzner M, et al. Mutational analysis of disease relapse in patients allografted for acute myeloid leukemia. Blood Adv 2016;1:193-204.

Robinson MD, McCarthy DJ, Smyth GK. edgeR: a Bioconductor package for differential expression analysis of digital gene expression data. Bioinformatics 2010;26:139-40.

Robinson MD, Oshlack A. A scaling normalization method for differential expression analysis of RNA-seq data. Genome Biol 2010;11:R25.

Roemer MG, Advani RH, Ligon AH, et al. PD-L1 and PD-L2 genetic alterations define classical Hodgkin lymphoma and predict outcome. J Clin Oncol 2016;34: 2690-7.

Saunders CT, Wong WS, Swamy S, Becq J, Murray LJ, Cheetham RK. Strelka: accurate somatic small-variant calling from sequenced tumor-normal sample pairs. Bioinformatics 2012;28:1811-7.

Schmidt-Hieber M, Blau IW, Richter G, et al. Cytogenetic studies in acute leukemia patients relapsing after allogeneic stem cell transplantation. Cancer Genet Cytogenet 2010; 198:135-43.

Sehn JK, Spencer DH, Pfeifer JD, et al. Occult Specimen Contamination in Routine Clinical Next-Generation Sequencing Testing. Am J Clin Pathol 2015;144:667-74.

Shimizu H, Saitoh T, Hatsumi N, et al. Prevalence of extramedullary relapses is higher after allogeneic stem cell transplantation than after chemotherapy in adult patients with acute myeloid leukemia. Leuk Res 2013;37:1477-81.

Simpson DR, Nevill TJ, Shepherd JD, et al. High incidence of extramedullary relapse of AML after busulfan/cyclophosphamide conditioning and allogeneic stem cell transplantation. Bone Marrow Transplant 1998;22:259-64.

Soneson C, Love MI, Robinson MD. Differential analyses for RNA-seq: transcript-level estimates improve gene-level inferences. F1000Res 2015;4:1521.

Sood R, Hansen NF, Donovan FX, et al. Somatic mutational landscape of AML with inv(16) or t(8;21) identifies patterns of clonal evolution in relapse leukemia. Leukemia 2016;30:501-4.

Steidl C, Shah SP, Woolcock BW, et al. MHC class II transactivator CIITA is a recurrent gene fusion partner in lymphoid cancers. Nature 2011;471:377-81.

Stölzel F, Hackmann K, Kuithan F, et al. Clonal Evolution Including Partial Loss of Human Leukocyte Antigen Genes Favoring Extramedullary Acute Myeloid Leukemia Relapse After Matched Related Allogeneic Hematopoietic Stem Cell Transplantation. Transplantation 2012;93:744-9.

Ting JP, Trowsdale J. Genetic control of MHC class II expression. Cell 2002;109 Suppl:S21-33.

Vago L, Perna SK, Zanussi M, et al. Loss of mismatched HLA in leukemia after stem-cell transplantation. N Engl J Med 2009;361:478-88.

Van der Maaten L, Hinton G. Visualizing data using t-SNE. J Mach Learn Res 2008;9:2579-605.

Vollmer M, Li L, Schmitt A, et al. Expression of human leucocyte antigens and co-stimulatory molecules on blasts of patients with acute myeloid leukaemia. Br J Haematol 2003;120:1000-8.

Waterhouse M, Pfeifer D, Pantic M, Emmerich F, Bertz H, Finke J. Genome-wide profiling in AML patients relapsing after allogeneic hematopoietic cell transplantation. Biol Blood Marrow Transplant 2011; 17:1450-9.

Weiden PL, Flournoy N, Thomas ED, et al. Antileukemic effect of graft-versus-host disease in human recipients of allogeneic-marrow grafts. N Engl J Med 1979; 300:1068-73.

Weiden PL, Sullivan KM, Flournoy N, Storb R, Thomas ED, Seattle Marrow Transplant Team. Antileukemic effect of chronic graft-versus-host disease—contribution to improved survival after allogeneic marrow transplantation. N Engl J Med 1981;304:1529-33.

Wen H, Li Y, Malek SN, et al. New fusion transcripts identified in normal karyotype acute myeloid leukemia. PLoS One 2012;7(12):e51203.

Xi Y, Li W. BSMAP: whole genome bisulfite sequence MAPping program. BMC Bioinformatics 2009; 10:232.

Ye K, Schulz MH, Long Q, Apweiler R, Ning Z. Pindel: a pattern growth approach to detect break points of large deletions and medium sized insertions from paired-end short reads. Bioinformatics 2009;25:2865-71.

Yunis JJ, Band H, Bonneville F, Yunis EJ. Differential expression of MHC class II antigens in myelomonocytic leukemia cell lines. Blood 1989;73:931-7.

(56) References Cited

PUBLICATIONS

Zaretsky JM, Garcia-Diaz A, Shin DS, et al. Mutations associated with acquired resistance to PD-1 blockade in melanoma. N Engl J Med 2016;375:819-29.
Zheng GX, Terry JM, Belgrader P, et al. Massively parallel digital transcriptional profiling of single cells. Nat Commun 2017;8:14049.

* cited by examiner

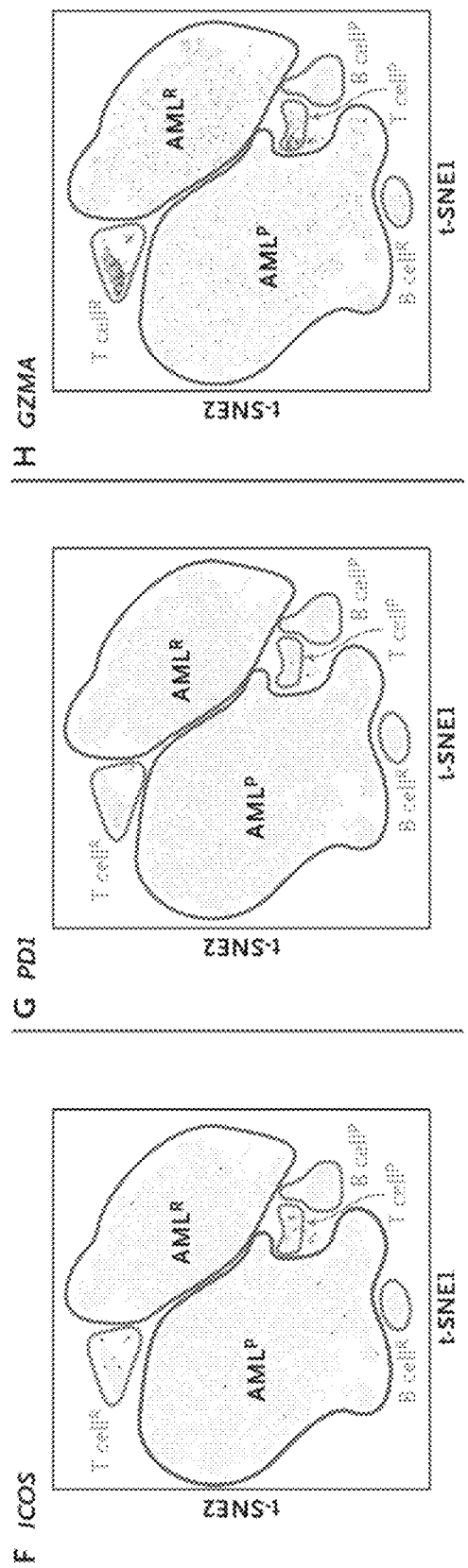

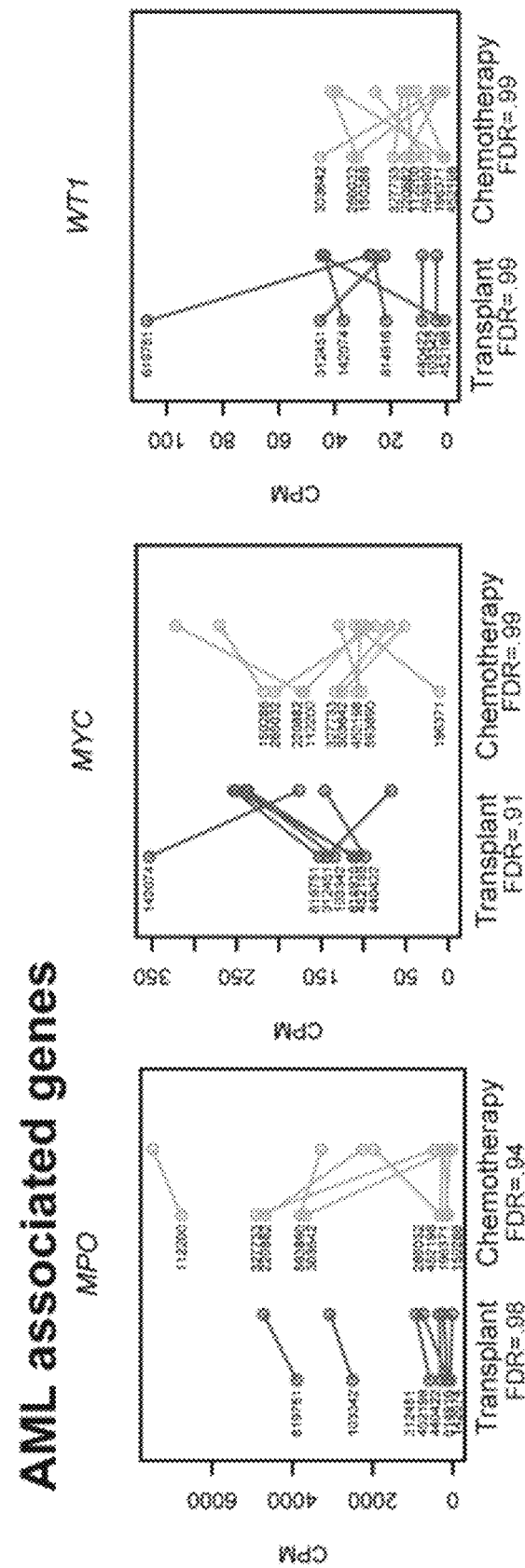

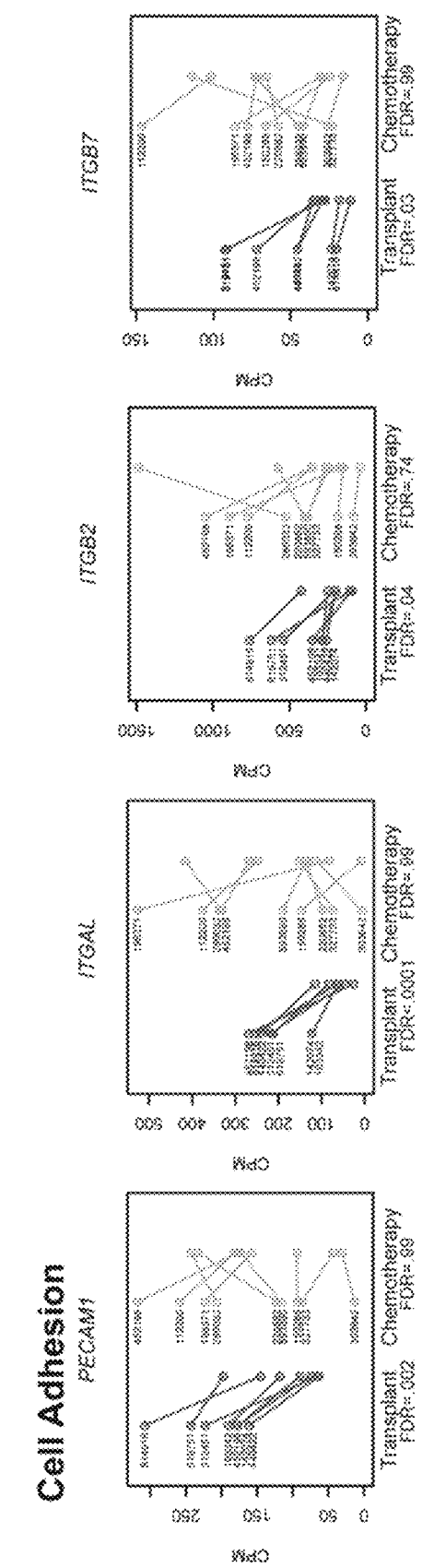

FIG. 11A

| UPN | Diagnosis HLA-DR positive blasts | 1st Relapse HLA-DR positive blasts | 2nd Relapse HLA-DR positive blasts | HLA-DR DOWNREGULATED |
|---|---|---|---|---|
| EXT 1 | <5% | 5-10% | NA | |
| EXT 2 | <5% | 5-10% | NA | |
| EXT 3 | <5% | 10-20% | NA | |
| EXT 4 | >50% | <5% | NA | yes |
| EXT 5 | 20-30% | <5% | NA | yes |
| EXT 6 | 20-30% | 20-30% | NA | |
| EXT 7 | 20-30% | <5% | NA | yes |
| EXT 8 | 20-30% | <5% | NA | yes |
| EXT 9 | 30-40% | <5% | NA | yes |
| EXT 10 | 30-40% | 30-40% | NA | |
| EXT 11 | 30-40% | 5-10% | NA | yes |
| EXT 12 | 30-40% | <5% | NA | yes |
| EXT 13 | 5-10% | >50% | NA | |
| EXT 14 | 5-10% | <5% | NA | |
| EXT 15 | 5-10% | 10-20% | NA | |
| EXT 16 | 20-30% | 10-20% | <5% | yes |
| EXT 17 | 10-20% | 10-20% | NA | |
| EXT 18 | 10-20% | <5% | NA | yes |

B.

C.

METHODS AND COMPOSITIONS FOR TREATMENT OF CANCER

CROSS-REFERENCE TO RELATED APPLICATIONS

This application claims priority from U.S. Provisional Application Ser. No. 62/798,630 filed on 30 Jan. 2019, which is incorporated herein by reference in its entirety.

STATEMENT REGARDING FEDERALLY SPONSORED RESEARCH OR DEVELOPMENT

This invention was made with government support under CA101937, CA167540, CA197561, CA210084, CA211466, and CA222630 awarded by the National Institutes of Health. The government has certain rights in the invention.

MATERIAL INCORPORATED-BY-REFERENCE

Not applicable.

FIELD OF THE INVENTION

The present disclosure generally relates to cancer therapy.

SUMMARY OF THE INVENTION

Among the various aspects of the present disclosure is the provision of a methods and compositions for upregulating major histocompatibility complex (MHC) class II in cancer cells (e.g., acute myeloid leukemia (AML) cells).

An aspect of the present disclosure provides for a method of increasing or restoring sensitivity of a cancer cell to immune attack from an immune cell, comprising administering IFN-γ to the cancer cell in an amount sufficient to induce upregulation of a MHC class II gene in the cancer cell.

In some embodiments, the cancer cell is a MHC class II-deficient cancer cell.

In some embodiments, the cancer cell is a MHC class II-deficient hematological cancer cell.

In some embodiments, the method comprises administering a hematopoietic stem cell transplant (HCT) comprising donor T cells to the cancer cell having induced upregulation of the MHC class II gene.

In some embodiments, the upregulation of the MHC class II gene in the cancer cell results in sensitizing the MHC class II-deficient hematological cancer cell to graft-versus-leukemia effect; stimulating an immune response from the donor T cells; restoring the ability of the cancer cell to stimulate the donor T cells; or restoring recognition of an antigen of the cancer cell by the donor T cells.

In some embodiments, the cancer cell is from a subject having a relapse of a hematological cancer.

In some embodiments, the cancer cell is from a subject having a relapse of a hematological cancer.

In some embodiments, the subject relapsed after receiving a hematopoietic stem cell transplant (HCT).

In some embodiments, the subject relapsed after receiving a hematopoietic stem cell transplant (HCT), chemotherapy, immunotherapy, radiation, or combinations thereof In some embodiments, the hematological cancer is acute myeloid leukemia (AML).

In some embodiments, the immune cell is an allogenic or donor immune cell.

In some embodiments, the immune cell is an allogenic CD4+ T cell.

In some embodiments, the MHC class II-deficient hematological cancer cell has reduced or deficient MHC class II expression compared to a control or fails to stimulate an immune response from T cells.

In some embodiments, the MHC class II-deficient hematological cancer cell has a downregulated MHC class II gene selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

In some embodiments, the MHC class II gene is selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

Another aspect of the present disclosure provides for a method of treating a subject having or at risk of having a hematological cancer relapse comprising administering a therapeutically effective amount of IFN-γ to the subject.

In some embodiments, the therapeutically effective amount of IFN-γ is an amount sufficient to upregulate MHC class II gene expression in MHC class II-deficient hematological cancer cells.

In some embodiments, the method comprises administering a hematopoietic stem cell transplant (HCT) comprising donor T cells to the subject after administration of IFN-γ.

In some embodiments, the subject has previously received an allogenic transplant comprising donor T cells.

In some embodiments, the therapeutically effective amount of IFN-γ is an amount sufficient to restore the ability of the MHC class II-deficient hematological cancer cells to stimulate the donor T cells.

In some embodiments, the therapeutically effective amount of IFN-γ is an amount sufficient to prevent relapse.

In some embodiments, the therapeutically effective amount of IFN-γ is an amount sufficient to sensitize the MHC class II-deficient hematological cancer cells to graft-versus-leukemia effect.

In some embodiments, the therapeutically effective amount of IFN-γ is an amount sufficient to restore cancer cell antigen recognition by immune cells, enabling the immune system of a subject to eliminate hematological cancer cells.

In some embodiments, the MHC class II-deficient hematological cancer cells have a downregulated MHC class II gene selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

In some embodiments, the therapeutically effective amount of IFN-γ is an amount sufficient to upregulate expression of a MHC class II gene in the MHC class II-deficient hematological cancer cells selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 4A-FIG. 4H is a series of graphs showing clonal evolution of AML in a patient with a relapse after chemotherapy and after transplantation. Clonal evolution with post-chemotherapy and post-transplantation relapse was analyzed in one patient in the study (Patient 452198). (A) Scatter plots of somatic mutations that were found in AML cells obtained at presentation, at relapse after chemotherapy, and at relapse after transplantation according to variant allele frequency. Each data point represents the variant allele frequency of a single somatic mutation in the two indicated samples. At each time point, clusters of mutations are designated with a distinct color and shape to indicate that they represent distinct clonal populations. The mutated genes associated with each cluster are indicated in the key. (B) A "fish plot" that represents the clonal evolution that can be inferred from the variant allele frequencies of somatic mutations that are shown on the scatter plots. Chemotherapy began on day 0, the first relapse was detected at day 505, and the second relapse was detected at day 3269. The dominant subclone at both post-chemotherapy relapse and post-transplantation relapse was derived from a small subclone that was detected at presentation (in red), which evolved with new mutations of unknown significance after each therapy. Single-cell RNA sequencing was performed on cryopreserved presentation and post-transplantation relapse samples. Cells obtained at both presentation and relapse were superimposed onto a single two-dimensional plot and clustered according to their unique expression profiles with the use of t-distributed stochastic neighbor embedding (t-SNE). The axes (t-SNE1 and t-SNE2) show dimensionless values that were assigned to individual cells by the t-SNE algorithm, which places cells that have similar expression profiles close to one another. At presentation (P) and relapse (R), AML cells (AMLP and AMLR) represent the dominant cell type, and small populations of T cells (T cell$^P$ and T cell$^R$) and B cells (B cell$^P$ and B cell$^R$) can also be discerned. (C) A t-SNE plot in which the cells are colored and labeled according to their inferred identity (AMLP, AMLR, B cell, or T cell); AML cells from presentation and relapse have unique expression patterns that identify them as distinct entities. The intensity of the coloring is relative to the expression of each indicated gene. (D) Expression of HLA-DRA is detected in the vast majority of AML cells at presentation but in virtually none at relapse; however, expression of HLA-DRA is detected in B cells at both presentation and relapse. (E) Expression of the housekeeping gene GAPDH is similar in all cell types at both presentation and relapse. Expression of genes associated with T cell exhaustion, (F) ICOS and (G) PD1, is detected in scattered T cells at presentation and is not increased at relapse. (H) Expression of the gene encoding the T cell activation marker granzyme A (GZMA) is strongly detected in a subset of T cells at both presentation and relapse.

FIG. 11A-FIG. 11B is a series of tables and images showing immunohistochemistry for HLA-DR post-transplant. (A) 18 patients had detectable HLA-DR protein. 9/18 patients had decrease in HLA-DR staining at relapse, and 8 of these had <5% blasts staining HLA-DR positive. (B) H&E stained photomicrographs showing regions of AML involvement in presentation and relapse biopsies from two representative cases from the immunohistochemistry cases, EXT11 and EXT8. Brown cytoplasmic stain is HLA-DR protein. Arrow indicates mature neutrophil staining positive for HLA-DR amid HLA-DR negative blasts.

Matched presentation post-chemotherapy (patients 112200, 593890, and 452198) and post-transplant relapse cases (patients 142074, 440422, and 452198) and DNA were subjected to whole genome bisulfite sequencing. (A) CIITA expression (right) and methylation of the CIITA promoter region in paired presentation/relapse samples from post-chemotherapy cases (top left) and post-transplant cases (bottom left). The red box shows an unmethylated region associated with the CIITA promoter, exon 1, and intron 1. (B) Correlation between levels of CIITA promoter methylation and CIITA gene expression. (C) Correlation between CIITA expression and MHC class II genes (HLA-DPA1, HLA-DPB1, HLA-DQA1, HLA-DQB1, HLA-DRA, HLA-DRB1, HLA-DRB3). Since these genes have substantially different expression, CPM values were converted to a "z-score" that gives a relative level of expression.

Figure 17A:
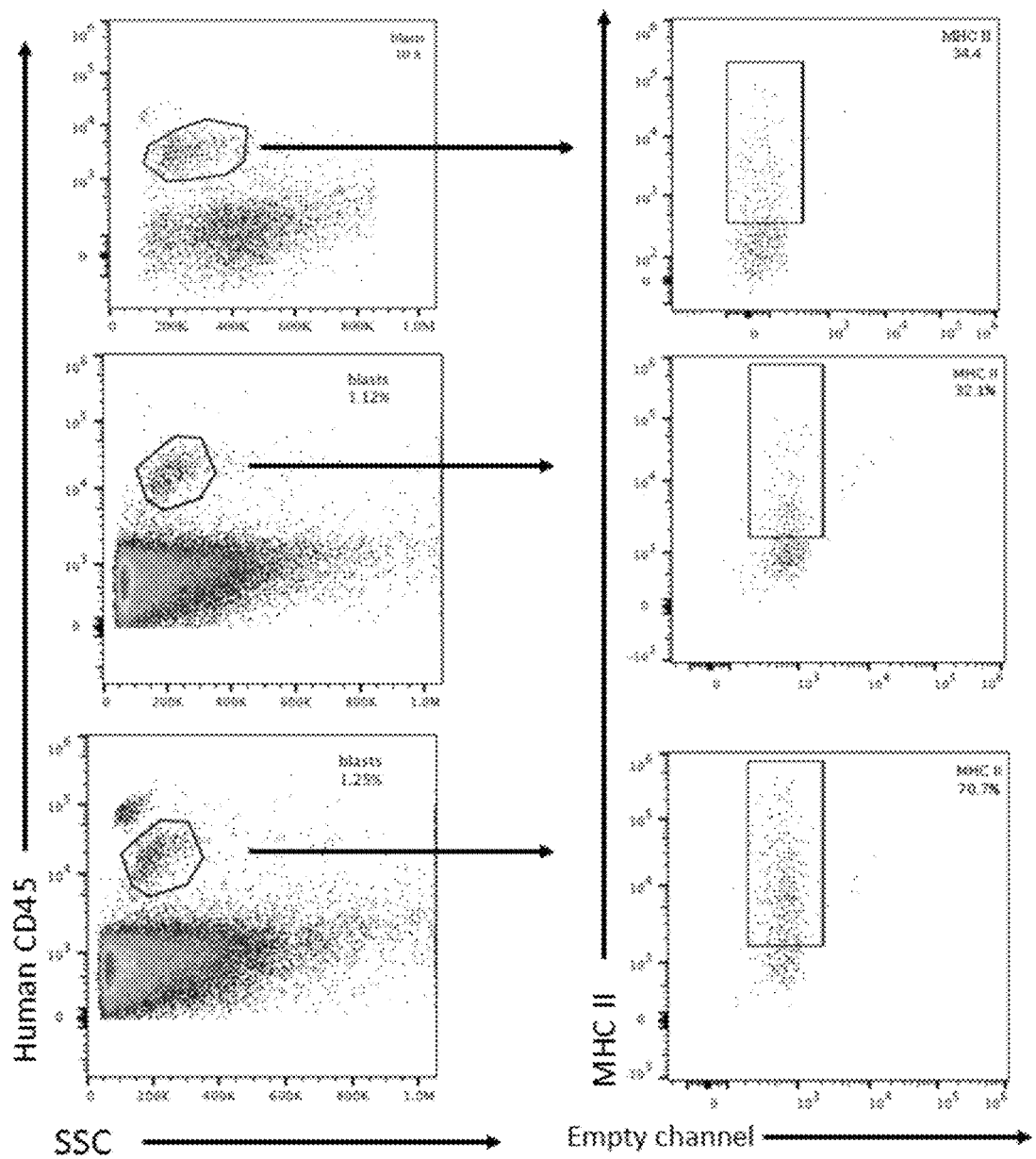
Figure 17B:
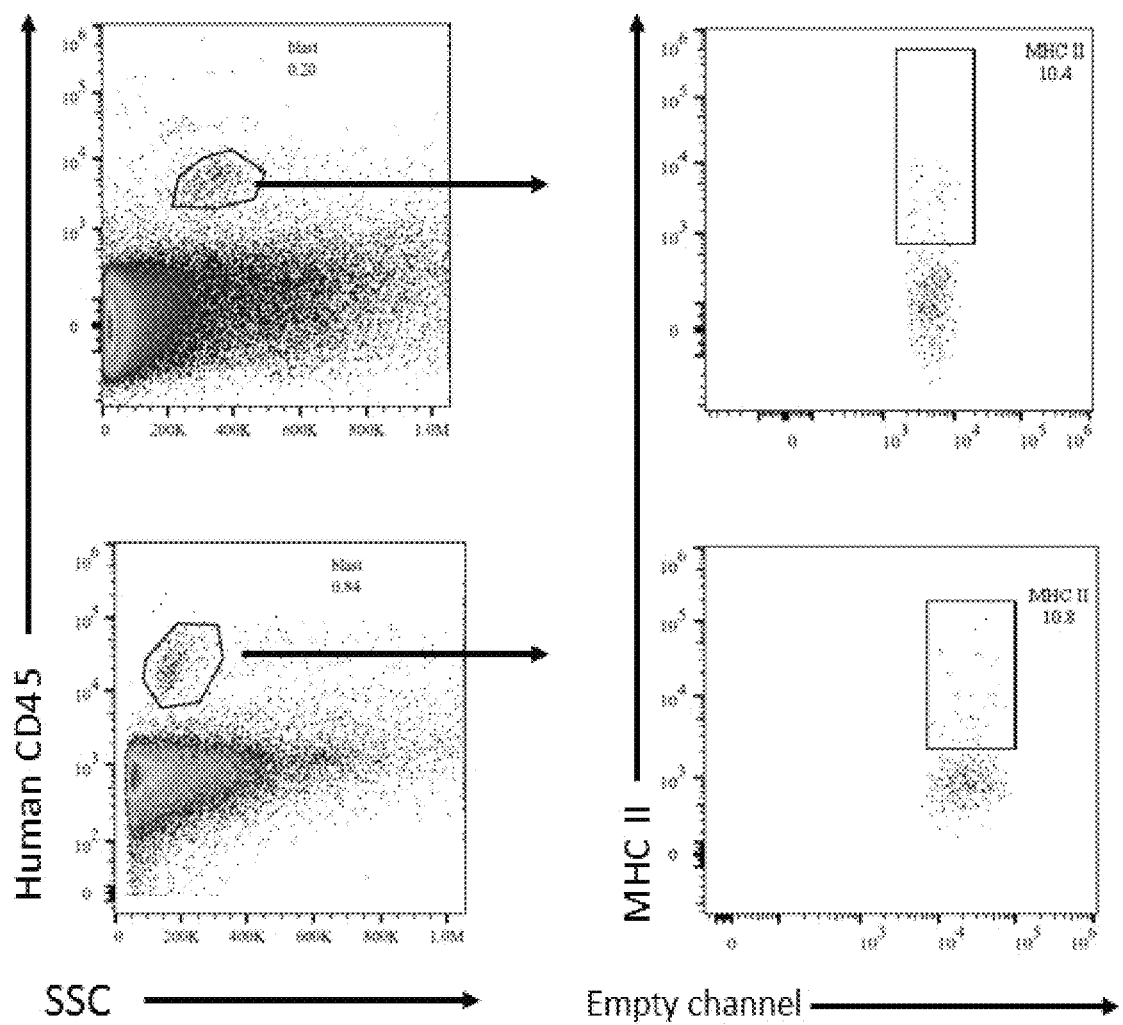

FIG. 17A-FIG. 17B is a series of graphs showing in vivo treatment with interferon gamma (IFN-γ) induces MHC class II expression on MHC class II low AML cells. Immunodeficient mice were engrafted with primary AML cells from a patient with low MHC class II expression at relapse after hematopoietic stem cell transplantation. After engraftment, mice were treated with IFN-γ at 10 µg per dose, three doses weekly x two weeks. (A) Three mice treated with IFN-γ. Left column shows AML blast gate (human CD45 intermediate, side scatter low), right column shows MHC class II expression. (B) Same gating strategy for two mice treated with vehicle only.

DETAILED DESCRIPTION OF THE INVENTION

The present disclosure is based, at least in part, on the discovery that interferon-γ (IFN-γ) treatment leads to robust upregulation of MHC class II proteins or molecules on acute myeloid leukemia (AML) cells from relapsed patients and restores the cancer cell's ability to activate donor T cells.

Roughly half of acute myeloid leukemia (AML) patients who relapse after hematopoietic stem cell transplant (HCT) have reduced expression of immune-related genes in the relapse AML cells, including a significant reduction in expression of MHC class II genes. Because HCT works in part through an immune-mediated "graft-versus-leukemia" effect, it is presently believed that loss of MHC class II expression can lead to reduced surveillance by immune cells post-HCT. As described herein, T cells co-cultured with AML cells from patients that relapsed with low MHC class II expression (a MHC class II-deficient hematological cancer cell) did not show signs of immune cell activation, while co-culture with either diagnosis stage AML samples from the same patients or from relapsed patients with normal MHC class II expression resulted in T cell activation.

IFN-γ

As described herein, interferon-γ (IFN-γ) treatment can to robust upregulation of MHC class II proteins or molecules on cancer cells (e.g., acute myeloid leukemia (AML) cells) from relapsed patients and restores the cancer cell's ability to activate immune cells (e.g., donor T cells). IFN-γ is an immune cytokine with pleiotropic effects on immune effector cells.

As described herein, IFN-γ treatment can lead to robust upregulation of MHC class II on hematological cancer cells (e.g., AML cells) from relapsed patients and restored their ability to stimulate donor immune cells (e.g., T cells) in vitro (see e.g., Example 1). As such, IFN-γ treatment can re-sensitize MHC class II-low (or MHC class II-deficient) cancer cells in patients who relapse after cancer treatment, such as HCT, and restore or increase their sensitivity to donor immune cells present in the graft. For example, AML relapse after HCT represents a significant clinical problem with limited treatment options. While several approaches have been tested to re-sensitize AML cells to immune attack from donor T cells, none have proven satisfactory. It is presently believed that there are no previous studies testing the effect of IFN-γ treatment on relapsed AML patient cells. As described herein, IFN-γ therapy can be a novel and effective therapy for AML and other hematological cancers that relapse after HCT.

Allogenic Transplant

The present disclosure provides for a treatment after an allogenic transplant is received by a subject suffering from a hematological cancer. This type of transplant uses healthy blood-forming cells from an external donor to replace the unhealthy ones in the subject. The transplant can be a hematopoietic stem cell transplant (HCT) or bone marrow transplant/blood stem cell transplant (BMT). The healthy blood-forming cells can be obtained from a family member, unrelated donor, or umbilical cord blood.

Graft-Versus-Leukemia Effect

Allogenic transplantation provides a benefit in part by means of an immune-mediated graft-versus-leukemia effect. Graft-versus-leukemia effect occurs when donor T cells present in the graft or transplant recognize antigens on the surface of hematological cancer cells, enabling the immune system to eliminate these cells. As described herein, it is presently thought that the immune-mediated selective pressure imposed by allogeneic transplantation may cause distinct patterns of tumor evolution in relapsed disease. Although allogeneic transplantation is an effective therapy for patients with hematological cancers and can lead to remission, relapse after transplantation is common and is associated with particularly poor outcomes.

MHC Class II

The present disclosure provides for a method of upregulating major histocompatibility complex (MHC) class II gene or protein expression in a cell (e.g., a MHC class II-deficient hematological cancer cell) for treatment of a subject having cancer. The hematological cancer cells, after relapse, are shown to be deficient in MHC class II expression. It has been shown that downregulation or inactivation of MHC class II expression in acute myeloid leukemia (AML) cells occurs at the time of relapse (see e.g., Example 1). MHC class II genes have a critical role in antigen presentation and stimulation of antitumor immune responses, and their loss in post-transplantation relapse is one mechanism by which relapsing tumors can escape immune surveillance.

As described herein, an MHC class II gene can be any gene that encodes a protein or molecule generally recognized in the art to be a part of MHC class II (e.g., an MHC class II protein or molecule). For example, an MHC class II gene can be a human leukocyte antigen (HLA) gene, such as HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, or HLA-DRB5. As another example, a MHC class II protein or molecule can be any protein or molecule that is encoded by an MHC class II gene. For example, an MHC class II protein or molecule can be an HLA protein, such as HLA-DM, HLA-DO, HLA-DP, HLA-DQ, or HLA-DR.

As described herein, an MHC class II gene can also be any gene that modulates expression of other MHC class II genes. For example, an MHC class II gene can be CIITA.

Upregulation and downregulation of MHC class II expression can be determined by comparing the MHC class II expression in the AML cell compared to a control sample (e.g., an initial presentation sample). Other tests as described herein also use control samples. For example, a control sample or a reference sample as described herein can be a sample from initial presentation of a cancer or from a healthy subject. A reference value can be used in place of a control or reference sample, which was previously obtained from a subject at initial presentation, a healthy subject, a group of subjects with initial presentation or healthy subjects. As another example, a control sample or a reference sample can also be a sample with a known amount of a detectable compound or a spiked sample. As another example, a control can be any control for determining MHC II regulation known in the art.

Hematological Cancers

The present disclosure provides for a method of treating a subject having a hematological cancer or at risk for relapse of a hematological cancer. A hematological cancer generally refers to a cancer that begins in blood-forming cells or tissue, such as immune cells or bone marrow. For example, a hematological cancer can be acute myeloid leukemia (AML), acute lymphoblastic leukemia (ALL), acute monocytic leukemia (AMoL), chronic lymphocytic leukemia (CLL), chronic myelogenous leukemia (CML), hairy cell leukemia, AIDS-related lymphoma, cutaneous T-cell lymphoma, Hodgkin lymphoma, mycosis fungoides, non-Hodgkin lymphoma, primary central nervous system lymphoma, Sezary syndrome, Waldenstrom macroglobulinemia, chronic myeloproliferative neoplasms, Langerhans cell histiocytosis, multiple myeloma, myelodysplastic syndrome, or myelodysplastic/myeloproliferative neoplasms.

Relapse

The present disclosure provides for a treatment useful for transplant failure in cancers, such as AML, and similar disorders.

As described herein, administration of IFN-γ can be used to treat or prevent (if administered prophylactically) relapse in a subject suffering from a hematological cancer, particularly cancers that have cancer cells deficient in MHC class II expression. Relapse generally refers to the return of the cancer in a subject after the subject initially demonstrated complete remission of the disease after treatment (e.g., hematopoietic stem cell transplant (HCT), chemotherapy, antibody therapy, etc.). Relapse can also be any transplant failure in the treatment of a hematological cancer. For example, a relapse can occur between about 2 months and about 5 years after initial remission of disease. Generally, most relapses occur within the first 18 months of remission. But late relapse (at least 5 years of remission) can rarely occur in patients.

As described herein, a relapse can be an extramedullary relapse. An extramedullary relapse refers to a recurrence of a leukemia in sites other than the bone marrow (e.g., central nervous system, brain, spinal cord). Extramedullary relapse can be manifested as a myeloid sarcoma (chloroma, granulocytic sarcoma, extramedullary myeloid tumor), which is a solid tumor composed of immature white blood cells. Extramedullary relapse occurs more commonly after hematopoietic stem cell transplant than after chemotherapy or at presentation.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a cancer, hematological cancer (e.g., AML), or a solid tumor or preventing a relapse in a subject in need of administration of a therapeutically effective amount of IFN-γ, so as to re-sensitize MHC class II-deficient cells, restore or increase cell sensitivity to donor T cells present in the graft, to upregulate MHC class II on cells, inhibit the proliferation of a hematological cancer or a solid tumor; slow the progress of a hematological cancer or a solid tumor; or limit the development or proliferation of a hematological cancer or a solid tumor.

Methods described herein are generally performed on a subject in need thereof. A subject in need of the therapeutic methods described herein can be a subject having, diagnosed with, suspected of having, or at risk for developing a hematological cancer or a solid tumor. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of IFN-γ, for example, an amount that would cause the desired therapeutic effect in a subject while minimizing undesired side effects. In various embodiments, an effective amount of IFN-γ described herein can substantially inhibit a hematological cancer or a solid tumor, slow the progress of a hematological cancer or a solid tumor, or limit the development of a hematological cancer or a solid tumor.

When used in the treatments described herein, a therapeutically effective amount of IFN-γ can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to re-sensitize MHC class II-low cells, restore or increase cell sensitivity to donor T cells present in the graft, to upregulate MHC class II on cells, inhibit a hematological cancer or a solid tumor proliferation; slow the progress of a hematological cancer or a solid tumor; or limit the development of a hematological cancer or a solid tumor.

The amount of a composition described herein that can be combined with a pharmaceutically acceptable carrier to produce a single dosage form will vary depending upon the subject treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of IFN-γ can occur as a single event or over a time course of treatment. For example, IFN-γ can be administered daily, weekly, bi-weekly, or monthly. The time course of treatment can be at least several days to several weeks. For example, treatment could extend over one week, two weeks, or three weeks. As another example, treatment could extend from several weeks to several months or even a year or more.

Treatment in accord with the methods described herein can be performed prior to, concurrent with, or after conventional treatment modalities for hematological cancer (e.g., AML) or a solid tumor.

IFN-γ can be administered simultaneously or sequentially with another cancer therapy (e.g., antibody, chemotherapy, HCT, radiation, immunotherapy). Simultaneous administration can occur through administration of separate compositions, each containing one or more of IFN-γ or cancer therapy. Simultaneous administration can occur through administration of one composition containing two or more of IFN-γ or cancer therapies.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal administration.

Agents and compositions described herein can be administered in a variety of methods well known in the arts. Administration can include, for example, direct injection (e.g., systemic or stereotactic). Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Immune Escape of Relapsed AML Cells after Allogeneic Transplantation The following example describes dysregulation of pathways that influence immune function in acute myeloid leukemia (AML) relapse after transplantation.

Abstract

Background: As consolidation therapy for acute myeloid leukemia (AML), allogeneic hematopoietic stem-cell transplantation (HCT) provides a benefit in part by means of an immune-mediated graft-versus-leukemia (GVL) effect (the ability of donor immune cells to eliminate host leukemic cells after allogeneic HCT). It is presently thought that the immune-mediated selective pressure imposed by allogeneic transplantation may cause distinct patterns of tumor evolution in relapsed disease.

Methods: As described herein, enhanced exome sequencing was performed on paired samples obtained at initial presentation with AML and at relapse from 15 patients who had a relapse after hematopoietic stem-cell transplantation (with transplants from an human leukocyte antigen (HLA)-matched sibling, HLA-matched unrelated donor, or HLA-mismatched unrelated donor) and from 20 patients who had a relapse after chemotherapy. RNA sequencing and flow cytometry were performed on a subgroup of these samples and on additional samples for validation.

Figure 13:
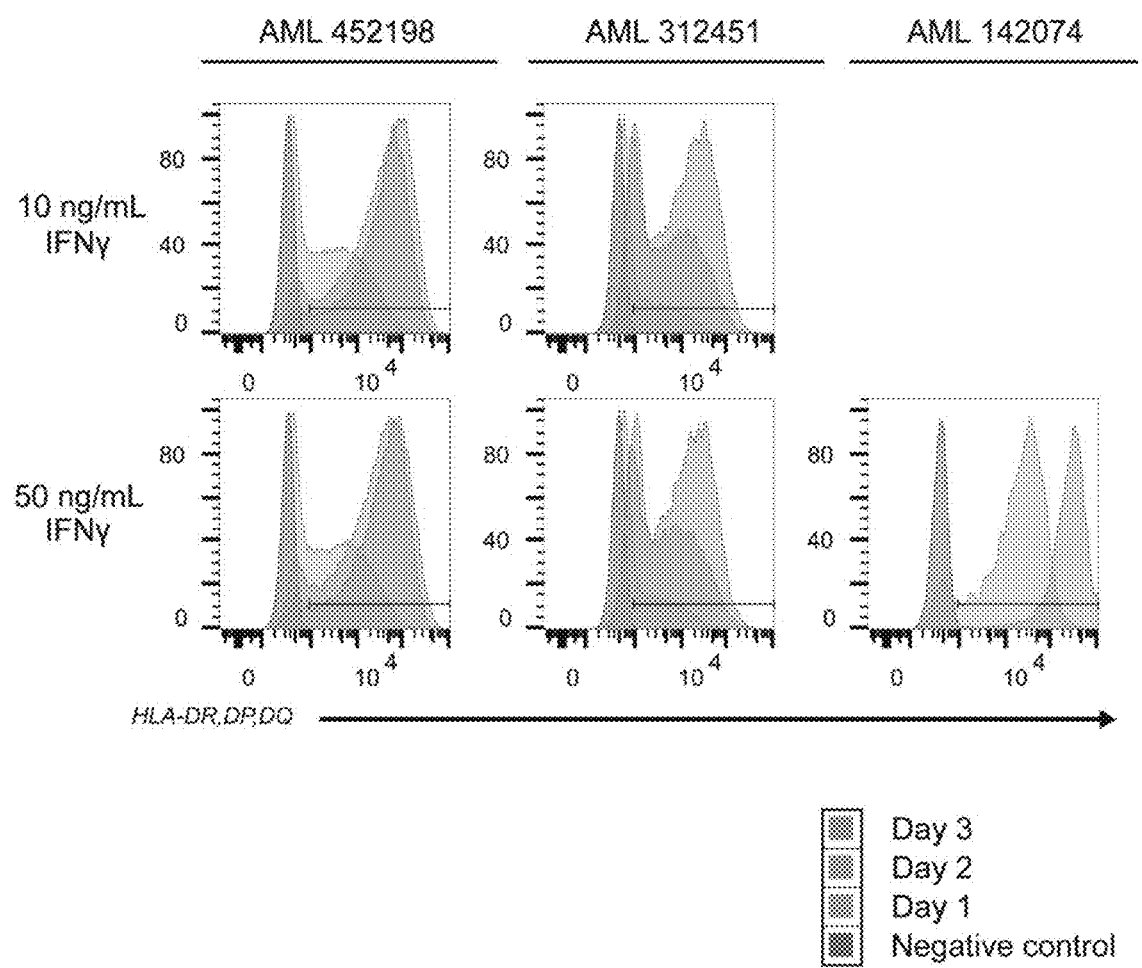
FIG. 13 is a graph showing induction of MHC class II expression with interferon gamma (IFN-γ). Cryopreserved leukemia cells from 3 post-transplant relapse samples with downregulated MHC class II expression were cultured for up to 72 hours in the presence or absence of IFN-γ, 10 ng/ml (top panels) or 50 ng/ml (bottom panels). MHC class II expression in the blast population was assessed by flow cytometry at different time points, as indicated. Negative controls represent fluorescence-minus-one controls.
Figures 14A, 14B, 14C:
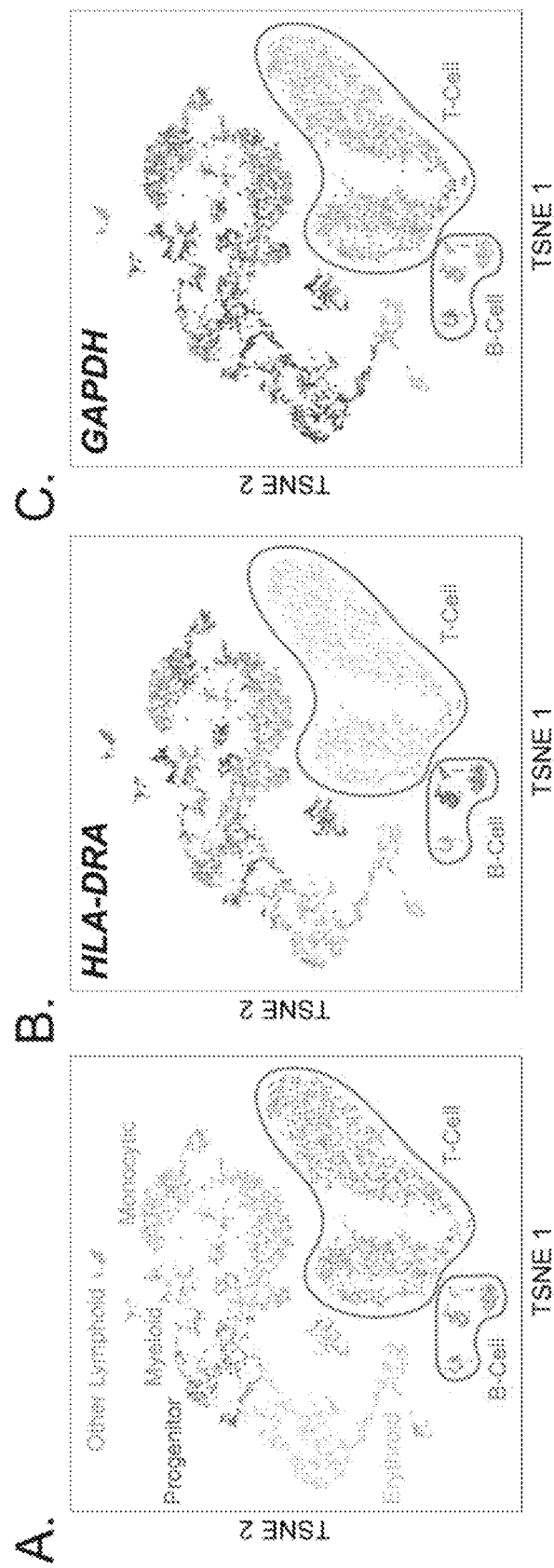
FIG. 14A-FIG. 14F is a series of graphs showing single-cell RNA sequencing of normal bone marrow. Single-cell RNA sequencing was performed on cryopreserved normal bone marrows from healthy adult individuals (N=4). Cells from all 4 samples were superimposed on a single 2D plot and clustered based on their unique expression profiles using t-distributed stochastic neighbor embedding (t-SNE). (A) t-SNE plot of normal bone marrow cells with pseudo-coloring of cells based on RNA expression, and identification of the lineages of each population. Cell populations from different samples cluster together. Color intensity shows expression of (B) HLA-DRA, (C) GAPDH, (D) ICOS, (E) PD1, or (F) GZMA within each population.
Figures 14D, 14E, 14F:
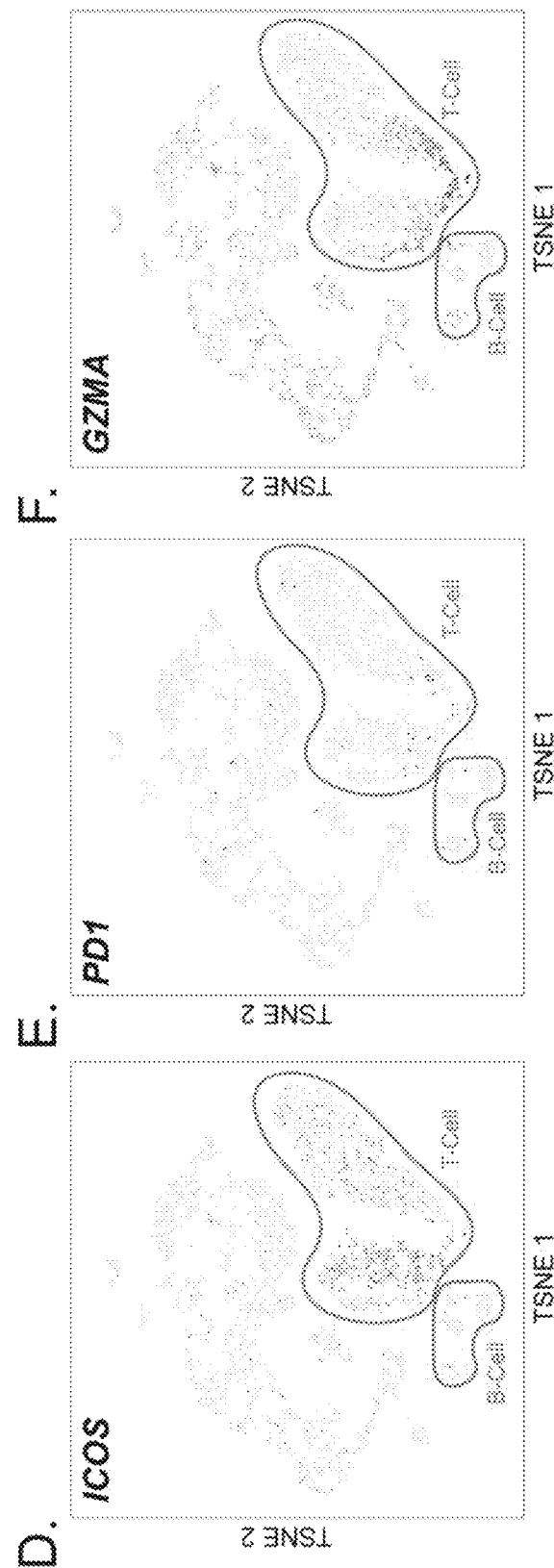

Results: On exome sequencing, the spectrum of gained and lost mutations observed with relapse after transplantation was similar to the spectrum observed with relapse after chemotherapy. Specifically, relapse after transplantation was not associated with the acquisition of previously unknown AML-specific mutations or structural variations in immune-related genes. In contrast, RNA sequencing of samples obtained at relapse after transplantation revealed dysregulation of pathways involved in adaptive and innate immunity, including downregulation of major histocompatibility complex (MHC) class II genes (HLA-DPA1, HLA-DPB1, HLA-DQB1, and HLA-DRB1) to levels that were 3 to 12 times lower than the levels seen in paired samples obtained at presentation. Flow cytometry and immunohistochemical analysis confirmed decreased expression of MHC class II at relapse in 17 of 34 patients who had a relapse after transplantation. Evidence suggested that interferon-γ treatment could rapidly reverse this phenotype in AML blasts in vitro and in vivo (see e.g., FIG. 13, FIG. 17A-FIG. 17B).

Conclusions: AML relapse after transplantation was not associated with the acquisition of relapse-specific mutations in immune-related genes. However, it was associated with dysregulation of pathways that may influence immune function, including downregulation of MHC class II genes, which are involved in antigen presentation. These epigenetic changes may be reversible with appropriate therapy.

Background

Most patients with acute myeloid leukemia (AML) ultimately have a relapse and die from progressive disease, despite initial sensitivity to chemotherapy. For this reason, patients who are in complete remission generally receive consolidation treatment with either additional chemotherapy or allogeneic hematopoietic stem-cell transplantation, a therapy that is thought to provide a benefit in part by means of an immune-mediated graft-versus-leukemia effect. Although allogeneic transplantation is an effective therapy for patients with AML, relapse after transplantation is common and is associated with particularly poor outcomes.

At relapse, AML cells often develop chromosomal gains and losses, and this finding has long suggested that therapeutic selective pressure can cause clonal evolution. It has been previously reported that AML relapse after chemotherapy has often been associated with gains and losses of subclones that contain unique somatic mutations, including putative driver mutations. Recent studies that investigated the clonal evolution associated with AML relapse after transplantation were focused on recurrently mutated AML genes; although the presence of certain mutations can be used to predict an increased risk of relapse, the mechanisms by which these mutations promote relapse remain unclear.

Previous studies showed downregulation or inactivation of major histocompatibility complex (MHC) genes in AML cells at the time of relapse. MHC genes have a critical role in antigen presentation and stimulation of antitumor immune responses, and their loss in post-transplantation relapse is one clear-cut mechanism by which relapsing tumors can escape immune surveillance. In patients who have received a transplant from a haploidentical donor, elimination of the mismatched HLA allele can occur; this event is uncommon in HLA-matched transplantation. In this study, a comprehensive analysis of samples from patients who had a relapse of AML after transplantation was performed to define the genetic and epigenetic alterations that allow leukemic cells to escape the graft-versus-leukemia effect and to determine whether the dysregulation of known immune-related genes is a common feature of relapse after transplantation.

Methods

Patients

Samples were obtained as part of a study that was approved by the Human Research Protection Office at Washington University School of Medicine. All the patients provided written informed consent that permitted whole-genome sequencing, in accordance with a protocol that was approved by the institutional review board at the Washington University School of Medicine. For the discovery group, patients were identified who had adequate banked samples that were obtained at initial presentation with AML and at relapse; 15 adult patients had a relapse of AML after allogeneic hematopoietic stem-cell transplantation, and 20 adult patients had a relapse of AML after chemotherapy (14 of whom were included in a previous study). To validate changes in MHC class II expression on flow cytometry or immunohistochemical analysis, additional samples from 28 patients who had a relapse of AML after transplantation were analyzed.

Molecular Analyses

DNA and RNA were isolated from samples of cryopreserved patient bone marrow. Samples with a low percentage of AML blasts were flow-sorted to enrich the blast population before the isolation of DNA or RNA. Control samples of skin or purified T cells (in two patients) were also sequenced, which allowed for variants to be defined as somatically acquired. Immunohistochemical analysis for HLA-DR was performed by NeoGenomics Laboratories and interpreted by a board-certified hematopathologist.

Statistical Analyses

On the basis of the binomial probability distribution and a sample of 15 patients who had a relapse after transplantation, the Stat Trek calculator was used to calculate the likelihood of detecting a previously unknown relapse-specific mutation. If such a mutation were to have a true prevalence of 50% among all patients with a post-transplantation relapse, then the probability that the mutation would be observed in at least 3 of the 15 patients would be more than 90%.

Enhanced Exome Sequencing

Sequence data were aligned to reference sequence build GRCh37-lite-build37 using bwa version 0.5.9 (parameters: -t=4, -q=5), then merged and deduplicated using picard version 1.46.

Somatic SNVs were detected using a combination of Samtools, Sniper, Varscan, and Strelka. First, the intersection of Samtools version r963 (parameters: -A -B; filter: V1), and SomaticSniper version 1.0.2 (parameters: -F vcf -q 1 -Q 15; filters: false-positive-filter v1 (parameters: --bam-readcount-version 0.4, -bam-readcount-min-base-quality 15), somatic-score-mapping-quality v1 (parameters: -min-mapping-quality 40 -min-somatic-score 40)) were obtained. Second, the union of VarScan version 2.2.6 (filters: varscan-high-confidence filter version v1, false-positive filter v1 (parameters: --bam-readcount-version 0.4 --bam-readcount-min-base-quality 15)), and Strelka version 0.4.6.2 (parameters: isSkipDepthFilters=1) were obtained. Finally, the union of (1) the combined Samtools-and-Sniper output and (2) the combined Varscan-and-Strelka output were obtained.

Somatic indels were obtained from the union of the output of 4 methods: (1) GATK somatic-indel version 5336, filtered using false-indel version v1 (parameters: --bam-readcount-version 0.4 --bam-readcount-min-base-quality 15), (2) Pindel version 0.5, filtered with pindel-somatic-calls v1, pindel-vaf-filter v1 (parameters: --variant-freq-cutoff 0.08), and pindel-read-support v1, (3) VarScan version 2.2.6, filtered with varscan-high-confidence-indel version v1, then with false-indel version v1 (parameters: --bam-readcount-version 0.4 --bam-readcount-min-base-quality 15), and (4) Strelka version 0.4.6.2 (parameters: isSkipDepthFilters=1).

Copy number analysis was performed using VarScan2. Loss of heterozygosity (LOH) was identified using Varscan. Regions with at least 10 contiguous probes and at least 95% LOH were considered to have undergone LOH.

Validation Sequencing

Sequence data were aligned to reference sequence build GRCh37-lite-build37 using bwa version 0.5.9 (parameters: -t=4, -q=5), merged using picard version 1.462, and deduplicated using picard version 1.46 api v2.

Somatic SNVs were obtained from the union of the output of Varscan and Strelka. Varscan v2.2.6 (parameters: --min-var-freq 0.08 --p-value 0.10 --somatic-p-value 0.01 --validation) output was filtered with the varscan-high-confidence filter v1 and the false-positive filter v1 (parameters: --bam-readcount-min-base-quality 15 --bam-readcount-version 0.6). Indels were detected using four methods, as above, but with updated versions of Strelka (1.0.10) and bam-readcount (0.6).

Variant Filtering

Most samples from the post-transplant cohort were sequenced twice. For each of these samples, all variants identified during either the EES or validation sequencing runs were considered, and read counts were combined across the runs. Variants that are commonly found in normal samples (based on a large set of in-house sequencing data) were excluded. Of the remaining variants, variants were retained based on the following criteria: had a read-depth of at least 30 in all samples from the same patient; had at least 3 variant reads and a VAF 5 in at least one sample; scored above noise in at least 1 sample according to a binomial test (LLR threshold=10 for 113971 (post-allo relapse sample), 633734 (post-allo relapse sample) and 593890 (all samples), LLR threshold=3 for all other samples); had an EVS or dbSNP allele frequency below 0.1; and passed manual review of aligned sequence data. Known AML hotspot mutations (see e.g., TABLE 1) were included if they had at least three variant reads and a VAF 5 in at least one sample, regardless of the other criteria.

TABLE 1

Table of hotspot variants used for variant filtering.

| Chromosome | Start | Stop | Reference | Variant | Type | Gene name | Position | Amino acid change |
|---|---|---|---|---|---|---|---|---|
| 11 | 32417909 | 32417910 | — | ACCGTACA | INS | WT1 | c.1143_1142 | p.A382fs |
| 13 | 28592628 | 28592628 | A | C | SNP | FLT3 | c.2517 | p.D839E |

TABLE 1-continued

Table of hotspot variants used for variant filtering.

| Chromosome | Start | Stop | Reference | Variant | Type | Gene name | Position | Amino acid change |
|---|---|---|---|---|---|---|---|---|
| 13 | 28592628 | 28592628 | A | G | SNP | FLT3 | c.2517 | p.D839 |
| 13 | 28592628 | 28592628 | A | T | SNP | FLT3 | c.2517 | p.D839E |
| 13 | 28592629 | 28592629 | T | A | SNP | FLT3 | c.2516 | p.D839V |
| 13 | 28592629 | 28592629 | T | C | SNP | FLT3 | c.2516 | p.D839G |
| 13 | 28592629 | 28592629 | T | G | SNP | FLT3 | c.2516 | p.D839A |
| 13 | 28592630 | 28592630 | C | A | SNP | FLT3 | c.2515 | p.D839Y |
| 13 | 28592630 | 28592630 | C | G | SNP | FLT3 | c.2515 | p.D839H |
| 13 | 28592630 | 28592630 | C | T | SNP | FLT3 | c.2515 | p.D839N |
| 13 | 28592637 | 28592637 | G | A | SNP | FLT3 | c.2508 | p.I836 |
| 13 | 28592637 | 28592637 | G | C | SNP | FLT3 | c.2508 | p.I836M |
| 13 | 28592637 | 28592637 | G | T | SNP | FLT3 | c.2508 | p.I836 |
| 13 | 28592638 | 28592638 | A | C | SNP | FLT3 | c.2507 | p.I836S |
| 13 | 28592638 | 28592638 | A | G | SNP | FLT3 | c.2507 | p.I836T |
| 13 | 28592638 | 28592638 | A | T | SNP | FLT3 | c.2507 | p.I836N |
| 13 | 28592639 | 28592639 | T | A | SNP | FLT3 | c.2506 | p.I836F |
| 13 | 28592639 | 28592639 | T | C | SNP | FLT3 | c.2506 | p.I836V |
| 13 | 28592639 | 28592639 | T | G | SNP | FLT3 | c.2506 | p.I836L |
| 13 | 28592640 | 28592640 | A | C | SNP | FLT3 | c.2505 | p.D835E |
| 13 | 28592640 | 28592640 | A | G | SNP | FLT3 | c.2505 | p.D835 |
| 13 | 28592640 | 28592640 | A | T | SNP | FLT3 | c.2505 | p.D835E |
| 13 | 28592641 | 28592641 | T | A | SNP | FLT3 | c.2504 | p.D835V |
| 13 | 28592641 | 28592641 | T | C | SNP | FLT3 | c.2504 | p.D835G |
| 13 | 28592641 | 28592641 | T | G | SNP | FLT3 | c.2504 | p.D835A |
| 13 | 28592642 | 28592642 | C | A | SNP | FLT3 | c.2503 | p.D835Y |
| 13 | 28592642 | 28592642 | C | G | SNP | FLT3 | c.2503 | p.D835H |
| 13 | 28592642 | 28592642 | C | T | SNP | FLT3 | c.2503 | p.D835N |
| 15 | 90631837 | 90631837 | C | A | SNP | IDH2 | c.516 | p.R172S |
| 15 | 90631837 | 90631837 | C | G | SNP | IDH2 | c.516 | p.R172S |
| 15 | 90631837 | 90631837 | C | T | SNP | IDH2 | c.516 | p.R172 |
| 15 | 90631838 | 90631838 | C | A | SNP | IDH2 | c.515 | p.R172M |
| 15 | 90631838 | 90631838 | C | G | SNP | IDH2 | c.515 | p.R172T |
| 15 | 90631838 | 90631838 | C | T | SNP | IDH2 | c.515 | p.R172K |
| 15 | 90631839 | 90631839 | T | A | SNP | IDH2 | c.514 | p.R172W |
| 15 | 90631839 | 90631839 | T | C | SNP | IDH2 | c.514 | p.R172G |
| 15 | 90631839 | 90631839 | T | G | SNP | IDH2 | c.514 | p.R172 |
| 15 | 90631933 | 90631933 | C | A | SNP | IDH2 | c.420 | p.R140 |
| 15 | 90631933 | 90631933 | C | G | SNP | IDH2 | c.420 | p.R140 |
| 15 | 90631933 | 90631933 | C | T | SNP | IDH2 | c.420 | p.R140 |
| 15 | 90631934 | 90631934 | C | A | SNP | IDH2 | c.419 | p.R140L |
| 15 | 90631934 | 90631934 | C | G | SNP | IDH2 | c.419 | p.R140P |
| 15 | 90631934 | 90631934 | C | T | SNP | IDH2 | c.419 | p.R140Q |
| 15 | 90631935 | 90631935 | G | A | SNP | IDH2 | c.418 | p.R140W |
| 15 | 90631935 | 90631935 | G | C | SNP | IDH2 | c.418 | p.R140G |
| 15 | 90631935 | 90631935 | G | T | SNP | IDH2 | c.418 | p.R140 |
| 17 | 7577119 | 757719 | A | C | SNP | TP53 | c.819 | p.R273 |
| 17 | 7577119 | 757719 | A | G | SNP | TP53 | c.819 | p.R273 |
| 17 | 7577119 | 757719 | A | T | SNP | TP53 | c.819 | p.R273 |
| 17 | 7577120 | 757710 | C | A | SNP | TP53 | c.818 | p.R273L |
| 17 | 7577120 | 757710 | C | G | SNP | TP53 | c.818 | p.R273P |
| 17 | 7577120 | 757710 | C | T | SNP | TP53 | c.818 | p.R27H |
| 17 | 7577121 | 757711 | G | A | SNP | TP53 | c.817 | p.R273C |
| 17 | 7577121 | 757711 | G | C | SNP | TP53 | c.817 | p.R273G |
| 17 | 7577121 | 757711 | G | T | SNP | TP53 | c.817 | p.R273S |
| 17 | 7577534 | 757754 | C | A | SNP | TP53 | c.747 | p.R249S |
| 17 | 7577534 | 757754 | C | G | SNP | TP53 | c.747 | p.R249S |
| 17 | 7577534 | 7577534 | C | T | SNP | TP53 | c.747 | p.R249 |
| 17 | 7577535 | 7577535 | C | A | SNP | TP53 | c.746 | p.R249M |
| 17 | 7577535 | 7577535 | G | G | SNP | TP53 | c.746 | p.R249T |
| 17 | 7577535 | 7577535 | C | T | SNP | TP53 | c.746 | p.R249K |
| 17 | 7577536 | 7577536 | T | A | SNP | TP53 | c.745 | p.R249W |
| 17 | 7577536 | 7577536 | T | C | SNP | TP53 | c.745 | p.R249G |
| 17 | 7577537 | 7577537 | C | A | SNP | TP53 | c.744 | p.R248 |
| 17 | 7577537 | 7577537 | C | G | SNP | TP53 | c.744 | p.R248 |
| 17 | 7577537 | 7577537 | C | T | SNP | TP53 | c.744 | p.R248 |
| 17 | 7577538 | 7577538 | C | A | SNP | TP53 | c.743 | p.R248L |
| 17 | 7577538 | 7577538 | C | G | SNP | TP53 | c.743 | p.R248P |
| 17 | 7577538 | 7577538 | C | T | SNP | TP53 | c.743 | p.R248Q |
| 17 | 7577539 | 7577539 | G | A | SNP | TP53 | c.742 | p.R248W |
| 17 | 7577539 | 7577539 | G | C | SNP | TP53 | c.742 | p.R248G |
| 17 | 7577539 | 7577539 | G | T | SNP | TP53 | c.742 | p.R248 |
| 17 | 7578189 | 7578189 | A | C | SNP | TP53 | c.660 | p.Y220* |
| 17 | 7578189 | 7578189 | A | G | SNP | TP53 | c.660 | p.Y220 |
| 17 | 7578189 | 7578189 | A | T | SNP | TP53 | c.660 | p.Y220* |
| 17 | 7578190 | 7578190 | T | A | SNP | TP53 | c.659 | p.Y220F |

TABLE 1-continued

Table of hotspot variants used for variant filtering.

| Chromosome | Start | Stop | Reference | Variant | Type | Gene name | Position | Amino acid change |
|---|---|---|---|---|---|---|---|---|
| 17 | 7578190 | 7578190 | T | C | SNP | TP53 | c.659 | p.Y220C |
| 17 | 7578190 | 7578190 | T | G | SNP | TP53 | c.659 | p.Y220S |
| 17 | 7578191 | 7578191 | A | C | SNP | TP53 | c.658 | p.Y220D |
| 17 | 7578191 | 7578191 | A | G | SNP | TP53 | c.658 | p.Y220H |
| 17 | 7578191 | 7578191 | A | T | SNP | TP53 | c.658 | p.Y220N |
| 17 | 7578411 | 7578411 | C | A | SNP | TP53 | c.519 | p.V173 |
| 17 | 7578411 | 7578411 | C | G | SNP | TP53 | c.519 | p.V173 |
| 17 | 7578411 | 7578411 | C | T | SNP | TP53 | c.519 | p.V173 |
| 17 | 7578412 | 7578412 | A | C | SNP | TP53 | c.518 | p.V173G |
| 17 | 7578412 | 7578412 | A | G | SNP | TP53 | c.518 | p.V173A |
| 17 | 7578412 | 7578412 | A | T | SNP | TP53 | c.518 | p.V173E |
| 17 | 7578413 | 7578413 | C | A | SNP | TP53 | c.517 | p.V173L |
| 17 | 7578413 | 7578413 | C | G | SNP | TP53 | c.517 | p.V173L |
| 17 | 7578413 | 7578413 | C | T | SNP | TP53 | c.517 | p.V173M |
| 1 | 36933433 | 36933433 | G | A | SNP | CSF3R | c.509 | p.P170L |
| 1 | 36933433 | 36933433 | G | C | SNP | CSF3R | c.509 | p.P170R |
| 1 | 36933433 | 36933433 | G | T | SNP | CSF3R | c.509 | p.P170H |
| 1 | 36933434 | 36933434 | G | A | SNP | CSF3R | c.1853 | p.T618I |
| 1 | 36933434 | 36933434 | G | C | SNP | CSF3R | c.1853 | p.T618S |
| 1 | 36933434 | 36933434 | G | T | SNP | CSF3R | c.1853 | p.T618N |
| 1 | 36933435 | 36933435 | T | A | SNP | CSF3R | c.1852 | p.T618S |
| 1 | 36933435 | 36933435 | T | C | SNP | CSF3R | c.1852 | p.T618A |
| 1 | 36933435 | 36933435 | T | G | SNP | CSF3R | c.1852 | p.T618P |
| 21 | 36231781 | 36231781 | T | A | SNP | RUNX1 | c.603 | p.R201 |
| 21 | 36231781 | 36231781 | T | C | SNP | RUNX1 | c.603 | p.R201 |
| 21 | 36231781 | 36231781 | T | G | SNP | RUNX1 | c.603 | p.R201 |
| 21 | 36231782 | 36231782 | G | A | SNP | RUNX1 | c.602 | p.R201L |
| 21 | 36231782 | 36231782 | C | G | SNP | RUNX1 | c.602 | p.R201P |
| 21 | 36231782 | 36231782 | C | T | SNP | RUNX1 | c.602 | p.R201Q |
| 21 | 38231783 | 36231783 | G | A | SNP | RUNX1 | c.601 | p.R201* |
| 21 | 36231783 | 36231783 | G | C | SNP | RUNX1 | c.601 | p.R201G |
| 21 | 38231783 | 36231783 | G | T | SNP | RUNX1 | c.601 | p.R201 |
| 21 | 36252876 | 36252876 | C | A | SNP | RUNX1 | c.486 | p.R162S |
| 21 | 36252876 | 36252876 | C | G | SNP | RUNX1 | c.486 | p.R162S |
| 21 | 36252876 | 36252876 | C | T | SNP | RUNX1 | c.486 | p.R162 |
| 21 | 36252877 | 36252877 | C | A | SNP | RUNX1 | c.485 | p.R162M |
| 21 | 36252877 | 36252877 | C | G | SNP | RUNX1 | c.485 | p.R162T |
| 21 | 36252877 | 36252877 | C | T | SNP | RUNX1 | c.485 | p.R162K |
| 21 | 36252878 | 36252878 | T | A | SNP | RUNX1 | c.484 | p.R162W |
| 21 | 36252878 | 36252878 | T | C | SNP | RUNX1 | c.484 | p.R162G |
| 21 | 36252878 | 36252878 | T | G | SNP | RUNX1 | c.484 | p.R162 |
| 21 | 44514776 | 44514776 | C | A | SNP | U2AF1 | c.471 | p.Q157H |
| 21 | 44514776 | 44514776 | C | G | SNP | U2AF1 | c.471 | p.Q157H |
| 21 | 44514776 | 44514776 | C | T | SNP | U2AF1 | c.471 | p.Q157 |
| 21 | 44514777 | 44514777 | T | A | SNP | U2AF1 | c.470 | p.Q157L |
| 21 | 44514777 | 44514777 | T | C | SNP | U2AF1 | c.470 | p.Q157R |
| 21 | 44514777 | 44514777 | T | G | SNP | U2AF1 | c.470 | p.Q157P |
| 21 | 44514778 | 44514778 | G | A | SNP | U2AF1 | c.469 | p.Q157* |
| 21 | 44514778 | 44514778 | G | C | SNP | U2AF1 | c.469 | p.Q157E |
| 21 | 44514778 | 44514778 | G | T | SNP | U2AF1 | c.469 | p.Q157K |
| 21 | 44524455 | 44524455 | A | C | SNP | U2AF1 | c.102 | p.S34 |
| 21 | 44524455 | 44524455 | A | G | SNP | U2AF1 | c.102 | p.S34 |
| 21 | 44524455 | 44524455 | A | T | SNP | U2AF1 | c.102 | p.S34 |
| 21 | 44524456 | 44524456 | G | A | SNP | U2AF1 | c.101 | p.S34F |
| 21 | 44524456 | 44524456 | G | C | SNP | U2AF1 | c.101 | p.S34C |
| 21 | 44524456 | 44524456 | G | T | SNP | U2AF1 | c.101 | p.S34Y |
| 21 | 44524457 | 44524457 | A | C | SNP | U2AF1 | c.100 | p.S34A |
| 21 | 44524457 | 44524457 | A | G | SNP | U2AF1 | c.100 | p.S34P |
| 21 | 44524457 | 44524457 | A | T | SNP | U2AF1 | c.100 | p.S34T |
| 2 | 198286832 | 198266832 | T | A | SNP | SF3B1 | c.2100 | p.K700N |
| 2 | 198266832 | 198266832 | T | C | SNP | SF3B1 | c.2100 | p.K700 |
| 2 | 198266832 | 198266832 | T | G | SNP | SF3B1 | c.2100 | p.K700N |
| 2 | 198266833 | 198266833 | T | A | SNP | SF3B1 | c.2099 | p.K700I |
| 2 | 198266833 | 198266833 | T | C | SNP | SF3B1 | c.2099 | p.K700R |
| 2 | 198266833 | 198266833 | T | G | SNP | SF3B1 | c.2099 | p.K700T |
| 2 | 198266834 | 198266834 | T | A | SNP | SF3B1 | c.2098 | p.K700* |
| 2 | 198266834 | 198266834 | T | C | SNP | SF3B1 | c.2098 | p.K700E |
| 2 | 198266834 | 198266834 | T | G | SNP | SF3B1 | c.2098 | p.K700Q |
| 2 | 198267359 | 198267359 | C | A | SNP | SF3B1 | c.1998 | p.K666N |
| 2 | 198267359 | 198267359 | C | G | SNP | SF3B1 | c.1998 | p.K666N |
| 2 | 198267359 | 198267359 | C | T | SNP | SF3B1 | c.1998 | p.K666 |
| 2 | 198267360 | 19826730 | T | A | SNP | SF3B1 | c.1997 | p.K666M |
| 2 | 198267360 | 198267360 | T | C | SNP | SF3B1 | c.1997 | p.K666R |
| 2 | 198267360 | 198267360 | T | G | SNP | SF3B1 | c.1997 | p.K666T |

TABLE 1-continued

Table of hotspot variants used for variant filtering.

| Chromosome | Start | Stop | Reference | Variant | Type | Gene name | Position | Amino acid change |
|---|---|---|---|---|---|---|---|---|
| 2 | 198267361 | 198267361 | T | A | SNP | SF3B1 | c.1996 | p.K666* |
| 2 | 198267361 | 198267361 | T | C | SNP | SF3B1 | c.1996 | p.K666E |
| 2 | 198267361 | 198267361 | T | G | SNP | SF3B1 | c.1996 | p.K666Q |
| 2 | 209113111 | 209113111 | A | C | SNP | IDH1 | c.396 | p.R132 |
| 2 | 209113111 | 209113111 | A | G | SNP | IDH1 | c.396 | p.R132 |
| 2 | 209113111 | 209113111 | A | T | SNP | IDH1 | c.396 | p.R132 |
| 2 | 209113112 | 209113112 | C | A | SNP | IDH1 | c.395 | p.R132L |
| 2 | 209113112 | 209113112 | C | G | SNP | IDH1 | c.395 | p.R132P |
| 2 | 209113112 | 209113112 | C | T | SNP | IDH1 | c.395 | p.R132H |
| 2 | 209113113 | 209113113 | G | A | SNP | IDH1 | c.394 | p.R132C |
| 2 | 209113113 | 209113113 | G | C | SNP | IDH1 | c.394 | p.R132G |
| 2 | 209113113 | 209113113 | G | T | SNP | IDH1 | c.394 | p.R132S |
| 2 | 25457241 | 25457241 | G | A | SNP | DNMT3A | c.2646 | p.R882 |
| 2 | 25457241 | 25457241 | G | C | SNP | DNMT3A | c.2646 | p.R882 |
| 2 | 25457241 | 25457241 | G | T | SNP | DNMT3A | c.2646 | p.R882 |
| 2 | 25457242 | 25457242 | C | A | SNP | DNMT3A | c.2645 | p.R882L |
| 2 | 25457242 | 25457242 | C | G | SNP | DNMT3A | c.2645 | p.R882P |
| 2 | 25457242 | 25457242 | C | T | SNP | DNMT3A | c.2645 | p.R882H |
| 2 | 25457243 | 25457243 | G | A | SNP | DNMT3A | c.2644 | p.R882C |
| 2 | 25457243 | 25457243 | G | C | SNP | DNMT3A | c.2644 | p.R882G |
| 2 | 25457243 | 25457243 | G | T | SNP | DNMT3A | c.2644 | p.R882S |
| 3 | 128200111 | 128200111 | C | A | SNP | GATA2 | c.1194 | p.R398 |
| 3 | 128200111 | 128200111 | C | G | SNP | GATA2 | c.1194 | p.R398 |
| 3 | 128200111 | 128200111 | G | T | SNP | GATA2 | c.1194 | p.R398 |
| 3 | 128200112 | 128200112 | C | A | SNP | GATA2 | c.1193 | p.R398L |
| 3 | 128200112 | 128200112 | C | G | SNP | GATA2 | c.1193 | p.R398P |
| 3 | 128200112 | 128200112 | C | T | SNP | GATA2 | c.1193 | p.R398Q |
| 3 | 128200113 | 128200113 | G | A | SNP | GATA2 | c.1192 | p.R398W |
| 3 | 128200113 | 128200113 | G | C | SNP | GATA2 | c.1192 | p.R398G |
| 3 | 128200113 | 128200113 | G | T | SNP | GATA2 | c.1192 | p.R398 |
| 3 | 128200743 | 128200743 | C | A | SNP | GATA2 | c.1062 | p.T354 |
| 3 | 128200743 | 128200743 | C | G | SNP | GATA2 | c.1062 | p.T354 |
| 3 | 128200743 | 128200743 | C | T | SNP | GATA2 | c.1062 | p.T354 |
| 3 | 128200744 | 128200744 | G | A | SNP | GATA2 | c.1061 | p.T354M |
| 3 | 128200744 | 128200744 | G | C | SNP | GATA2 | c.1061 | p.T354R |
| 3 | 128200744 | 128200744 | G | T | SNP | GATA2 | c.1061 | p.T354K |
| 3 | 128200745 | 128200745 | T | A | SNP | GATA2 | c.1060 | p.T354S |
| 3 | 128200745 | 128200745 | T | C | SNP | GATA2 | c.1060 | p.T354A |
| 3 | 128200745 | 128200745 | T | G | SNP | GATA2 | c.1060 | p.T354P |
| 4 | 55599322 | 55599322 | T | A | SNP | KIT | c.2448 | p.D816E |
| 4 | 55599322 | 55599322 | T | C | SNP | KIT | c.2448 | p.D816 |
| 4 | 55599322 | 55599322 | T | G | SNP | KIT | c.2448 | p.D816E |
| 5 | 170837546 | 170837547 | — | CATG | INS | NPM1 | c.882_863 | p.W288fs |
| 5 | 170837546 | 170837547 | — | CCTG | INS | NPM1 | c.862_863 | p.W288fs |
| 5 | 170837546 | 170837547 | — | TCAG | INS | NPM1 | c.862_863 | p.W288fs |
| 5 | 170837546 | 170837547 | — | TCTG | INS | NPM1 | c.862_863 | p.W288fs |
| 9 | 5073770 | 5073770 | G | A | SNP | JAK2 | c.1849 | p.V617I |
| 9 | 5073770 | 5073770 | G | C | SNP | JAK2 | c.1849 | p.V617L |
| 9 | 5073770 | 5073770 | G | T | SNP | JAK2 | c.1849 | p.V617F |
| 9 | 5073771 | 5073771 | T | A | SNP | JAK2 | c.1850 | p.V617D |
| 9 | 5073771 | 5073771 | T | C | SNP | JAK2 | c.1850 | p.V617A |
| 9 | 5073771 | 5073771 | T | G | SNP | JAK2 | c.1850 | p.V617G |
| 9 | 5073772 | 5073772 | C | A | SNP | JAK2 | c.1851 | p.V617 |
| 9 | 5073772 | 5073772 | C | G | SNP | JAK2 | c.1851 | p.V617 |
| 9 | 5073772 | 5073772 | C | T | SNP | JAK2 | c.1851 | p.V617 |
| 12 | 25378560 | 25378560 | T | A | SNP | KRAS | c.438 | p.A146 |
| 12 | 25378560 | 25378560 | T | C | SNP | KRAS | c.438 | p.A146 |
| 12 | 25378560 | 25378560 | T | G | SNP | KRAS | c.438 | p.A146 |
| 12 | 25378561 | 25378561 | G | A | SNP | KRAS | c.437 | p.A146V |
| 12 | 25378561 | 25378561 | G | C | SNP | KRAS | c.437 | p.A146G |
| 12 | 25378561 | 25378561 | G | T | SNP | KRAS | c.437 | p.A146E |
| 12 | 25378562 | 25378562 | G | A | SNP | KRAS | c.436 | p.A146S |
| 12 | 25378562 | 25378562 | C | G | SNP | KRAS | c.436 | p.A146P |
| 12 | 25378562 | 25378562 | C | T | SNP | KRAS | c.436 | p.A146T |
| 12 | 25378647 | 25378647 | T | A | SNP | KRAS | c.351 | p.K117N |
| 12 | 25378647 | 25378647 | T | C | SNP | KRAS | c.351 | p.K117 |
| 12 | 25378647 | 25378647 | T | G | SNP | KRAS | c.351 | p.K117N |
| 12 | 25378648 | 25378648 | T | A | SNP | KRAS | c.350 | p.K117I |
| 12 | 25378648 | 25378648 | T | C | SNP | KRAS | c.350 | p.K117R |
| 12 | 25378648 | 25378648 | T | G | SNP | KRAS | c.350 | p.K117T |
| 12 | 25378649 | 25378649 | T | A | SNP | KRAS | c.349 | p.K117* |
| 12 | 25378649 | 25378649 | T | C | SNP | KRAS | c.349 | p.K117E |
| 12 | 25378649 | 25378649 | T | G | SNP | KRAS | c.349 | p.K117Q |
| 12 | 25380275 | 25380275 | T | A | SNP | KRAS | c.183 | p.Q61H |

TABLE 1-continued

Table of hotspot variants used for variant filtering.

| Chromosome | Start | Stop | Reference | Variant | Type | Gene name | Position | Amino acid change |
|---|---|---|---|---|---|---|---|---|
| 12 | 25380275 | 25380275 | T | C | SNP | KRAS | c.183 | p.Q61 |
| 12 | 25380275 | 25380275 | T | G | SNP | KRAS | c.183 | p.Q61H |
| 12 | 25380276 | 25380276 | T | A | SNP | KRAS | c.182 | p.Q81L |
| 12 | 25380276 | 25380276 | T | C | SNP | KRAS | c.182 | p.G61R |
| 12 | 25380276 | 25380276 | T | G | SNP | KRAS | c.182 | p.Q61P |
| 12 | 25380277 | 25380277 | G | A | SNP | KRAS | c.181 | p.Q61* |
| 12 | 25380277 | 25380277 | G | C | SNP | KRAS | c.181 | p.Q61E |
| 12 | 25380277 | 25380277 | G | T | SNP | KRAS | c.181 | p.Q61K |
| 12 | 25398280 | 25398280 | G | A | SNP | KRAS | c.39 | p.G13 |
| 12 | 25398280 | 25398280 | G | C | SNP | KRAS | c.39 | p.G13 |
| 12 | 25398280 | 25398280 | G | T | SNP | KRAS | c.39 | p.G13 |
| 12 | 25398281 | 25398281 | C | A | SNP | KRAS | c.38 | p.G13V |
| 12 | 25398281 | 25398281 | C | G | SNP | KRAS | c.38 | p.G13A |
| 12 | 25398281 | 25398281 | C | T | SNP | KRAS | c.38 | p.G13D |
| 12 | 25398282 | 25398282 | C | A | SNP | KRAS | c.37 | p.G13C |
| 12 | 25398282 | 25398282 | C | G | SNP | KRAS | c.37 | p.G13R |
| 12 | 25398282 | 25398282 | C | T | SNP | KRAS | c.37 | p.G13S |
| 12 | 25398283 | 25398283 | A | C | SNP | KRAS | c.36 | p.G12 |
| 12 | 25398283 | 25398283 | A | G | SNP | KRAS | c.36 | p.G12 |
| 12 | 25398283 | 25398283 | A | T | SNP | KRAS | c.36 | p.G12 |
| 12 | 25398284 | 25398284 | C | A | SNP | KRAS | c.35 | p.G12V |
| 12 | 25398284 | 25398284 | C | G | SNP | KRAS | c.35 | p G12A |
| 12 | 25398284 | 25398284 | C | T | SNP | KRAS | c.35 | p.G12D |
| 12 | 25398285 | 25398285 | C | A | SNP | KRAS | c.34 | p.G12C |
| 12 | 25398285 | 25398285 | C | G | SNP | KRAS | c.34 | p.G12R |
| 12 | 25398285 | 25398285 | C | T | SNP | KRAS | c.34 | p.G12S |
| 1 | 115256528 | 115256528 | T | A | SNP | NRAS | c.183 | p.Q61H |
| 1 | 115256528 | 115256528 | T | C | SNP | NRAS | c.183 | p.Q61 |
| 1 | 115256528 | 115256528 | T | G | SNP | NRAS | c.183 | p.Q61H |
| 1 | 115256529 | 115256529 | T | A | SNP | NRAS | c.182 | p.Q61L |
| 1 | 115256529 | 115256529 | T | C | SNP | NRAS | c.182 | p.G61R |
| 1 | 115256529 | 115256529 | T | G | SNP | NRAS | c.182 | p.Q61P |
| 1 | 115256530 | 115256530 | G | A | SNP | NRAS | c.181 | p.Q61* |
| 1 | 115256530 | 115256530 | G | C | SNP | NRAS | c.181 | p.Q61E |
| 1 | 115256530 | 115256530 | G | T | SNP | NRAS | c.181 | p.Q61K |
| 1 | 115258743 | 115258743 | A | C | SNP | NRAS | c.39 | p.G13 |
| 1 | 115256743 | 115258743 | A | G | SNP | NRAS | c.39 | p.G13 |
| 1 | 115258743 | 115258743 | A | T | SNP | NRAS | c.39 | p.G13 |
| 1 | 115258744 | 115258744 | C | A | SNP | NRAS | c.38 | p.G13V |
| 1 | 115256744 | 115258744 | C | G | SNP | NRAS | c.38 | p.G13A |
| 1 | 115258744 | 115258744 | C | T | SNP | NRAS | c.38 | p.G13D |
| 1 | 115256745 | 115258745 | C | A | SNP | NRAS | c.37 | p.G13C |
| 1 | 115258745 | 115258745 | C | G | SNP | NRAS | c.37 | p.G13R |
| 1 | 115258745 | 115258745 | C | T | SNP | NRAS | c.37 | p.G13S |
| 1 | 115258746 | 115258746 | A | C | SNP | NRAS | c.36 | p.G12 |
| 1 | 115258746 | 115258746 | A | G | SNP | NRAS | c.36 | p.G12 |
| 1 | 115256746 | 115258746 | A | T | SNP | NRAS | c.36 | p.G12 |
| 1 | 115258747 | 115258747 | C | A | SNP | NRAS | c.35 | p.G12V |
| 1 | 115258747 | 115258747 | C | G | SNP | NRAS | c.35 | p.G12A |
| 1 | 115258747 | 115258747 | C | T | SNP | NRAS | c.35 | p.G12D |
| 1 | 115258748 | 115258748 | C | A | SNP | NRAS | c.34 | p.G12C |
| 1 | 115258748 | 115258748 | C | G | SNP | NRAS | c.34 | p.G12R |
| 1 | 115258748 | 115258748 | C | T | SNP | NRAS | c.34 | p.G12S |
| 7 | 140453135 | 140453135 | C | T | SNP | BRAF | c.1800 | p.V600 |
| 7 | 140453136 | 140453136 | A | C | SNP | BRAF | c.1799 | p.V600G |
| 7 | 140453136 | 140453136 | A | G | SNP | BRAF | c.1799 | p.V600A |
| 7 | 140453136 | 140453136 | A | T | SNP | BRAF | c.1799 | p.V600E |
| 7 | 140453137 | 140453137 | C | A | SNP | BRAF | c.1798 | p.V600L |
| 7 | 140453137 | 140453137 | C | G | SNP | BRAF | c.1798 | p.V600L |
| 7 | 140453137 | 140453137 | C | T | SNP | BRAF | c.1798 | p.V600M |
| 9 | 5073770 | 5073770 | G | A | SNP | JAK2 | c.1849 | p.V617I |
| 9 | 5073770 | 5073770 | G | C | SNP | JAK2 | c.1849 | p.V617L |
| 9 | 5073770 | 5073770 | G | T | SNP | JAK2 | c.1849 | p.V617F |
| 9 | 5073771 | 5073771 | T | A | SNP | JAK2 | c.1850 | p.V617D |
| 9 | 5073771 | 5073771 | T | C | SNP | JAK2 | c.1850 | p.V617A |
| 9 | 5073771 | 5073771 | T | G | SNP | JAK2 | c.1850 | p.V617G |
| 9 | 5073772 | 5073772 | C | A | SNP | JAK2 | c.1851 | p.V617 |
| 9 | 5073772 | 5073772 | C | G | SNP | JAK2 | c.1851 | p.V617 |
| 9 | 5073772 | 5073772 | C | T | SNP | JAK2 | c.1851 | p.V617 |
| 9 | 5078360 | 5078360 | A | C | SNP | JAK2 | c.2047 | p.R683 |
| 9 | 5078360 | 5078360 | A | G | SNP | JAK2 | c.2047 | p.R683G |
| 9 | 5078360 | 5078360 | A | T | SNP | JAK2 | c.2047 | p.R683* |
| 9 | 5078361 | 5078361 | G | A | SNP | JAK2 | c.2048 | p.R683K |
| 9 | 5078361 | 5078361 | G | C | SNP | JAK2 | c.2048 | p.R683T |

TABLE 1-continued

Table of hotspot variants used for variant filtering.

| Chromosome | Start | Stop | Reference | Variant | Type | Gene name | Position | Amino acid change |
|---|---|---|---|---|---|---|---|---|
| 9 | 5078361 | 5078361 | G | T | SNP | JAK2 | c.2048 | p.R683I |
| 9 | 5078362 | 5078362 | A | C | SNP | JAK2 | c.2049 | p.R683S |
| 9 | 5078362 | 5078362 | A | G | SNP | JAK2 | c.2049 | p.R683 |
| 9 | 5078362 | 5078362 | A | T | SNP | JAK2 | c.2049 | p.R683S |

The Haplotect algorithm was used to estimate the rate of residual donor contamination in each sorted post-transplant sample. Specifically, the upper limit of the 95% confidence interval of Haplotect's "mle_multi" estimate was used as the estimate of contamination, which in these samples ranged from 4-12%. For each variant that was detected in a given post-transplant sample, but not in the corresponding primary tumor sample, a binomial test was performed to determine whether the VAF was significantly greater than the estimated contamination rate for that sample. Variants were retained if the one-sided p-value, adjusted for multiple testing, was at most 0.025.

Mitochondrial mutations and mutations associated with transcript annotation errors were removed. Variants that were believed to represent Clonal Hematopoiesis of Indeterminate Potential (CHIP) were removed. The VAFs of X-chromosome variants in males were corrected by dividing the observed VAF by 2. All samples were manually reviewed to identify FLT3 internal tandem duplications and NPM1 insertions (and their corresponding VAFs) that may have been missed by the algorithms above. This resulted in the inclusion of 4 variants: a FLT3 ITD and an NPM1 insertion in each of the AMLs 312451 and 327733. Two variants identified using fluorescent in situ hybridization (FISH) were also included: an MLL-ELL fusion in AML 242129, and a CBFB-MYH11 fusion in AML 619751.

RNA-Seq Data Analysis

Kallisto v0.43.0 was used to quantify transcript abundances (default parameters), using a GRCh37 transcriptome index generated from Ensembl v74 (default parameters). Kallisto's transcript-level abundance estimates were converted into length-scaled, gene-level counts using the R package tximport v1.0.3. EdgeR v3.14.0 was used to filter genes based on counts per million (CPM>1 in at least 10 samples), normalize counts using the TMM algorithm, and identify genes that are differentially expressed between primary and relapse samples. Specifically, 2 separate linear models were fit to the data: the first was fit to the paired primary and post-transplantation relapse samples; the second was fit to the paired primary and post-chemo relapse samples. p-values for the fits were obtained using a likelihood ratio test, and false discovery rates (FDRs) were calculated using the Benjamini-Hochberg method. A gene was classified as differentially expressed if its FDR was at most 0.05. These calculations were performed in R v3.3.1. Gene Ontology enrichment analysis was performed using ToppFun, which uses a hypergeometric test to determine the significance of the enrichment. The resulting p-value is the probability of obtaining the observed intersection (between a set of differentially expressed genes and the genes in the annotated functional category) by chance. Multiple hypothesis correction in gene set enrichment analysis was done using the Benjamini-Hochberg method for controlling the false discovery rate.

As a quality control for sample purity, variant allele frequency (VAF) of each variant present in RNA sequencing of post-transplant and post-chemotherapy cohorts was compared to that variant's VAF as established by previous DNA sequencing. Samples with poor correlation between DNA and RNA were excluded (AML161510, AML242129, AML275291, AML303642, AML763312, AML275291).

Bisulfite Sequencing Analysis

Bisulfite sequencing reads were mapped with BSMAP (version 2.74) using default parameters, followed by quantification of methylation ratios with the included methratio.py script. Differentially methylated regions between diagnosis and post-transplant samples were called using metilene v.0.2-6.

Flow Cytometry

Flow cytometry was performed as previously described. For flow sorting of AML cells, cryovials were thawed in 40% FBS in PBS and stained with the following antibodies: PerCP-Cy5.5-conjugated anti-human CD45 (eBiosciences, San Diego, Calif.; clone 2D1), FITC-conjugated anti-human CD19 (BD Pharmingen, Franklin Lakes, N.J.; clone H1B19), e450-conjugated anti-human CD3 (eBiosciences, clone OKT3), PE-conjugated anti-human CD34 (Miltenyi, Auburn, Calif.; PE-pool, PN IM1459U). For MHC Class II analysis, cells were stained with anti-human CD45 and a BV421-conjugated Mouse Anti-Human HLA-DR, DP, DQ antibody (BD Biosciences, San Jose, Calif.; clone Tu39).

Cell Culture

Culture of primary AML samples was performed as previously described. Briefly, cryovials with primary cells were thawed in PBS containing 30% FBS, centrifuged, resuspended in media with cytokines, and plated on HS27 stromal cells. Cells were cultured with or without interferon gamma (10 ng/ml or 50 ng/ml, Peprotech, Rocky Hill, N.J.) and were analyzed at different timepoints for MHC class II expression by flow cytometry as described above.

Mixed Lymphocyte Reaction

Cryopreserved peripheral blood or bone marrow mononuclear cells from AML patients were thawed, washed, and cultured overnight on human HS27 stromal cells as before. The non-adherent cells were collected, irradiated (3500 cGy), and used as stimulators. Third party (MHC mismatched) CD4+T lymphocytes were isolated from healthy PBMC donors by negative selection using an AutoMACS device per the manufacturer's instructions (Miltenyi Biotech, Auburn, Calif.) and used as responders. In the human interferon gamma enzyme linked immunospot (ELISPOT) assay, $3.3 \times 10^4$ CD4+ T cells were plated with $1 \times 10^5$ stimulator cells in precoated human IFN-γ ELISPOT plates (Cellular Technology Ltd., Shaker Heights, Ohio) containing 200 μl of serum-free Stemline T cell expansion medium (Sigma-Aldrich, St. Louis, Mo.) supplemented with 1% GlutaMax (Life Technologies, Invitrogen, Waltham, Mass.) and 1% Corning Cellgro penicillin-streptomycin solution (Mediatech, Manassas, Va.).

Stimulation of CD4+ T cells with phorbol 12-myristate 13-acetate (PMA; 5 ng/mL) and ionomycin (1 ng/ml; Sigma-Aldrich, St. Louis, Mo.) was used as a positive control. Triplicate wells of T cells or AML stimulators alone were used as the background control. Plates were incubated at 37° C. for 36 hours and analyzed by C.T.L. ImmunoSpot kit and ImmunoSpot S6 analyzer (Cellular Technology Ltd., Shaker Heights, Ohio). In parallel, flow cytometric analysis of separate MLR cultures was performed to determine the percentage of CD4+ T cells that became activated in response to allo-stimulation. Here, $2\times10^5$ CD4+ T cells were plated with $2\times10^5$ stimulator cells in 96-well round bottom plates containing 200 µl of serum-free Stemline T cell expansion medium supplemented with 10% human AB serum, 1% GlutaMax, and 1% Corning Cellgro penicillin-streptomycin solution. Stimulation of CD4+ T cells with Dynabeads human T activator CD3/CD28 beads (1 bead per cell; Thermo Fisher Scientific, Waltham, Mass.) was used as a positive control and unstimulated T cells were used as the background control. Plates were incubated at 37° C. for 4 to 5 days. Cells were then harvested, resuspended in staining buffer (PBS supplemented with 0.5% bovine serum albumin and 2 mM EDTA) and incubated for 30 min at 4° C. with pre-titrated saturating dilutions of the following fluorochrome-labeled monoclonal antibodies (BD Biosciences; clone designated in parenthesis): CD3 (UCHT1), CD4 (SK3), CD8 (SK1), CD14 (MPHIP9), CD33 (P67.6), CD34 (581), CD45 (2D1), CD117 (YB5.138), CD123 (7G3), CD279 (EH12.1), and CD137 (4134-1). Dead cells were excluded from these assays by staining with 2 µg/ml 7-amino-actinomycin D (Molecular Probes, Eugene, Oreg.) for 5 min prior to analysis. Appropriate isotype-matched negative controls were used to assess background fluorescence intensity and set gates for negative populations.

Samples were analyzed on a Gallios flow cytometer (Beckman Coulter, Brea, Calif.) and data were analyzed using FlowJo software (TreeStar, Ashland, Oreg.). The percentage of viable CD45+/CD3+/CD4+/CD137+/CD279+ T cells within the entire CD45+/CD3+/CD4+/CD8-/CD14-/CD33-/CD34-/CD117-/CD123-subset was quantified.

Single Cell RNA Sequencing

The Chromium instrument and the Single Cell 3' Solution from 10x Genomics were used to generate scRNA-seq data for paired presentation/relapse samples from AML 452198, and whole bone marrow samples from four healthy donors.

Briefly, cryopreserved cells were thawed as described above, viable cells were flow sorted based on propridium iodide exclusion and resuspended in 1×PBS containing 0.04% weight/volume BSA. Aliquots were partitioned using the Chromium instrument into as many as 18,000 nanoliter-scale Gel Bead-in-Emulsions (GEMs). cDNA libraries were prepared from individual GEM-partitioned cells using the Chromium Single Cell 3' Chip Kit v2 (PN-120236), Library & Gel Bead Kit v2 (PN-120237), and Chromium i7 Multi-plex Kit (PN-120262), according to the instructions in the Chromium™ Single Cell 3' Reagent Kits v2 User Guide, Rev A. cDNA libraries were sequenced on the Illumine HiSeq 4000 to a depth of at least 50,000 reads/cell. Cell-Ranger (10x Genomics) and the cellrangerRkit package (10x Genomics) were used to demultiplex and align the sequencing reads, correct and count the UMIs for each gene in each cell, normalize the data to account for differences in sequencing depth across samples, exclude genes with zero UMI counts, normalize read depth across cells within each data set, perform dimensionality reduction, and perform k-means and graph-based clustering. Cell-type inference was performed in an unsupervised, marker-free manner by training a nearest-neighbor algorithm on expression data from the DMAP database, and in a supervised manner used known cell-type markers.

TABLE 2

Single cell RNA sequencing read counts.

| Sample | Number of Cells | Total Reads/ Cell | Reads/Cell Mapped to Transcriptome | Median Genes/ Cell | Total genes detected | Median UMI counts per cell |
|---|---|---|---|---|---|---|
| 452198 Presentation | 18,126 | 79,616 | 38,773 | 1,381 | 21,342 | 3,570 |
| 452198 Relapse | 10,429 | 141,786 | 70,752 | 1,438 | 21,036 | 4,144 |
| Normal 1 | 1,724 | 291,981 | 155,626 | 1,404 | 20,124 | 4,728 |
| Normal 2 | 2,435 | 172,633 | 97,538 | 1,004 | 18,945 | 3,210 |
| Normal 3 | 1,954 | 404,932 | 241,340 | 1,650 | 19,885 | 6,815 |
| Normal 4 | 1,944 | 396,078 | 240,420 | 1,817 | 19,694 | 7,614 |

Results

Analysis for Relapse-Specific Mutations

To determine whether AML relapse after transplantation was associated with recurrent mutations, enhanced exome sequencing on samples from 15 patients who had a relapse after transplantation was performed, including 6 patients who presented with isolated extramedullary disease. The transplants had been from HLA-matched related donors, HLA-matched unrelated donors, or HLA-mismatched unrelated donors; no transplants had been from haploidentical donors (see e.g., TABLE 3).

TABLE 3

Patient cohort used in this study and associated clinical data.

| UPN | Relapse type | FAB | Age | cytogenetic risk | Transplant type | remission status at transplant | relapse day from diagnosis | Relapse site | RNA-seq | Recurrently mutated AML genes at diagnosis |
|---|---|---|---|---|---|---|---|---|---|---|
| 103342 | after HCT | M2 | 60 | intermediate | MUD | CR1* | 1095 | bone marrow | yes | CBL, SRSF2, TET2, RUNX1, NRAS, STAG2 |
| 142074 | after HCT | M4 | 61 | intermediate | SIB | CR1 | 300 | bone marrow | yes | TET2, DNMT3A, NPM1, NLRC4 |
| 161510 | after HCT | M2 | 44 | intermediate | MUD | PD | 218 | bone marrow | | IDH1, WT1, PTPN11, NRAS, WT1 |
| 242129 | after HCT | M4 | 51 | poor | MUD | CR2 | 403 | bone marrow | | MLL-ELL fusion, SHC1, KRAS |

TABLE 3-continued

Patient cohort used in this study and associated clinical data.

| UPN | Relapse type | FAB | Age | cytogenetic risk | Transplant type | remission status at transplant | relapse day from diagnosis | Relapse site | RNA-seq | Recurrently mutated AML genes at diagnosis |
|---|---|---|---|---|---|---|---|---|---|---|
| 312451 | after HCT | M2 | 18 | intermediate | MMUD (9/10) | CR1 | 285 | bone marrow | yes | FLT3-ITD, NPM1 |
| 440422 | after HCT | M0 | 69 | intermediate | MMUD (9/10) | PD | 708 | bone marrow | yes | RUNX1, IDH2, SRSF2, ASXL1 |
| 619751 | after HCT | M4 | 57 | good | MUD | CR2 | 493 | bone marrow | yes | inv(16), ARAP2, KIT, WT1 |
| 814916 | after HCT | M2 | 63 | poor | MMUD (9/10) | CR1 | 653 | bone marrow | yes | TP53, PTPN11, SETBP1 |
| 452198 | after HCT | M4 | 55 | intermediate | SIB | CR2 | 3269 | bone marrow | yes | DNMT3A, NPM1, FLT3-ITD, IDH1, FOXP1, PTPN11 |
| 112200 | after HCT | M4 | 43 | good | SIB | CR2 | 2027 | extramedullary |  | inv(16), XIRP, NRAS |
| 113971 | after HCT | M2 | 57 | intermediate | MUD | CR1 | 711 | extramedullary |  | DNMT3A, TOP3B, KRAS, IDH2 |
| 327733 | after HCT | M1 | 32 | intermediate | MUD | CR2 | 995 | extramedullary |  | IDH1, NPM1, FLT3-ITD |
| 593890 | after HCT | M2 | 35 | intermediate | MUD | CR2 | 1024 | extramedullary |  | CEBPA, MEFV, GATA2 |
| 633734 | after HCT | M1 | 53 | poor | MUD | CR2 | 588 | extramedullary |  | LRP1B, SLC12A3, U2AF1, BCOR |
| 866660 | after HCT | M2 | 41 | intermediate | MMUD (8/10) | CR1 | 632 | extramedullary |  | GATA2, RAD21, CEBPA, NRAS |
| 126620 | after chemo | M4 | 51 | intermediate | — | — | 84 | bone marrow |  | MAP1B, WT1, KRAS |
| 174556 | after chemo | M1 | 65 | poor | — | — | 90 | bone marrow |  | IDH1, EZH2, RUNX1, LRP1B, PTP11 |
| 183696 | after chemo | M2 | 62 | intermediate | — | — | 300 | bone marrow |  | IDH1, NRAS |
| 196371 | after chemo | M4 | 42 | intermediate | — | — | 155 | bone marrow | yes | NPM1, FLT3-TKD |
| 220882 | after chemo | M2 | 71 | intermediate | — | — | 241 | bone marrow | yes | DNMT3A, IDH2, NRAS |
| 275291 | after chemo | M4 | 54 | good | — | — | 278 | bone marrow |  | INV(16), FLT3-TKD |
| 286032 | after chemo | M2 | 50 | intermediate | — | — | 326 | bone marrow |  | DNMT3A, FLT3-ITD, NPM2, ZNF687 |
| 467522 | after chemo | M4 | 69 | poor | — | — | 74 | bone marrow |  | TET2,/SRSF2 |
| 554023 | after chemo | M1 | 71 | poor | — | — | 136 | bone marrow |  | DNMT3A, IDH2, RUNX1, SRSF2 |
| 695558 | after chemo | M2 | 46 | good | — | — | 345 | bone marrow |  | t(8;21) |
| 763312 | after chemo | M2 | 58 | good | — | — | 296 | bone marrow |  | t(8;21), JAK2, DNAH5, GATA2 |
| 823477 | after chemo | M0 | 51 | intermediate | — | — | 249 | bone marrow |  | U2AF1, JAK2 |
| 875663 | after chemo | M4 | 68 | intermediate | — | — | 356 | bone marrow |  | DNMT3A, TET2, SF3B1, NPM1, FLT3-TKD, NRAS, SRSF2 |
| 970171 | after chemo | M2 | 73 | poor | — | — | 132 | bone marrow |  | TP53 |
| 150288 | after chemo | M1 | 51 | intermediate | — | — | 423 | bone marrow | yes | STAG2, PTPN11, NPM1 |
| 303642 | after chemo | M1 | 54 | intermediate | — | — | 1230 | bone marrow | yes | IDH1, GRIK2, FLT3-TKD, WT1, STAG2 |
| 112200 | after chemo | M4 | 43 | good | — | — | 865 | extramedullary | yes | XIRP, NRAS |
| 327733 | after chemo | M1 | 32 | intermediate | — | — | 363 | extramedullary | yes | IDH1, NPM1, FLT3-ITD |
| 593890 | after chemo | M2 | 35 | intermediate | — | — | 445 | extramedullary | yes | CEBPA, MEFV, GATA2 |
| 452198 | after chemo | M4 | 55 | intermediate | — | — | 505 | bone marrow | yes | DNMT3A, NPM1, FLT3-ITD, IDH1, FOXP1, PTPN11 |

HCT, Hematopoietic Cell Transplantation; MUD, matched unrelated donor; SIB, matched sibling donor; MMUD, mismatched unrelated donor; CR, complete remission; PD, persistent disease.

Four of the patients with a post-transplantation relapse had had a post-chemotherapy relapse before they had undergone transplantation, and samples that had been obtained at the time of the post-chemotherapy relapse were also sequenced. For comparison, 20 patients were evaluated who had a relapse after chemotherapy alone. Among the patients in the two groups, there was a typical range in clinical variables, including donor type, time to relapse, and the use of immunosuppression at the time of relapse (see e.g., TABLE 3 and Christopher et al. (2018) Immune Escape of Relapsed AML Cells after Allogeneic Transplantation N Engl J Med 379; 24 2330-2341 for per-sample table containing information on disease characteristics and treatment history, incorporated herein by reference).

Figure 5:
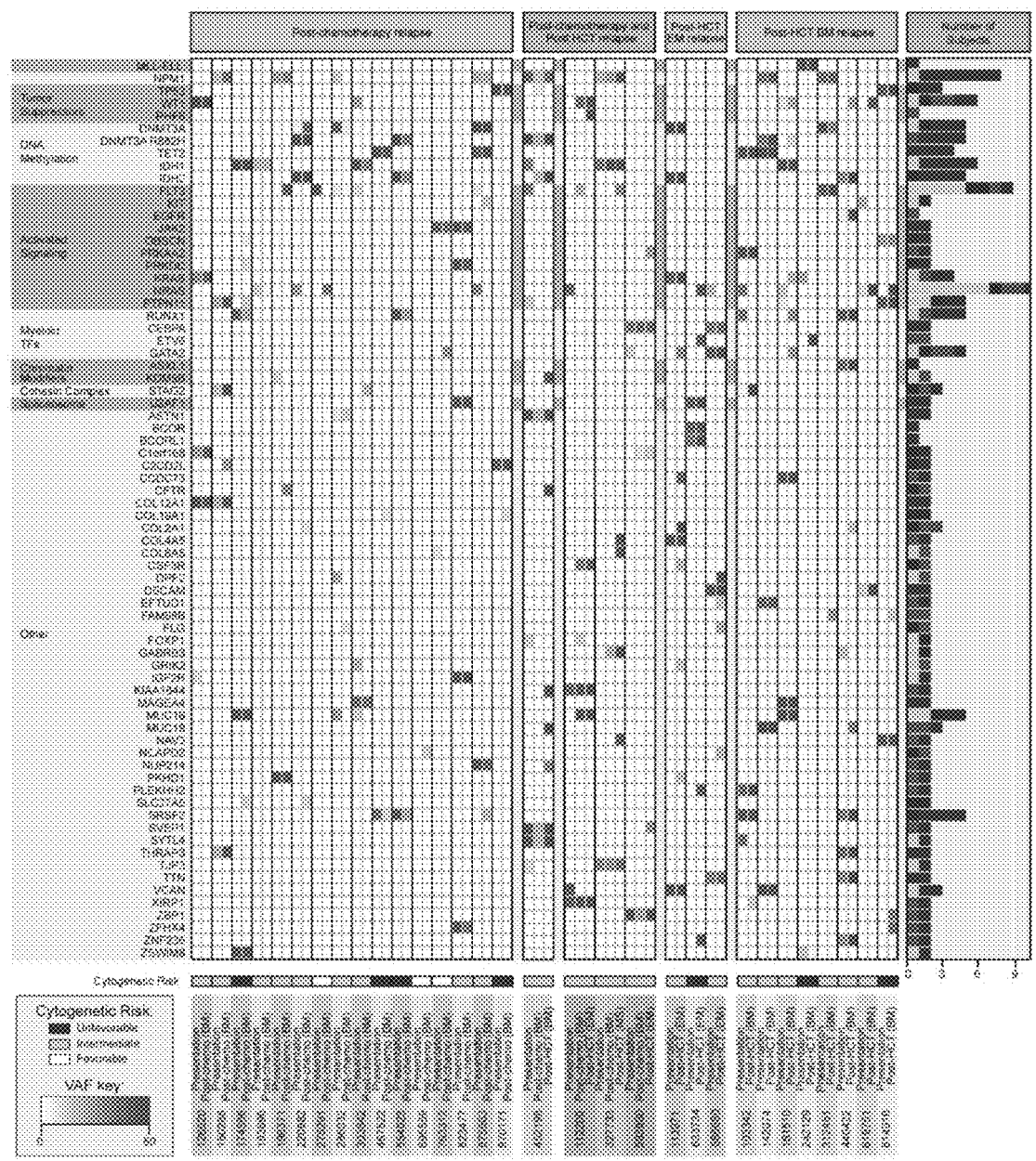
FIG. 5 is a heat map showing mutational spectrum of AML relapsing after chemotherapy vs. transplant. Somatic mutations occurring in at least two samples are shown. Each column represents paired presentation/relapse samples and are grouped by the type of relapse (post-chemo, post-hematopoietic stem cell transplant (HCT) bone marrow, or post-transplant myeloid sarcoma (i.e., extramedullary relapse). Histograms on the right reflect the number of unique patients in whom each gene is mutated in this sample set, as well as when the mutation was detected (presentation sample, post-chemo relapse, post-transplant bone marrow [BM] relapse, post-transplant extramedullary [EM] relapse). Mutations are coded as being detected in the presentation sample (light blue), relapse post-chemo sample (black), relapse post-transplant sample (red), or shared in the presentation and relapse samples (dark blue).

FIG. 5 shows the status of 82 genes that were mutated in at least two samples from either group. Although more than 250 genes were mutated exclusively in patients with a post-transplantation relapse, only 2 genes (ETV6 and FAM98B) were mutated in more than one patient, and each of these 2 genes was mutated in only two patients.

All exome variants were discovered by enhanced exome sequencing of diagnosis and relapse samples from post-transplant and post-chemotherapy relapse groups (data not shown, see Christopher et al. (2018) N Engl J Med 379; 24 2330-2341, incorporated herein by reference). Thus, no driver mutations were commonly associated with relapse after transplantation among these patients, with the caveat that the sample would allow for detection of only a previously unknown relapse-specific driver mutation with a true prevalence of at least 50% among all patients with a post-transplantation relapse. In general, the recurrent mutations that were found at relapse after transplantation were similar to the mutations that were found at initial presentation and at relapse after chemotherapy, and no relapse-specific mutation patterns were observed.

Analysis for Somatic Mutations and Structural Variants in Immune-Related Genes

Figure 6:
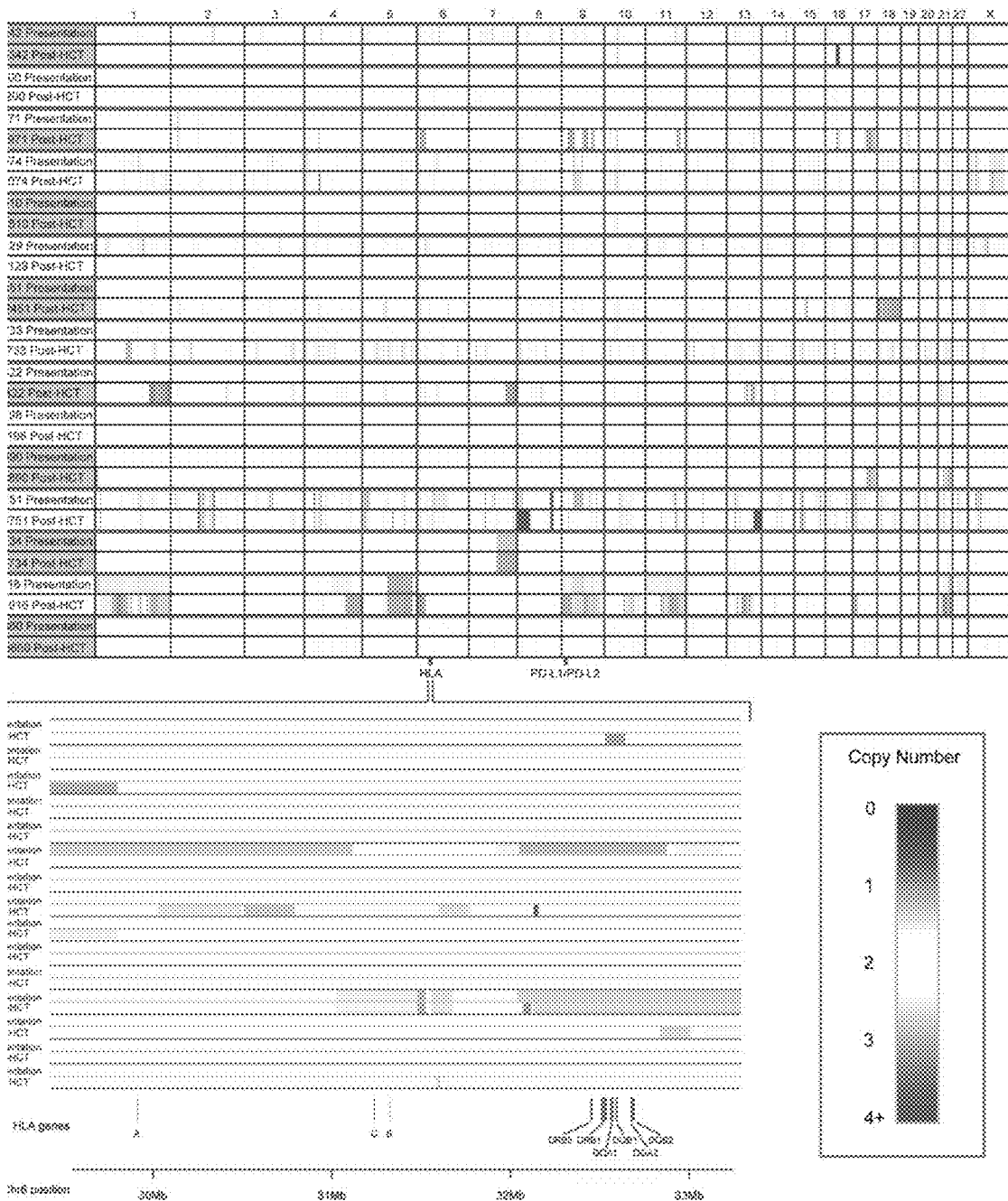
FIG. 6 is a heat map showing copy number alterations in post-transplant cases. Copy number changes in matched presentation and post-hematopoietic stem cell transplant (post-transplant) relapse samples across the entire genome, by chromosome. Red indicates amplification, blue indicates deletion, and white indicates copy number neutral regions. The inset shows the MHC locus on chromosome 6p21.3. The region encompassing PD-L1 and PD-L2 on chromosome 9p24 is also indicated.
Figure 7:
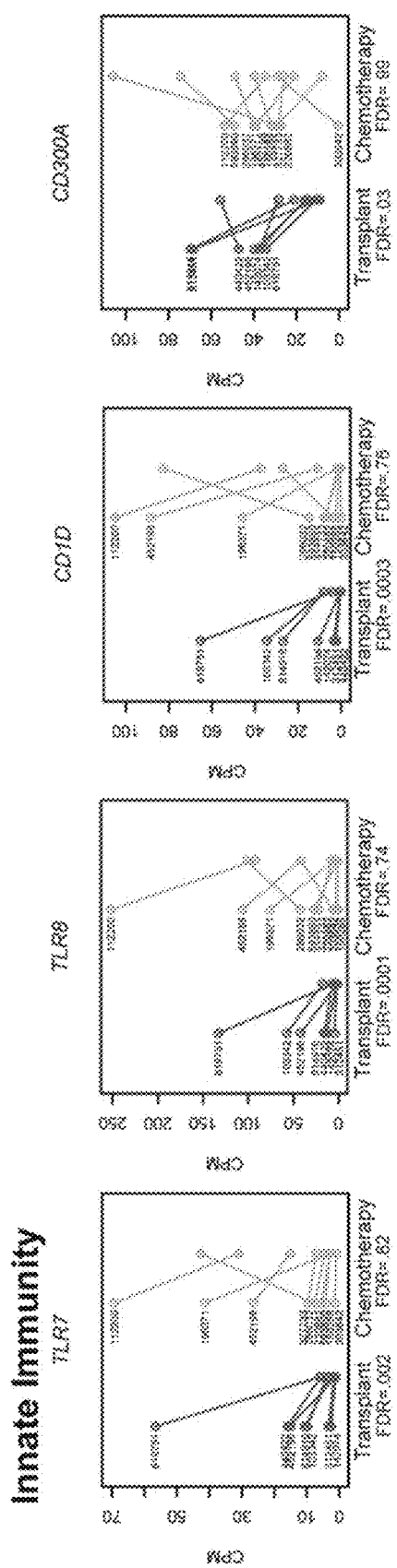
FIG. 7 shows dysregulated gene expression in AML cells after relapse. RNA sequencing was performed on enriched leukemia blast cells from matched presentation and relapse samples, and differentially expressed genes were identified in post-transplant relapse compared to matched presentation samples based using statistically defined methods. Shown are line plots of representative genes from different functional categories.

Given the importance of the graft-versus-leukemia effect in the clearance of AML cells, it is presently thought that AML cells that recur after transplantation may have mutations that lead to immune escape. Among the 15 patients with a post-transplantation relapse, no relapse-specific mutations were found in genes involved in antigen presentation, cytokine signaling, or immune-checkpoint modulation. Gene amplifications in PDL1 and PDL2 have been implicated in immune escape in Hodgkin's lymphoma. In this study, only 1 of the 15 patients (Patient 814916) had an amplification in this region (see e.g., FIG. 6), a finding that suggests that this is not a common mechanism of immune escape in AML after transplantation. A list of all copy number changes in presentation (primary) and post-relapse cases can be found in Christopher et al. (2018) N Engl J Med 379; 24 2330-2341, incorporated herein by reference.

No recurrent, relapse-specific structural variants were found in any region of the relapse genomes. Also, no relapse-specific gene-fusion events were identified; specifically, no fusions involving the MHC class II regulatory gene CIITA were found (see e.g., TABLE 4).

expression in relapse samples, as compared with presentation samples. Among the patients with a post-chemotherapy relapse, there were only 8 genes with a change in expression that met the pre-specified cutoff for significance (false discovery rate, <0.05) (see e.g., TABLE 5 and Christopher et al. (2018) Immune Escape of Relapsed AML Cells after Allogeneic Transplantation N Engl J Med 379; 24 2330-2341 for normalized RNA sequencing data from 7 post-transplant relapse and 9 post-chemo relapse cases expressed as total reads per gene, incorporated herein by reference).

TABLE 4

Fusion transcripts detected by RNA-sequencing in presentation (primary) and post-relapse cases.

| Sample | 5' gene | 3' gene | Reciprocal | Splicings |
|---|---|---|---|---|
| 112200_primary | RPL3 | MPO | N | RPL3>>MPO(Inter_Chromosomal Canonical 1); |
| 112200_post_chemo_relapse | RPL3 | MPO | N | RPL3>>MPO(Inter_Chromosomal Canonical 1); |
| 112200_post_chemo_relapse | CBFB | MYH11 | N | CBFB>>MYH11(Intra_Chromosomal Canonical 6); CBFB>>MYH11(Intra_Chromosomal 18); |
| 161510_primary | SMURF2P1 | LRRC37B | N | SMURF2P1>>LRRC37B(Intra_Chromosomal Canonical 4); |
| 161510_post_allo_relapse | SMURF2P1 | LRRC37B | N | SMURF2P1>>LRRC37B(Intra_Chromosomal Canonical 4); |
| 161510_primary | HLA-H | HLA-B | N | HLA-H>>HLA-B(Intra_Chromosomal Canonical 1); |
| 161510_post_allo_relapse | HLA-H | HLA-B | N | HLA-H>>HLA-B(Intra_Chromosomal Canonical 1); |
| 619751_post_allo_relapse | CBFB | MYH11 | N | CBFB>>MYH11(Intra_Chromosomal Canonical 35); CBFB>>MYH11(Intra_Chromosomal Canonical 1); |
| 619751_primary | CBFB | MYH11 | N | CBFB>>MYH11(Intra_Chromosomal Canonical 16); |
| 814916_primary | U2AF1 | RUNX1 | N | U2AF1>>RUNX1(Intra_Chromosomal Canonical 6); |
| 814916_post_allo_relapse | U2AF1 | RUNX1 | N | U2AF1>>RUNX1(Intra_Chromosomal Canonical 6); |
| 814916_primary | ZNF510 | ZNF782 | N | ZNF510>>ZNF782(Intra_Chromosomal Canonical 1); |
| 814916_post_allo_relapse | ZNF510 | ZNF782 | N | ZN510>>ZNF782(Intra_Chromosomal Canonical 1); |

In a previous study involving patients who had a relapse of AML after receiving a transplant from a haploidentical donor, loss of the mismatched HLA locus was identified in 5 of 17 patients. In this study, only 1 of the 15 patients (Patient 113971) had a deletion at this locus (see e.g., FIG. 6), and the deletion did not involve a coding region. None of the 3 patients who had received a transplant from an HLA-mismatched unrelated donor (Patients 312451, 440422, and 866660) had detectable deletions or mutations in mismatched HLA genes. In addition, analysis of single-nucleotide polymorphisms revealed no evidence of a copy-neutral loss of heterozygosity (i.e., uniparental disomy) in this region for any patient.

Analysis for Changes in Expression of Immune-Related Genes

Since mutations in known immune-related genes were not observed in AML relapse after transplantation, it is presently thought that epigenetic changes in AML cells might have a role in disease progression. Therefore, total RNA sequencing was performed on enriched AML blasts from paired samples obtained at initial presentation and at relapse from seven patients with a post-transplantation relapse and from nine patients with a post-chemotherapy relapse who had adequate cryopreserved material for flow-sorting. In each group, genes were identified that had significantly altered

TABLE 5

Differentially regulated genes.

| Gene | P Value | FDR | Fold Change |
|---|---|---|---|
| ADAMTS14 | 2.75E−08 | 3.97E−05 | 4.8 |
| AEBP1 | 0.00016 | 0.017967 | 4.0 |
| AMOTL1 | 2.18E−06 | 0.00088 | 2.8 |
| ANKRD10 | 0.00055 | 0.042628 | 3.8 |
| AR | 0.000299 | 0.028435 | 3.6 |
| CCDC14 | 0.000146 | 0.017047 | 4.1 |
| CEP70 | 1.48E−05 | 0.003361 | 2.6 |
| CPA3 | 0.000266 | 0.026583 | 4.1 |
| DNAJC12 | 0.000522 | 0.041594 | 2.6 |
| DPY19L2P1 | 0.000238 | 0.024298 | 2.8 |
| ESYT3 | 3.29E−05 | 0.006226 | 5.3 |
| FERMT1 | 4.27E−05 | 0.007454 | 4.1 |
| HPGDS | 0.000489 | 0.041204 | 4.8 |
| HSPD1P11 | 9.78E−05 | 0.013399 | 2.9 |
| LAPTM4B | 9.93E−05 | 0.013488 | 3.3 |
| MARCKSL1 | 1.10E−06 | 0.000548 | 3.3 |
| MDFI | 3.93E−05 | 0.007179 | 2.6 |
| MEX3A | 5.27E−07 | 0.00028 | 3.8 |
| MRC2 | 0.000231 | 0.023891 | 3.5 |
| PLXNB1 | 0.000112 | 0.014715 | 2.6 |
| RAB38 | 2.36E−06 | 0.000915 | 1.9 |
| RP11-299L17.1 | 0.00015 | 0.017231 | 2.7 |

TABLE 5-continued

Differentially regulated genes.

| Gene | P Value | FDR | Fold Change |
|---|---|---|---|
| RYR3 | 0.000145 | 0.017047 | 3.8 |
| SOCS2 | 0.000177 | 0.019424 | 2.2 |
| SPIN4 | 1.71E-05 | 0.003622 | 2.9 |
| STON2 | 3.21E-05 | 0.006147 | 2.8 |
| TMPRSS11D | 5.66E-06 | 0.001661 | 2.7 |
| TPSD1 | 0.000388 | 0.034448 | 4.8 |
| TRGC1 | 7.54E-05 | 0.011098 | 2.6 |
| TRGJP1 | 0.000132 | 0.01618 | 5.4 |
| TRGJP2 | 4.38E-05 | 0.007571 | 3.5 |
| UNGP3 | 7.50E-05 | 0.011098 | 2.7 |
| WASF1 | 0.000227 | 0.023631 | 1.9 |
| ZBTB10 | 0.000544 | 0.042432 | 1.9 |
| MARCH1 | 0.000146 | 0.017047 | -2.3 |
| ABI3 | 5.98E-06 | 0.001696 | -5.0 |
| AC010970.2 | 3.82E-08 | 4.05E-05 | -4.2 |
| ACPP | 0.000526 | 0.041594 | -2.9 |
| ADAMTS4 | 0.000151 | 0.017265 | -2.2 |
| ADAP2 | 2.53E-05 | 0.005115 | -3.8 |
| ADM | 0.000504 | 0.041323 | -3.1 |
| AL5131221 | 5.11E-05 | 0.008372 | -21.1 |
| ALOX5 | 0.000507 | 0.041376 | -3.2 |
| ANXA5 | 7.12E-06 | 0.001951 | -8.3 |
| AP5B1 | 0.000553 | 0.04267 | -2.0 |
| APOBR | 1.68E-05 | 0.003622 | -3.4 |
| ARHGAP6 | 0.000105 | 0.01406 | -5.2 |
| ARHGEF10L | 2.80E-07 | 0.000171 | -27.0 |
| BCL6 | 0.000514 | 0.041594 | -4.7 |
| C10orf105 | 0.000258 | 0.025934 | -5.0 |
| C10orf54 | 0.000126 | 0.015956 | -2.7 |
| C1orf162 | 1.69E-05 | 0.003622 | -2.6 |
| CADM1 | 2.21E-06 | 0.00088 | -3.2 |
| CAPG | 0.000521 | 0.041594 | -2.0 |
| CCDC170 | 0.000536 | 0.042002 | -3.2 |
| CCL5 | 8.57E-05 | 0.012497 | -3.1 |
| CCR1 | 2.75E-06 | 0.001032 | -5.6 |
| CCR2 | 1.64E-10 | 1.23E-06 | -9.1 |
| CCR5 | 3.12E-06 | 0.001129 | -7.2 |
| CD14 | 1.07E-07 | 8.92E-05 | -14.0 |
| CD1D | 5.79E-07 | 0.000297 | -8.5 |
| CD28 | 4.14E-05 | 0.007454 | -5.4 |
| CD300A | 0.000329 | 0.030795 | -2.4 |
| CD300C | 1.39E-05 | 0.003213 | -4.6 |
| CD300E | 3.45E-12 | 5.49E-08 | -28.1 |
| CD300LB | 8.53E-09 | 2.11E-05 | -8.2 |
| CD36 | 9.06E-05 | 0.012867 | -4.2 |
| CD48 | 0.00063 | 0.046144 | -2.8 |
| CD52 | 1.14E-05 | 0.002883 | -2.8 |
| CD68 | 0.00017 | 0.01878 | -2.8 |
| CD74 | 0.000193 | 0.020591 | -3.2 |
| CD86 | 3.10E-05 | 0.006004 | -6.0 |
| CHST15 | 8.90E-05 | 0.012764 | -5.3 |
| CNTNAP2 | 0.000225 | 0.023631 | -3.7 |
| COL6A3 | 0.000116 | 0.014996 | -3.4 |
| CORO1A | 0.000111 | 0.014699 | -2.2 |
| CR1 | 0.000393 | 0.034541 | -4.1 |
| CRTAM | 5.30E-05 | 0.008594 | -3.0 |
| CSF2RA | 0.000131 | 0.01618 | -2.6 |
| CTSS | 2.08E-06 | 0.000871 | -2.8 |
| CX3CR1 | 2.67E-07 | 0.00017 | -12.0 |
| DTX4 | 0.000131 | 0.01618 | -4.5 |
| EDA | 0.000252 | 0.025473 | -2.4 |
| EEF1DP3 | 0.000212 | 0.022506 | -3.1 |
| F13A1 | 5.67E-05 | 0.009009 | -3.9 |
| FAM198B | 4.87E-06 | 0.001581 | -6.3 |
| FAM65B | 0.000276 | 0.027017 | -2.1 |
| FCER1G | 3.67E-06 | 0.00124 | -4.4 |
| FCER2 | 4.81E-08 | 4.78E-05 | -7.0 |
| FCGR3A | 4.92E-05 | 0.008231 | -6.1 |
| FGD2 | 1.98E-07 | 0.000137 | -5.4 |
| FGL2 | 1.36E-06 | 0.000103 | -7.5 |
| FGR | 5.65E-06 | 0.001661 | -6.9 |
| FPR1 | 0.000292 | 0.028114 | -3.6 |
| FYB | 0.000143 | 0.017047 | -2.0 |
| GIMAP1 | 4.71E-05 | 0.007969 | -3.2 |
| GIMAP4 | 2.47E-07 | 0.000163 | -6.2 |
| GIMAP7 | 0.000605 | 0.045141 | -3.8 |
| GIMAP8 | 0.000121 | 0.015408 | -4.2 |
| GLT1D1 | 0.000556 | 0.042726 | -10.8 |
| GPAT3 | 3.23E-08 | 4.05E-05 | -4.0 |
| GRM2 | 0.000417 | 0.036016 | -2.3 |
| GRN | 0.000132 | 0.01618 | -2.6 |
| GSG1L | 5.73E-09 | 1.82E-05 | -7.7 |
| HAVCR2 | 0.0005 | 0.041323 | -2.4 |
| HCK | 3.30E-06 | 0.001167 | -3.9 |
| HDAC9 | 1.41E-06 | 0.00066 | -3.0 |
| HK3 | 1.58E-05 | 0.003531 | -16.6 |
| HLA-DMA | 0.000611 | 0.045362 | -2.4 |
| HLA-DMB | 4.64E-06 | 0.001538 | -5.4 |
| HLA-DPA1 | 7.28E-05 | 0.011018 | -5.0 |
| HLA-DPB1 | 5.09E-05 | 0.008372 | -3.8 |
| HLA-DQB1 | 0.000189 | 0.020407 | -4.1 |
| HLA-DRB1 | 7.41E-05 | 0.011098 | -4.5 |
| HLA-F | 0.000572 | 0.043529 | -2.5 |
| HMOX1 | 3.35E-05 | 0.006267 | -4.2 |
| HSPA6 | 0.00016 | 0.017967 | -4.7 |
| HSPA7 | 0.000599 | 0.044941 | -8.9 |
| IFI30 | 1.99E-08 | 3.16E-05 | -8.8 |
| IGHA2 | 9.37E-05 | 0.013062 | -4.9 |
| IGHG2 | 5.15E-10 | 2.05E-06 | -12.0 |
| IGHG4 | 2.54E-06 | 0.005115 | -10.8 |
| IGKV2-28 | 2.75E-05 | 0.005462 | -10.6 |
| IGSF6 | 3.73E-05 | 0.006901 | -3.4 |
| IL16 | 0.000326 | 0.030687 | -1.9 |
| IPCEF1 | 0.000448 | 0.038294 | -5.2 |
| IRF8 | 0.000148 | 0.01717 | -3.4 |
| ITGAL | 6.84E-08 | 6.40E-05 | -3. |
| ITGAX | 1.32E-05 | 0.003109 | -4.1 |
| ITGB2 | 0.000495 | 0.041323 | -2. |
| ITGB7 | 0.000361 | 0.032787 | -2.0 |
| JAML | 1.33E-05 | 0.003109 | -8.3 |
| KCNA3 | 8.16E-06 | 0.002161 | -4.0 |
| KCTD12 | 2.79E-06 | 0.001032 | -6.0 |
| KIAA0513 | 4.24E-07 | 0.000233 | -2.9 |
| LGALS2 | 1.49E-08 | 2.81E-05 | -17.1 |
| LGALS3 | 0.000141 | 0.016927 | -6.3 |
| LILRA1 | 3.69E-08 | 4.05E-05 | -8.0 |
| LILRB4 | 9.76E-05 | 0.013399 | -6.6 |
| LRP | 7.11E-06 | 0.001951 | -4.3 |
| LRRC25 | 0.000524 | 0.041594 | -3.4 |
| LRRK2 | 1.08E-05 | 0.002822 | -11.0 |
| LYZ | 1.70E-05 | 0.003622 | -12.4 |
| MAFB | 5.75E-06 | 0.001661 | -15.0 |
| MAST3 | 0.000685 | 0.049309 | -2.4 |
| MEFV | 1.18E-05 | 0.002939 | -2.9 |
| MPEG1 | 1.59E-08 | 2.81E-05 | -8.9 |
| MPP3 | 0.000121 | 0.015408 | -2.8 |
| MYCL | 2.33E-10 | 1.23E-06 | -19.1 |
| MYO1E | 0.000188 | 0.020407 | -4.0 |
| MYO6 | 0.000358 | 0.032738 | -3.1 |
| MYOF | 4.24E-05 | 0.007454 | -7.1 |
| NACC2 | 0.000456 | 0.038794 | -3.7 |
| NAPSB | 1.29E-06 | 0.000622 | -5.6 |
| NCF2 | 0.000277 | 0.027017 | -3.7 |
| NEDD9 | 0.000294 | 0.028166 | -2.5 |
| NFAM1 | 4.98E-06 | 0.001585 | -3.4 |
| NLRC4 | 0.000497 | 0.041323 | -3.2 |
| NLRP1 | 0.00067 | 0.048411 | -2.9 |
| NLRP12 | 1.29E-05 | 0.003109 | -4.3 |
| NRGN | 4.44E-05 | 0.007591 | -5.8 |
| NUAK2 | 0.000621 | 0.045715 | -2.5 |
| P2RY13 | 0.000336 | 0.031248 | -4.7 |
| PDE2A | 6.39E-05 | 0.009864 | -5.1 |
| PECAM1 | 5.67E-06 | 0.001661 | -2.3 |
| PIK3R5 | 0.000226 | 0.023631 | -2.8 |
| PILRA | 0.000388 | 0.034448 | -2.9 |
| PLEKHO2 | 0.000533 | 0.041957 | -1.9 |
| POU2AF1 | 0.000193 | 0.020591 | -2.1 |
| PPBP | 2.16E-05 | 0.00446 | -26.4 |
| PSTPIP1 | 4.26E-05 | 0.007454 | -3.3 |
| PTAFR | 3.58E-06 | 0.001237 | -6.2 |

TABLE 5-continued

Differentially regulated genes.

| Gene | P Value | FDR | Fold Change |
|---|---|---|---|
| PTPRB | 0.000409 | 0.035565 | −2.9 |
| RAB31 | 1.12E−07 | 8.93E−05 | −9.7 |
| RASGRP4 | 0.000281 | 0.027276 | −2.3 |
| RASSF3 | 0.00049 | 0.041204 | −2.0 |
| RBM47 | 8.02E−06 | 0.002161 | −3.8 |
| RGL1 | 1.99E−05 | 0.004166 | −3.5 |
| RNASE6 | 5.37E−05 | 0.008629 | −4.9 |
| RNF144B | 2.82E−05 | 0.005534 | −2.4 |
| RYR1 | 1.33E−0 | 0.003109 | −8.4 |
| S100A11 | 0.000561 | 0.042885 | −2.7 |
| SAMHD1 | 3.38E−08 | 4.05E−05 | −5.8 |
| SELPLG | 1.51E−06 | 0.000687 | −2.2 |
| SERPINA1 | 1.94E−06 | 0.000833 | −11.3 |
| SH2D3C | 0.000421 | 0.036168 | −2.1 |
| SIGLEC9 | 0.000599 | 0.044941 | −4.0 |
| SIRPB2 | 1.77E−06 | 0.000783 | −2.7 |
| SLC11A1 | 0.000596 | 0.044941 | −3.0 |
| SLC12A1 | 7.13E−05 | 0.010907 | −3.1 |
| SLC7A7 | 0.000268 | 0.026654 | −2.9 |
| SLC8A1 | 0.000168 | 0.01868 | −5.1 |
| SORT1 | 8.91E−05 | 0.012764 | −2.6 |
| SPON1 | 0.000652 | 0.047308 | −2.5 |
| STX11 | 0.000234 | 0.024044 | −3.4 |
| SULF2 | 0.00035 | 0.032128 | −2.6 |
| SULT1A4 | 0.000391 | 0.034541 | −3.5 |
| TBC1D2 | 0.000517 | 0.041594 | −2.1 |
| TBC1D9 | 0.000153 | 0.017359 | −7.0 |
| TGFBI | 3.84E−07 | 0.000218 | −7.6 |
| THEMIS2 | 0.000103 | 0.01391 | −2.6 |
| TLR1 | 0.000274 | 0.027009 | −2.0 |
| TLR7 | 5.66E06 | 0.001661 | −4.2 |
| TLR8 | 1.79E−07 | 0.000129 | −7.2 |
| TMEM71 | 0.000504 | 0.041323 | −1.9 |
| TNF | 0.000384 | 0.034448 | −5.3 |
| TNFRSF1B | 6.33E−05 | 0.009864 | −3.3 |
| TNFSF12 | 1.14E−05 | 0.002883 | −5.0 |
| TNFSF13 | 0.00034 | 0.031457 | −2.1 |
| TNFSF8 | 0.000397 | 0.03464 | −2.9 |
| TNNI2 | 0.000639 | 0.046591 | −4.6 |
| TP53I11 | 9.32E−05 | 0.013062 | −3.6 |
| TRPS1 | 0.000321 | 0.030423 | −2.4 |
| TSHZ3 | 2.92E−07 | 0.000172 | −8.0 |
| TTC9 | 0.000369 | 0.033369 | −3.4 |
| TYROBP | 8.50−08 | 7.50E−05 | −2.8 |
| VCAN | 9.31E−09 | 2.11E−05 | −22.4 |
| VIPR1 | 6.11E−05 | 0.009618 | −5.0 |
| VSIG1 | 0.000613 | 0.045362 | −2.5 |
| ZBTB47 | 0.000139 | 0.016829 | −5.5 |
| ZNF366 | 0.000115 | 0.014996 | −2.9 | logFC = log2-fold change of expression between presentation and relapse, logCPM = average log2-counts per million, LR = log ratio statistics.

In contrast, among the patients with a post-transplantation relapse, 34 genes were significantly upregulated and 187 genes were significantly downregulated (see e.g., Christopher et al. (2018) Immune Escape of Relapsed AML Cells after Allogeneic Transplantation N Engl J Med 379; 24 2330-2341, incorporated herein by reference).

An analysis was performed of the pathways of genes with differential expression between presentation and relapse samples from the patients with a post-transplantation relapse. Significantly dysregulated pathways included pathways involving immune-response genes ($p<1\times10^{-35}$ for the enrichment of previously annotated immune-response genes among differentially expressed genes identified in this analysis), as well as pathways involved in cell adhesion and motility and in the innate immune response (see e.g., Christopher et al. (2018) Immune Escape of Relapsed AML Cells after Allogeneic Transplantation N Engl J Med 379; 24 2330-2341 for analysis of differentially regulated gene pathways based on Gene Ontology Consortium categories, incorporated herein by reference).

Of the 30 most highly enriched pathways that involved "biological processes" (as designated by the Gene Ontology Consortium), 3 were related to cell adhesion, 6 to the innate immune response, and 13 to the adaptive immune response (see e.g., FIG. 1A-FIG. 1F, FIG. 7, and FIG. 8A-FIG. 8B).

Although the means by which these dysregulated genes may affect relapse after transplantation is not yet clear, the downregulation of MHC class II genes suggests a plausible mechanism that may contribute to immune escape after transplantation. Four classical MHC class II genes (HLA-DPA1, HLA-DPB1, HLA-DQB1, and HLA-DRB1) were significantly downregulated in six of the seven patients with a post-transplantation relapse. In addition, expression of the HLA-DQA1, HLA-DRB3, and HLA-DRA genes was decreased, but the changes were not significant (see e.g., FIG. 1A-FIG. 1F and FIG. 8A-FIG. 8B). Several other genes involved in antigen processing and presentation by MHC class II molecules (e.g., IFI30, HLA-DMA, HLA-DMB, and CD74) were significantly downregulated in the same six patients, as was the gene encoding the T-cell costimulatory molecule CD86 (also known as B7-2 or CD28 ligand 2) (see e.g., FIG. 1A-FIG. 1F and FIG. 8A-FIG. 8B). The AML cells from one patient (Patient 440422) did not show downregulation in any of these genes, which suggests that other mechanisms of relapse after transplantation must also be relevant for some patients.

Figure 1A:
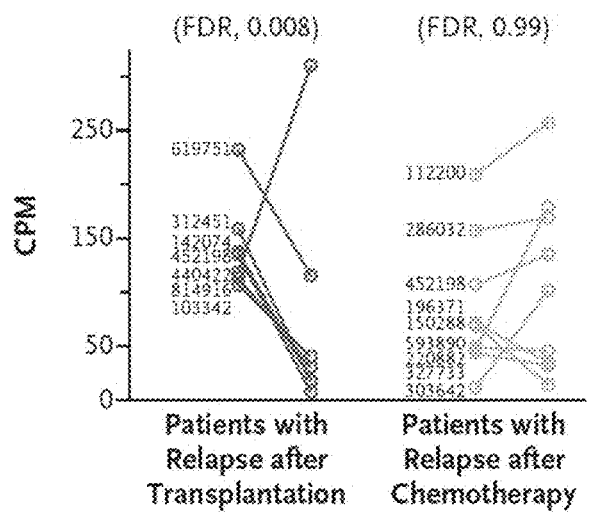
FIG. 1A-FIG. 1F is a series of graphs showing expression of immune-related genes among patients with a relapse of acute myeloid leukemia (AML). RNA sequencing was performed on enriched AML blasts from paired samples obtained at initial presentation and at relapse from patients who had a relapse after transplantation and from patients who had a relapse after chemotherapy. Each panel shows the gene expression in individual patients; the numbers are patient identifiers. The lines show the change in gene expression between the presentation sample (left data point) and the relapse sample (right data point). Among the patients with a post-transplantation relapse, 221 genes showed significant (false discovery rate (FDR), <0.05) differential expression between the presentation and relapse samples. These included genes involved in immune function, such as the major histocompatibility complex (MHC) class II genes (A) HLA-DPB1, (B) HLA-DQB1, and (C) HLA-DRB1, as well as (D) the gene encoding the T cell costimulatory protein CD86 and (E) the gene encoding the MHC class II invariant chain CD74. In four of seven post-transplantation relapse samples, there was also (F) decreased expression of CIITA, a master transcriptional regulator of MHC class II genes; this change was not significant. CPM denotes count per million mapped sequence reads.
Figure 1B:
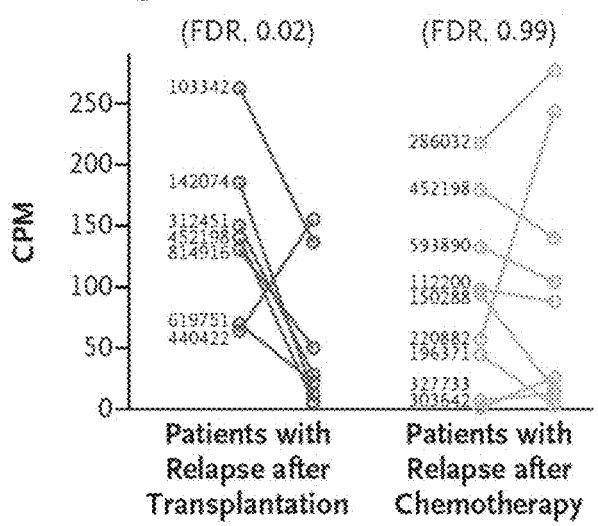
Figure 1C:
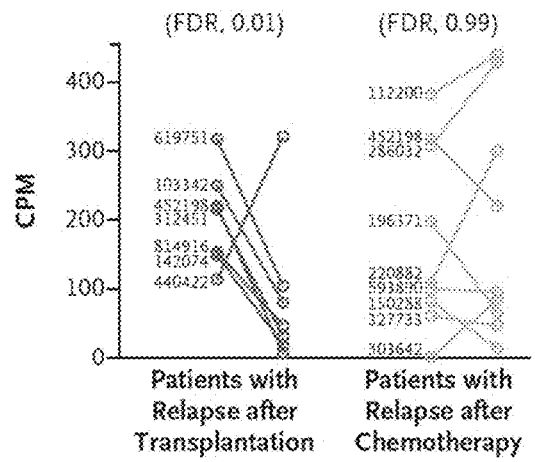
Figure 1D:
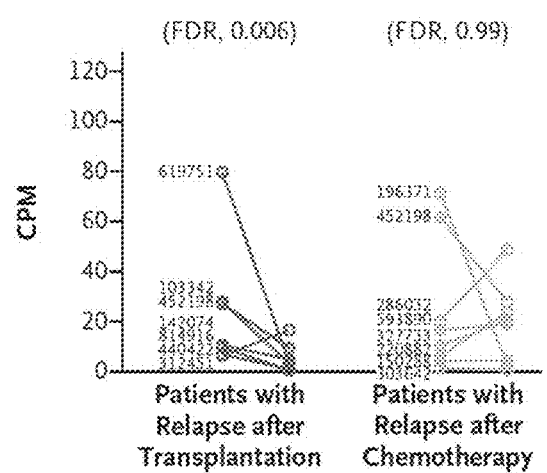
Figure 1E:
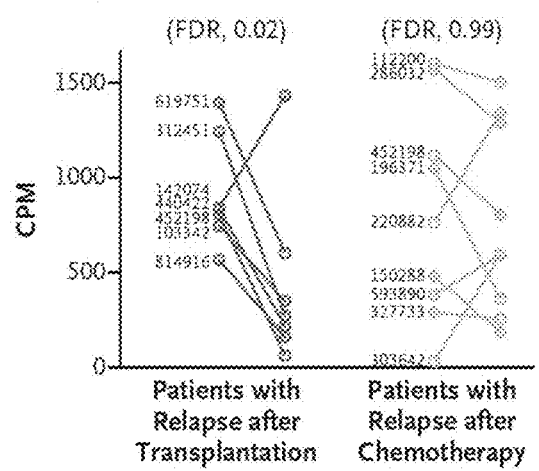
Figure 1F:
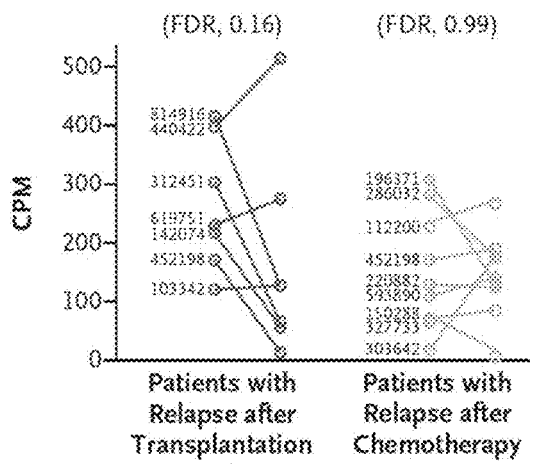
Figure 2A:
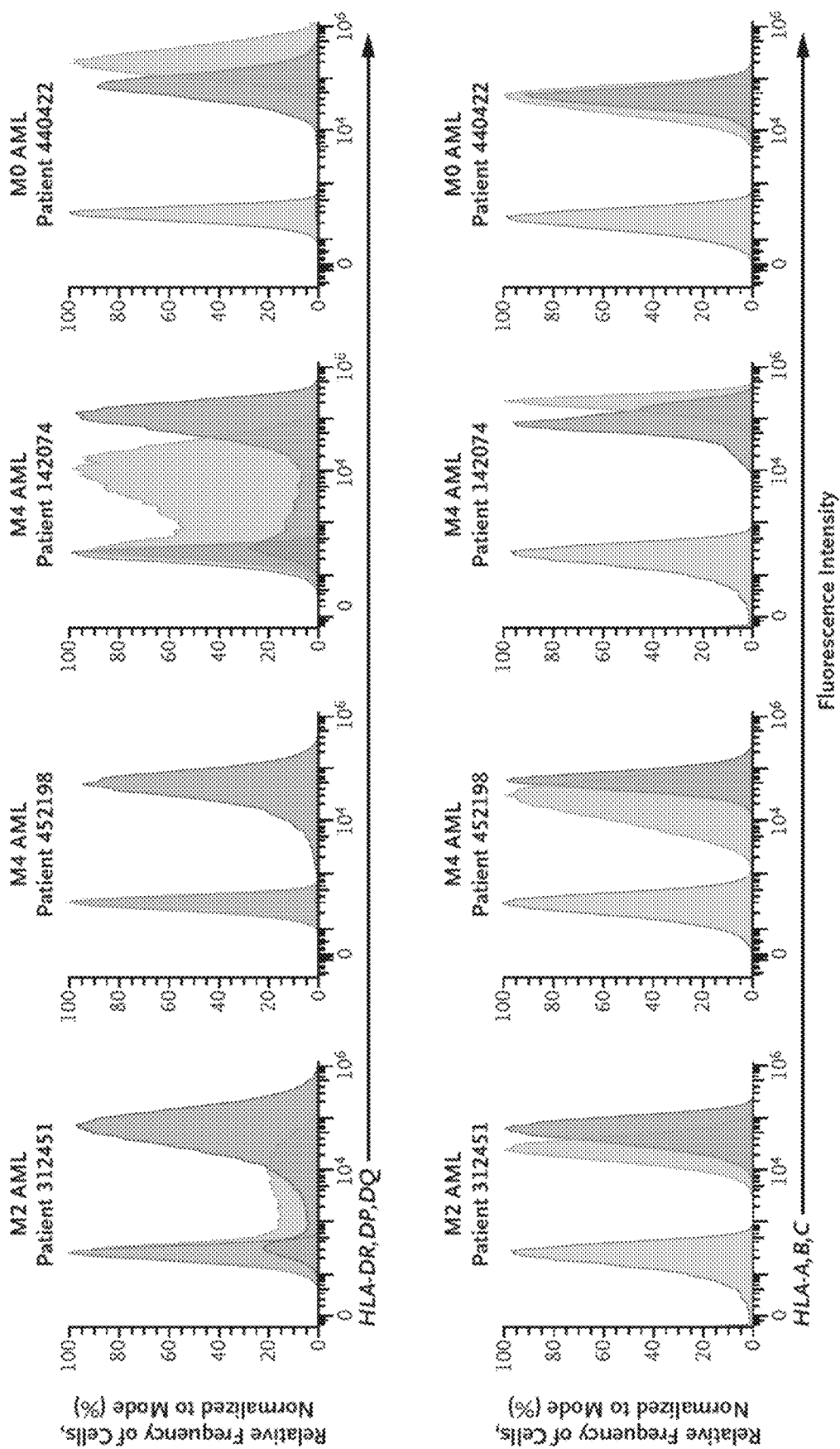
FIG. 2A-FIG. 2B is a series of graphs showing expression of MHC proteins on the surface of AML cells from patients with a relapse after transplantation. (A) To validate the results of RNA sequencing, which showed downregulation of MHC class II genes in some patients with a relapse of AML after transplantation, flow cytometry was performed. Shown is the expression of MHC proteins on AML cells (CD45 dim, side scatter low) in presentation and relapse samples from patients with a post-transplantation relapse, as compared with negative controls. The samples were stained with a fluorescently tagged antibody that recognized MHC class II proteins (HLA-DR, HLA-DP, and HLA-DQ; top row) or an antibody that recognized MHC class I proteins (HLA-A, HLA-B, and HLA-C; bottom row). The sample from Patient 440422 is an example of a case that did not show downregulation of MHC class II at relapse; this finding is consistent with the data from RNA sequencing for this patient. (B) To determine whether the downregulation of MHC class II at relapse was reversible, flow cytometry was performed on samples that were treated with interferon-γ. Shown is the expression of MHC class II proteins on AML cells in relapse samples from patients with a post-transplantation relapse associated with downregulation of MHC class II, as compared with negative controls. The cells were cultured for up to 72 hours in the presence or absence of interferon-γ, and the expression of MHC class II proteins was assessed at different time points. For each patient, the French-American-British classification of AML is shown; a classification of M0 AML indicates AML with minimal differentiation, M2 AML indicates AML with maturation, and M4 AML indicates acute myelomonocytic leukemia.
Figure 9A:
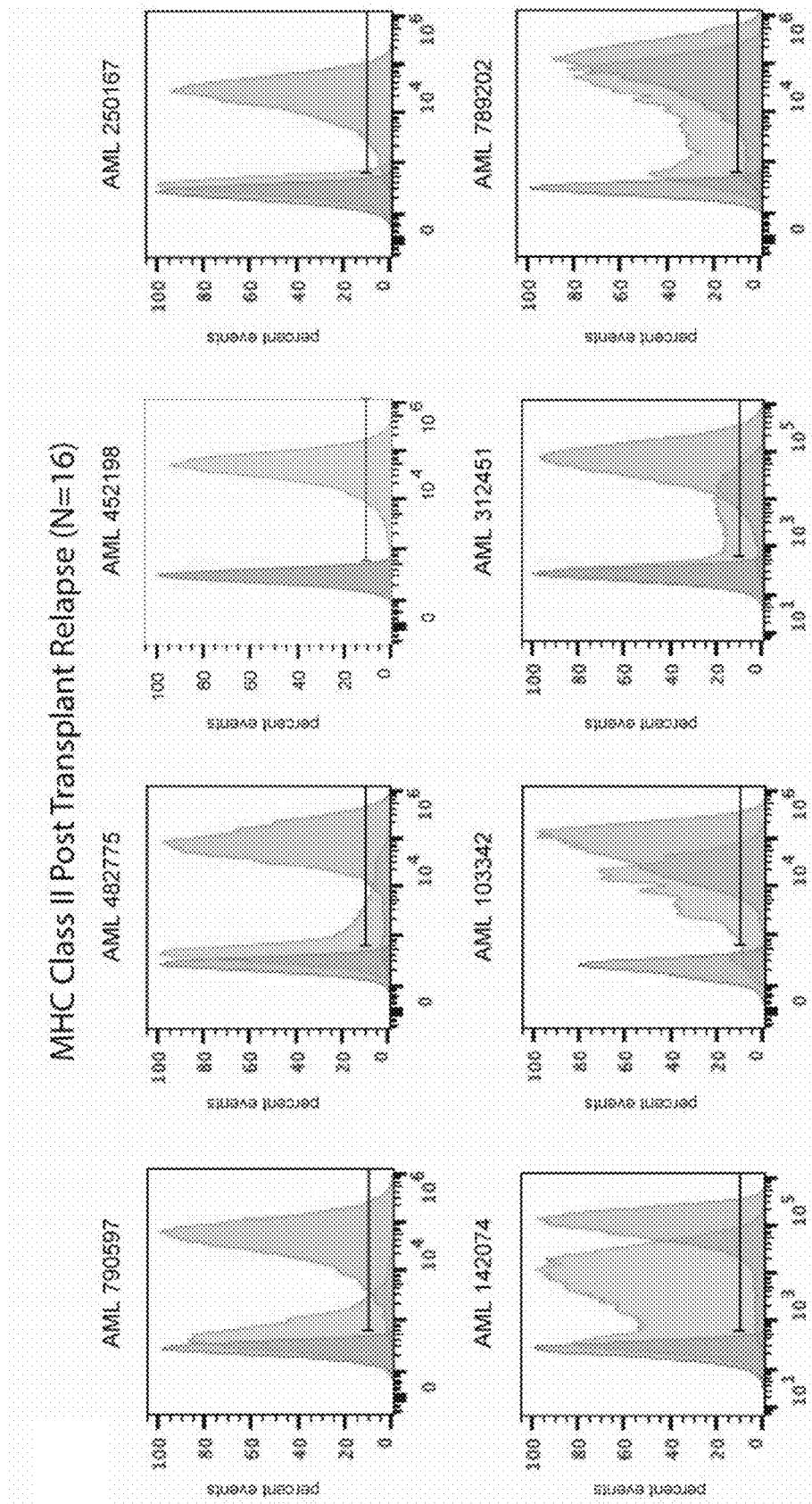
FIG. 9A-FIG. 9B is a series of graphs showing flow cytometry for MHC class II expression post-transplant. Cryopreserved presentation/relapse pairs (N=16) were stained with an antibody against HLA-DP, DQ, or DR (MHC class II). Shown is MHC class II expression on CD45 dim, side scatter low blasts from diagnosis (blue histograms), relapse (orange histogram), and negative control (grey histogram). (A) 8/16 cases show either substantial (>60-fold decrease, AML312451, AML452198, AML250167, AML482775, AML790597) or partial (4-22 fold decrease, AML103342, AML789202, and AML142074) downregulation of MHC class II expression based on mean fluorescence intensity. (B) The remaining 8 cases showed no decrease in MHC class II expression. X axes show fluorescent intensity on a log scale, Y axes are percent events normalized to the modes of each sample. Negative controls represent fluorescence-minus-one controls.
Figure 9B:
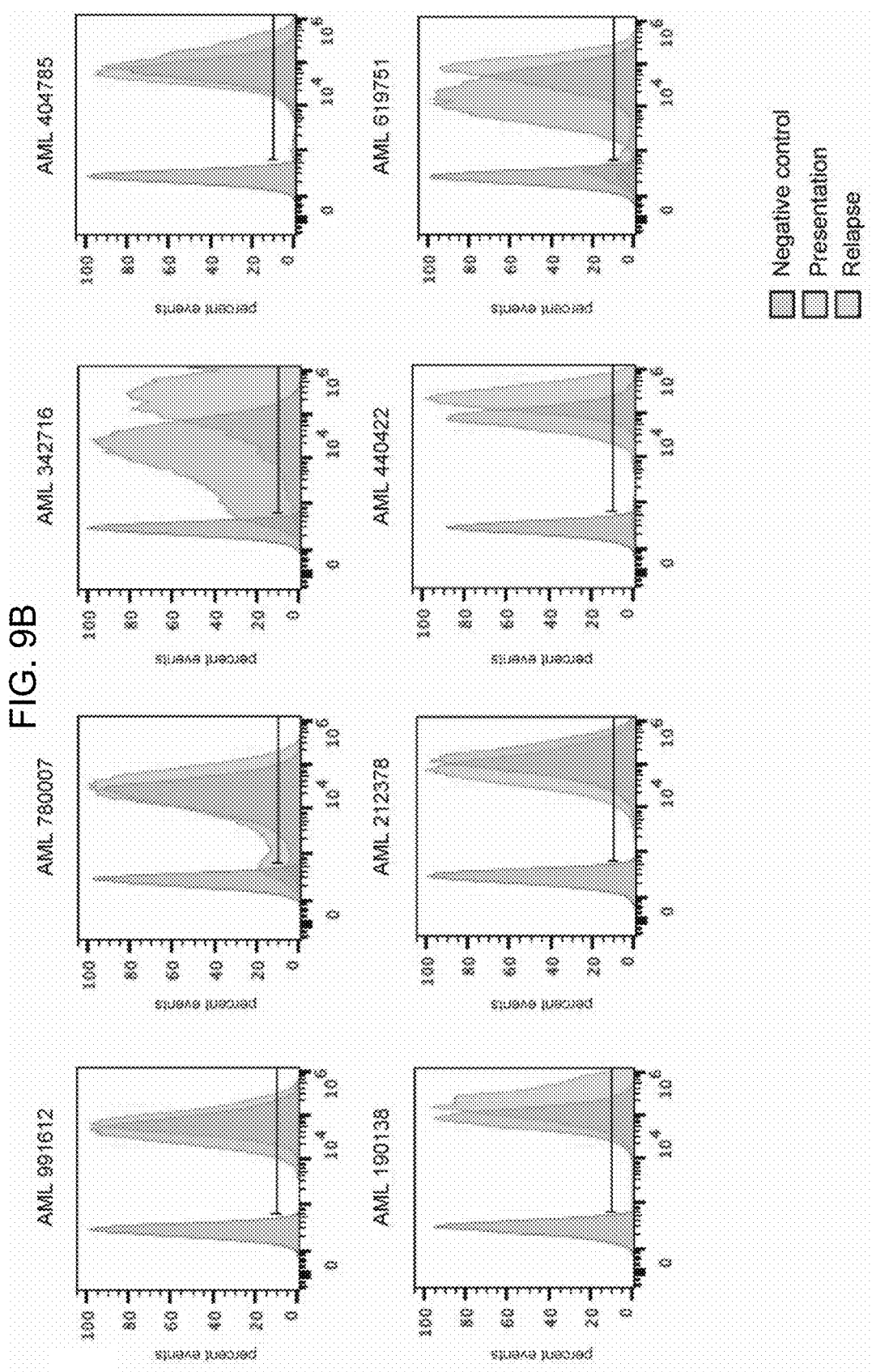

To confirm the downregulation of MHC class II genes at the protein level, flow cytometry was performed on paired presentation and relapse samples from six patients. Samples from all but one patient (Patient 619751) showed concordance between the downregulation of MHC class II genes on RNA sequencing and the results on flow cytometry, which was performed with the use of a pan-specific antibody for HLA-DP, HLA-DQ, and HLA-DR, with gating on the AML blast population (CD45 dim, side scatter low) (see e.g., FIG. 2A and FIG. 9A-FIG. 9B).

Figure 8A:
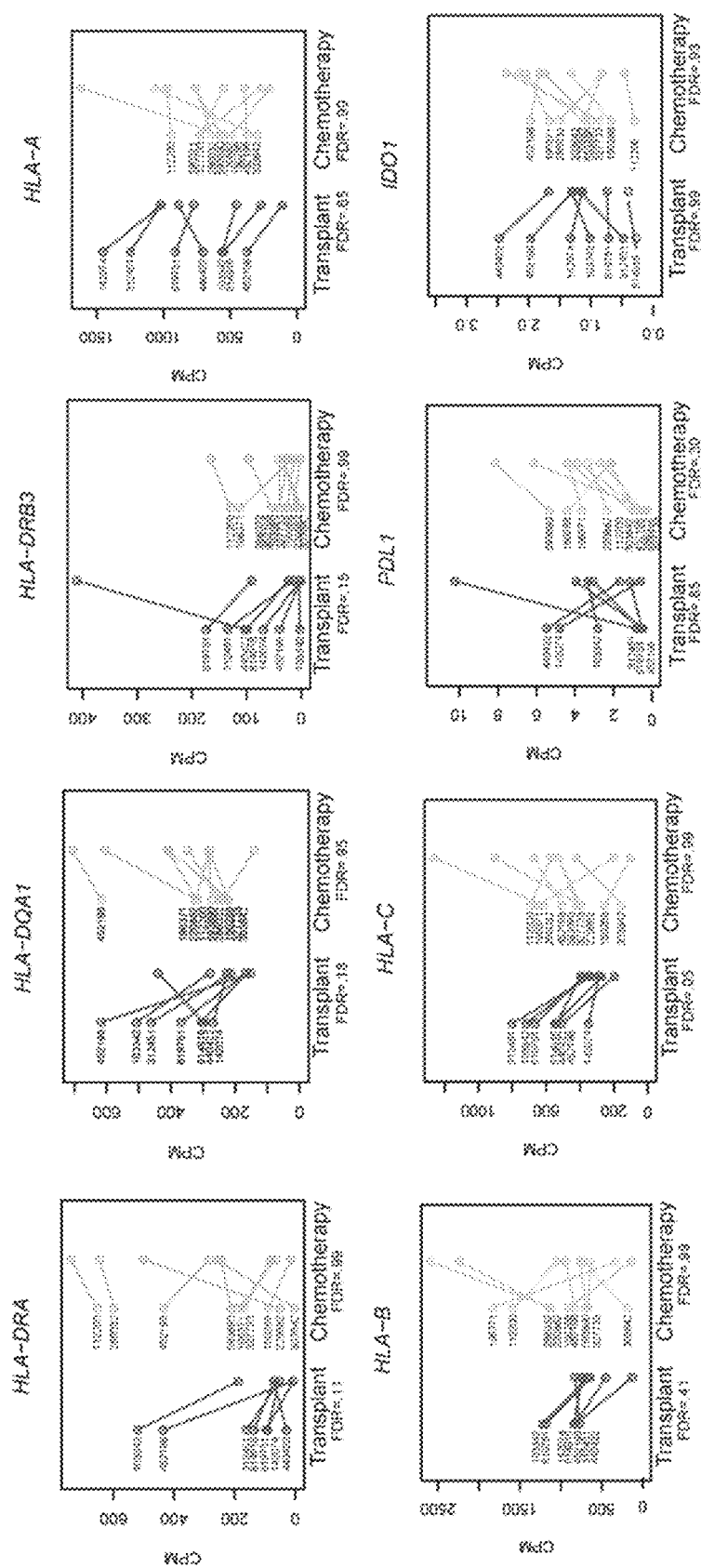
FIG. 8A-FIG. 8B is series of graphs showing expression of immune-related genes in AML cells after transplant. (A) MHC class II genes (HLA-DRA, HLA-DQA1, AND HLA-DRB3), MHC class I genes, and PDL1 and IDO1 expression levels, after presentation vs. post-transplant relapse. (B) MHC class II and MHC class II-related genes HLA-DMA, HLA-DMB, HLA-DPA1, IL16, IFI30, and CTSS were identified as downregulated by predefined criteria in the post-transplant relapse cases, but not in the post-chemotherapy cases.
Figure 8B:
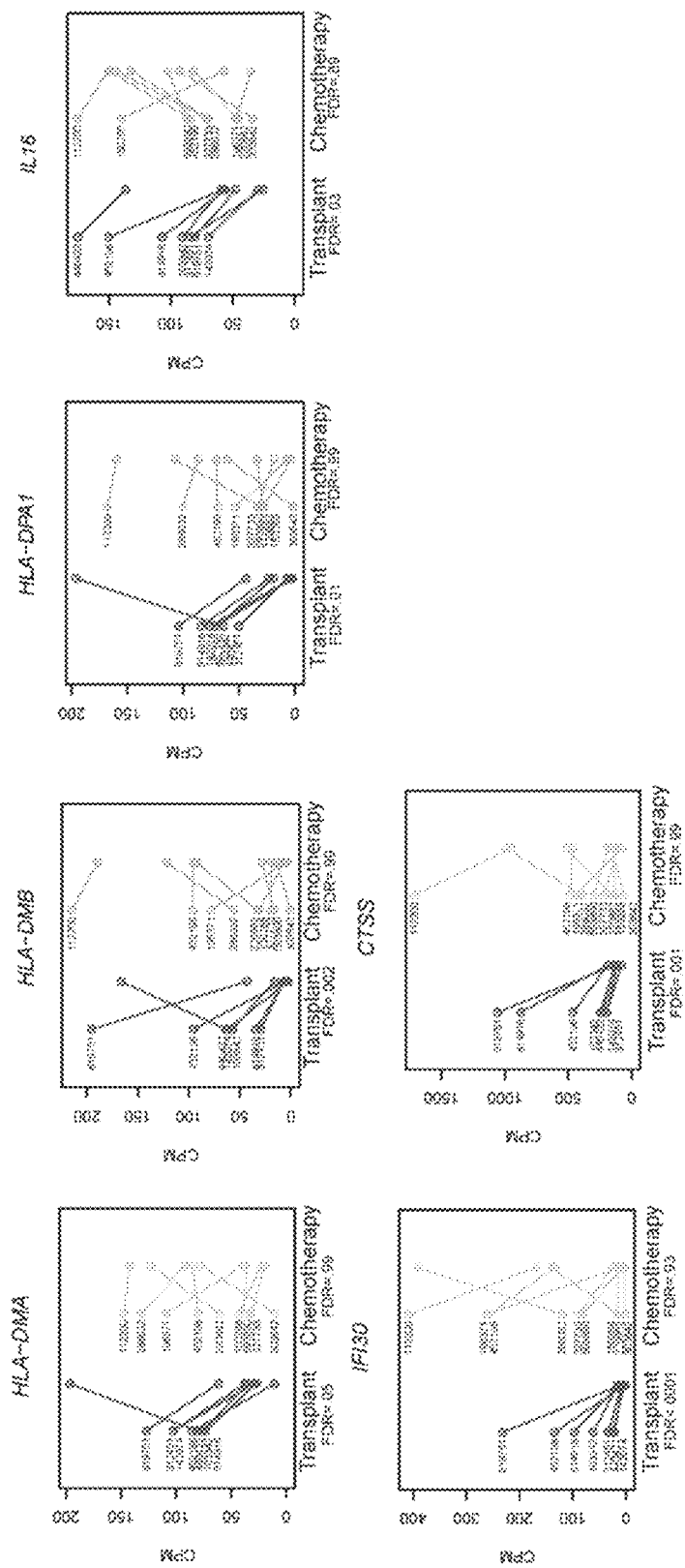
Figure 10:
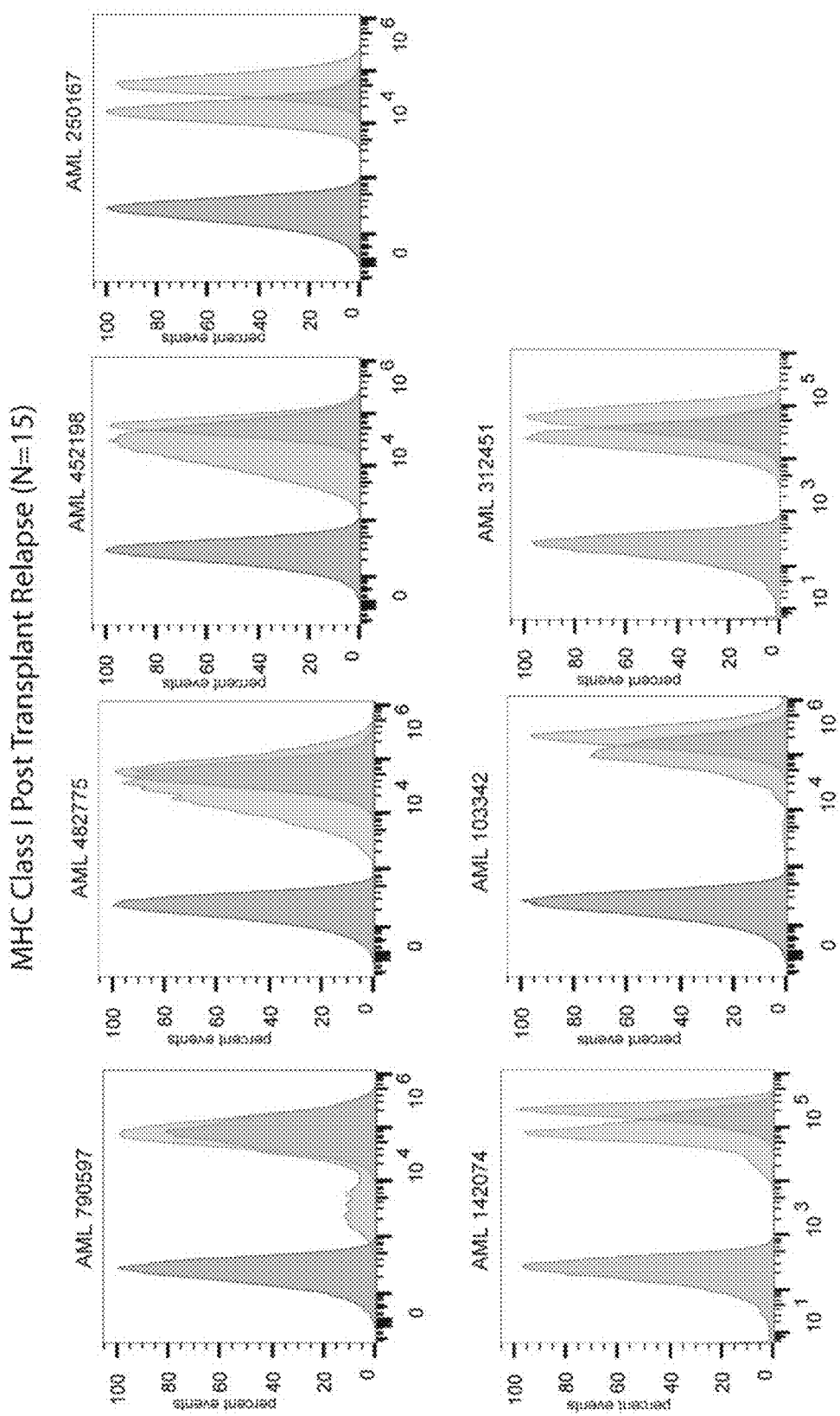
FIG. 10 shows flow cytometry for MHC class I expression post-transplant. Cryopreserved presentation/relapse pairs (N=15) were stained with an antibody against HLA-A, B, or C (MHC class I). Shown is MHC class I expression on CD45 dim, side scatter low blasts from diagnosis (blue histograms), relapse (orange histogram), and isotype control (grey histogram). X axes show fluorescent intensity on a log scale, Y axes are percent events normalized to the modes of each sample. Negative controls represent fluorescence-minus-one controls.
Figure 10:
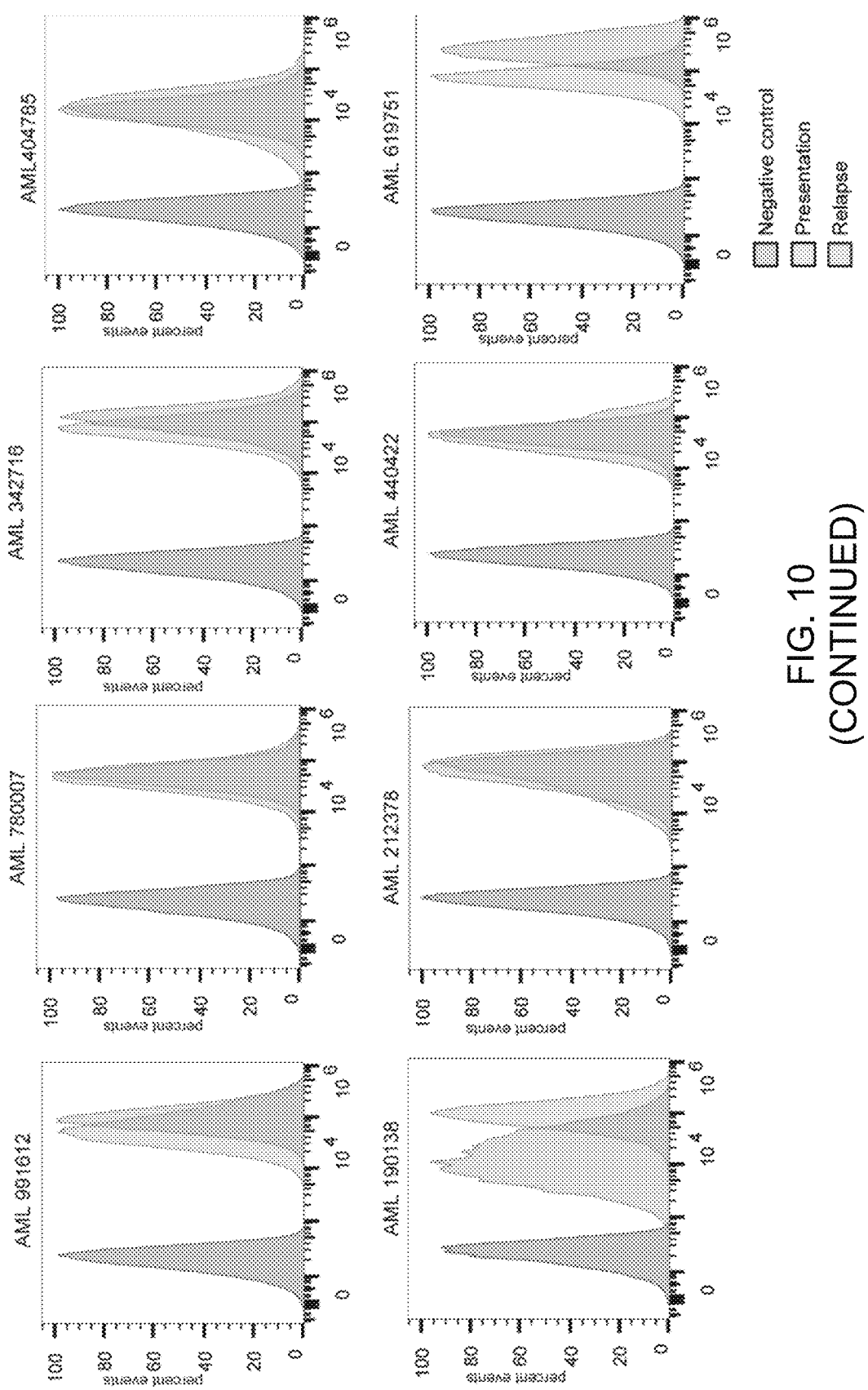

RNA expression of MHC class I genes was decreased in some relapse samples, but the changes were not significant (see e.g., FIG. 8A-FIG. 8B). No consistent changes in the expression of MHC class I proteins were detected on flow cytometry of AML cells (see e.g., FIG. 2A and FIG. 10). Furthermore, other genes that have been proposed to have a role in immune tolerance in cancer (PDL1, PDL2, and IDO1) had low or no detectable expression in AML cells, a finding that suggests that these genes are either not important for relapse after transplantation or not regulated at a transcriptional level (see e.g., FIG. 8A and Christopher et al. (2018) Immune Escape of Relapsed AML Cells after Allogeneic Transplantation N Engl J Med 379; 24 2330-2341, incorporated herein by reference).

Validation of Downregulation of MHC Class II

To determine the prevalence of downregulation of MHC class II in a larger group of patients with relapse of AML after transplantation, additional patients with samples in a tissue repository were identified for whom cryopreserved paired presentation and relapse samples were available. Samples for 10 additional patients with a post-transplantation relapse were identified and analyzed with flow cytometry, yielding a total of 16 patients with a post-transplantation relapse (including the original patients). All the presentation samples showed high expression of MHC class II proteins, a finding that is consistent with results that have been reported previously (see e.g., FIG. 9A-FIG. 9B). In 5 of the 16 post-transplantation relapse samples, MHC class II protein levels were at least 60 times lower than the levels seen in the paired presentation samples (as measured by the decrease in mean fluorescence intensity); the decreased levels were similar to the levels seen in negative controls. An additional 3 relapse samples had MHC class II protein levels that were 4 to 22 times lower than the levels seen at presentation, yielding a total of 8 patients with downregulation of MHC class II proteins on flow cytometry (see e.g., FIG. 9A).

Figure 11B:
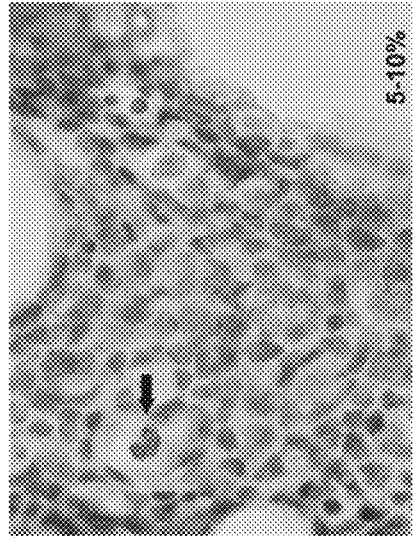
Figure 11B:
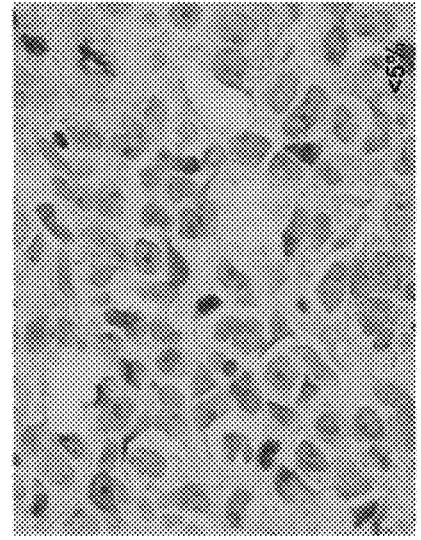
Figure 11B:
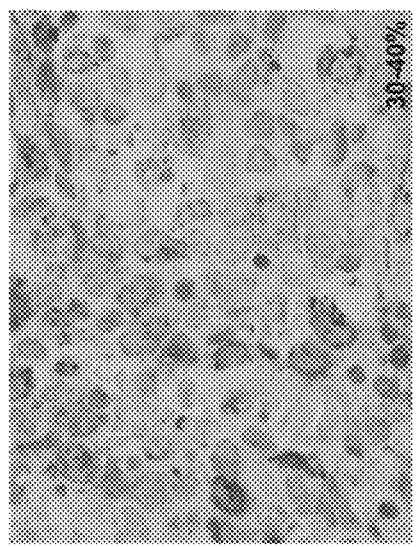
Figure 11B:
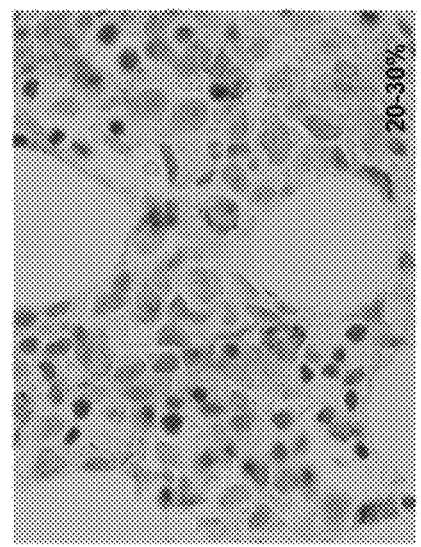
Figure 12:
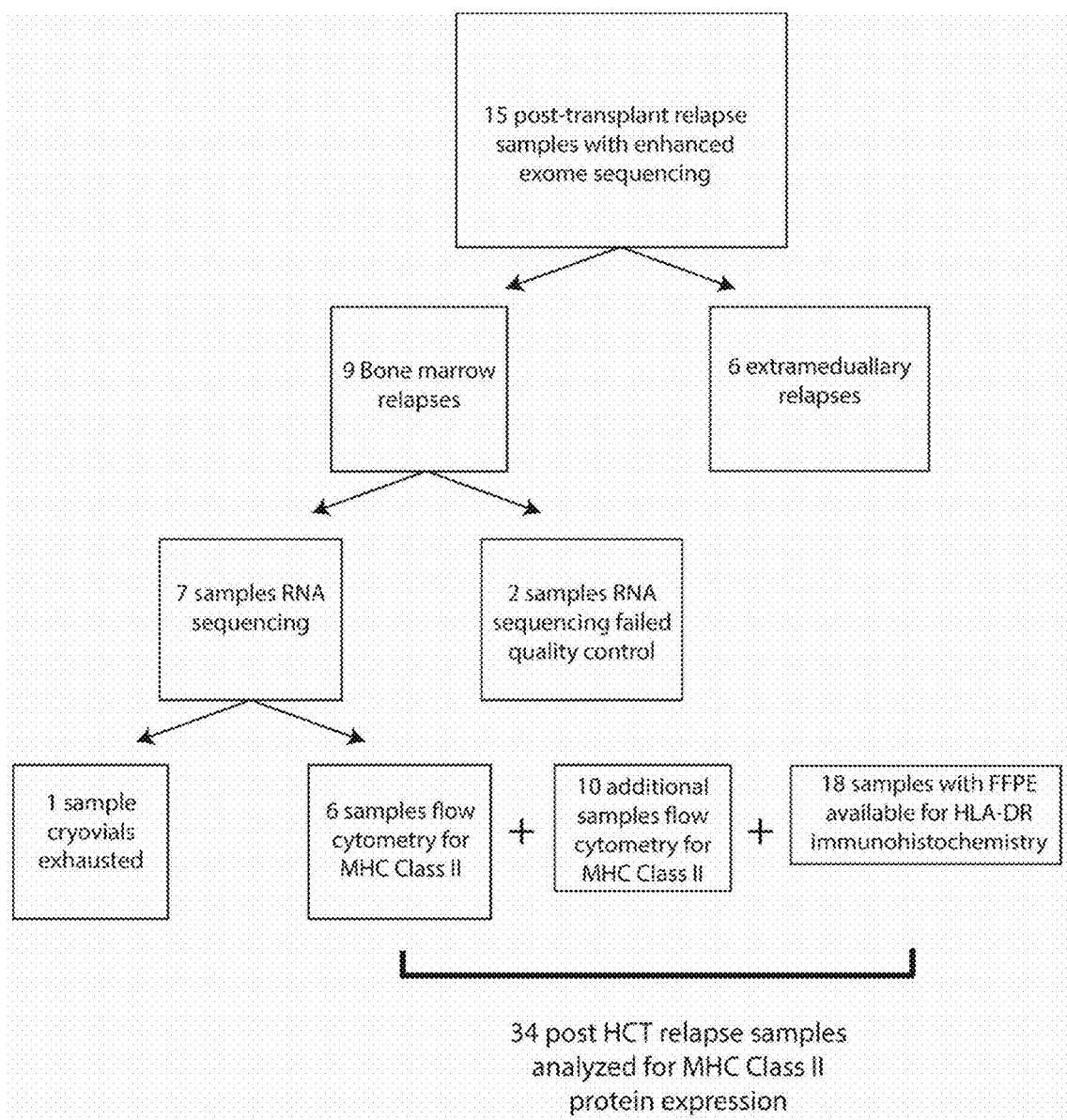
FIG. 12 is a flow chart showing samples analyzed for MHC class II expression. 15 samples were analyzed by enhanced exome sequencing. Of these, 9 samples had bone marrow relapses with available cryovials for RNA sequencing analysis. 2 of these failed quality control (QC) measures and the remaining 7 were analyzed for differential gene expression analysis, revealing downregulation of MHC class II genes. To validate these findings, 6 samples were analyzed by flow cytometry. An additional 10 post-transplant cases with presentation and relapse samples were analyzed by flow cytometry for MHC class II. Finally, 18 samples were identified with formalin-fixed paraffin-embedded (FFPE) bone marrow cores from post-transplant relapses and HLA-DR immunohistochemistry was performed on these.

To further extend these findings, immunohistochemical analysis was used to identify HLA-DR-positive myeloblasts in archived formalin-fixed, paraffin-embedded core samples of bone marrow from patients who were treated at the institution. Of 18 patients who had HLA-DR-positive blasts, 9 had markedly decreased expression of HLA-DR at relapse after transplantation (see e.g., FIG. 11A-FIG. 11B). Therefore, when these 9 patients were combined with the 8 patients with decreased expression of MHC class II proteins on flow cytometry, a total of 17 out of 34 evaluated patients with a post-transplantation relapse had evidence of downregulation of MHC class II on either flow cytometry or immunohistochemical analysis (see e.g., FIG. 12). There was no correlation between the downregulation of MHC class II and donor type or the use of immunosuppression at the time of relapse (see e.g., Christopher et al. (2018) Immune Escape of Relapsed AML Cells after Allogeneic Transplantation N Engl J Med 379; 24 2330-2341, incorporated herein by reference).

Functional Characterization of AML Blasts

Figure 2B:
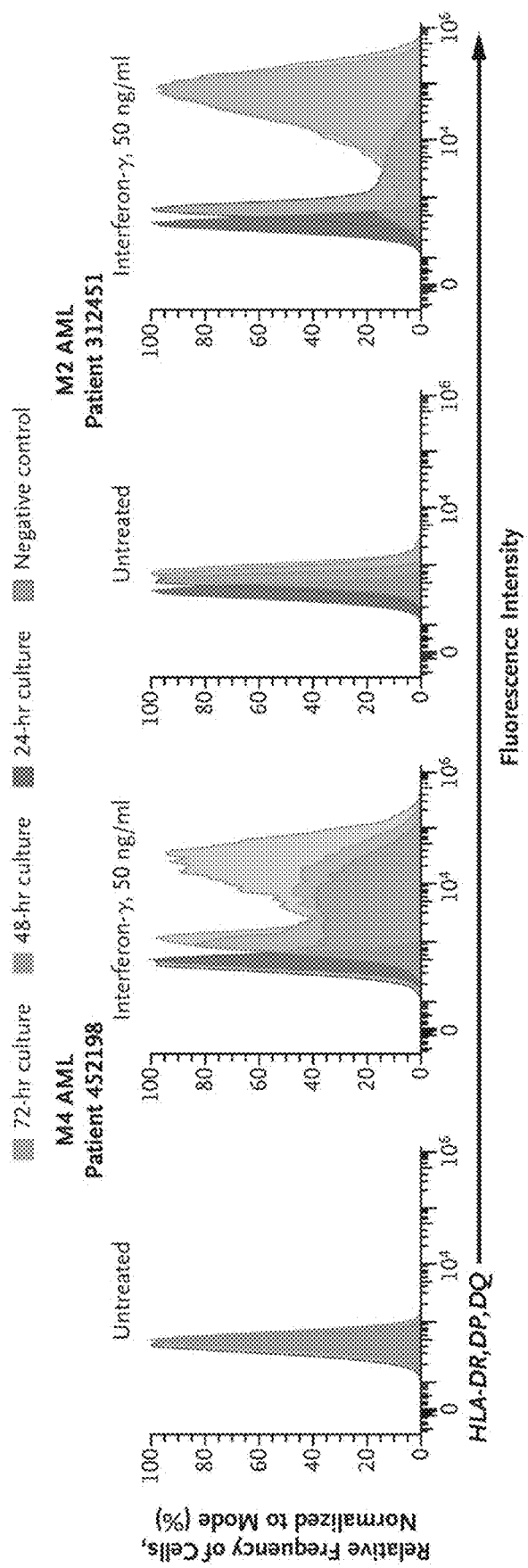

Interferon-γ (IFN-γ) has long been known to upregulate MHC class II on a variety of cell types, including myeloid cells. To determine whether the downregulation of MHC class II genes at relapse was reversible, interferon-γ was used to treat three cryopreserved relapse samples from patients with a post-transplantation relapse associated with complete downregulation of MHC class II proteins on flow cytometry (Patients 452198, 312451, and 142074). Culture of these cells with interferon-γ rapidly induced MHC class II protein expression on leukemic blasts, with essentially full restoration of MHC class II protein expression in nearly all AML blasts after 72 hours (see e.g., FIG. 2B and FIG. 13). The reversibility of downregulation of MHC class II in these blasts strongly suggests that this phenomenon is mediated by an epigenetic mechanism.

Figure 3A:
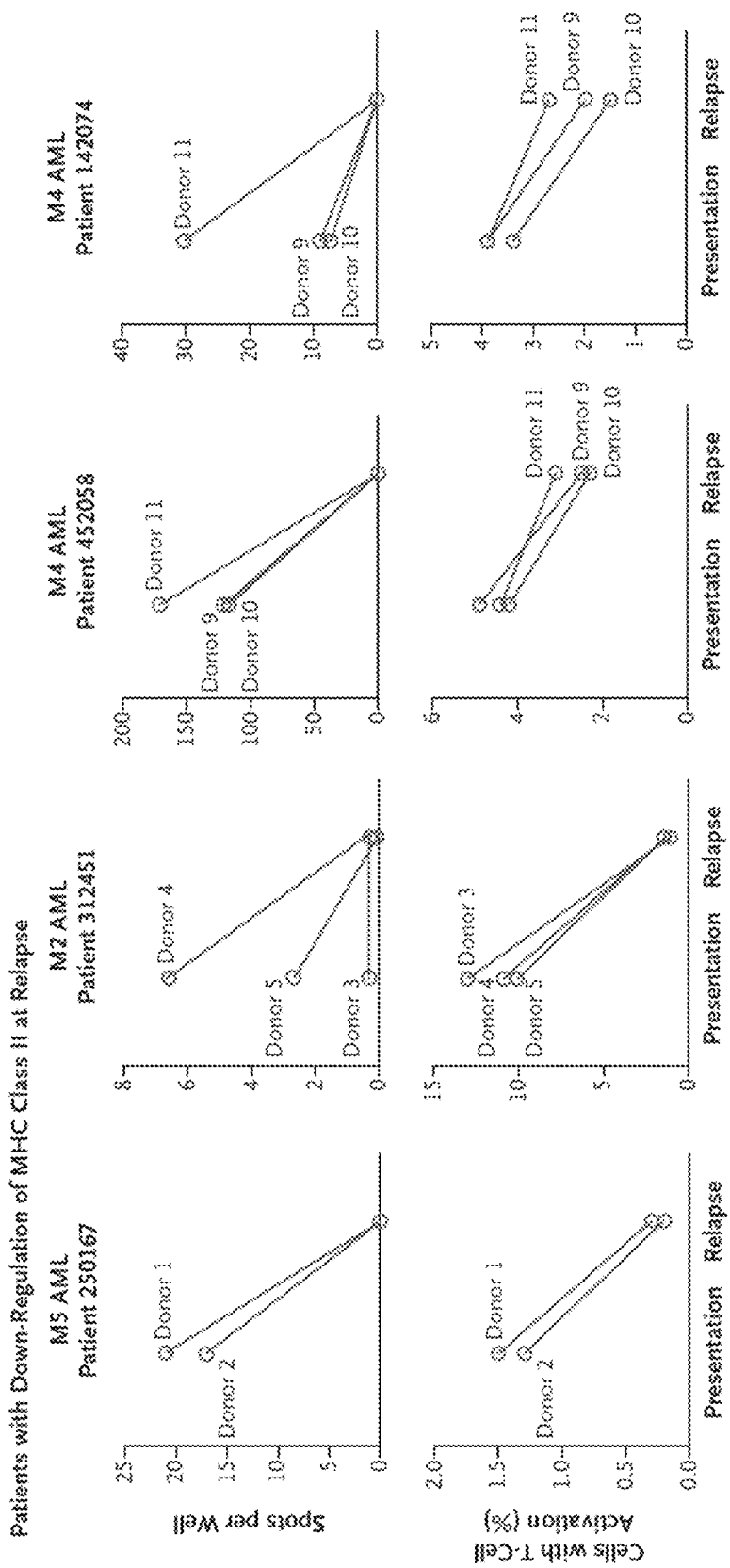
FIG. 3A-FIG. 3B is a series of graphs showing in vitro CD4+ T cell activation induced by AML cells from patients with a relapse after transplantation. Cryopreserved presentation and relapse samples from (A) patients with a post-transplantation relapse who had downregulation of MHC class II at relapse or (B) did not have downregulation of MHC class II at relapse were incubated with HLA-mismatched third-party donor CD4+ T cells for 4 days. CD4+ T cells from two or three separate donors were used for each assay. Activation of CD4+ T cells was measured with an interferon-γ enzyme-linked immunospot assay (top row in each panel) or with flow cytometry for activation markers CD137 and CD279 (bottom row in each panel). (A) Relapse samples from patients who had downregulation of MHC class II caused minimal stimulation of third-party CD4+ T cells, whereas paired presentation samples stimulated third-party CD4+ T cells effectively. (B) In contrast, paired presentation and relapse samples from patients who did not have downregulation of MHC class II stimulated CD4+ T cells equivalently. For each patient, the French-American-British classification of AML is shown; a classification of M0 AML indicates AML with minimal differentiation, M1 AML indicates AML with minimal maturation, M2 AML indicates AML with maturation, M4 AML indicates acute myelomonocytic leukemia, and M5 AML indicates acute monoblastic leukemia.
Figure 3B:
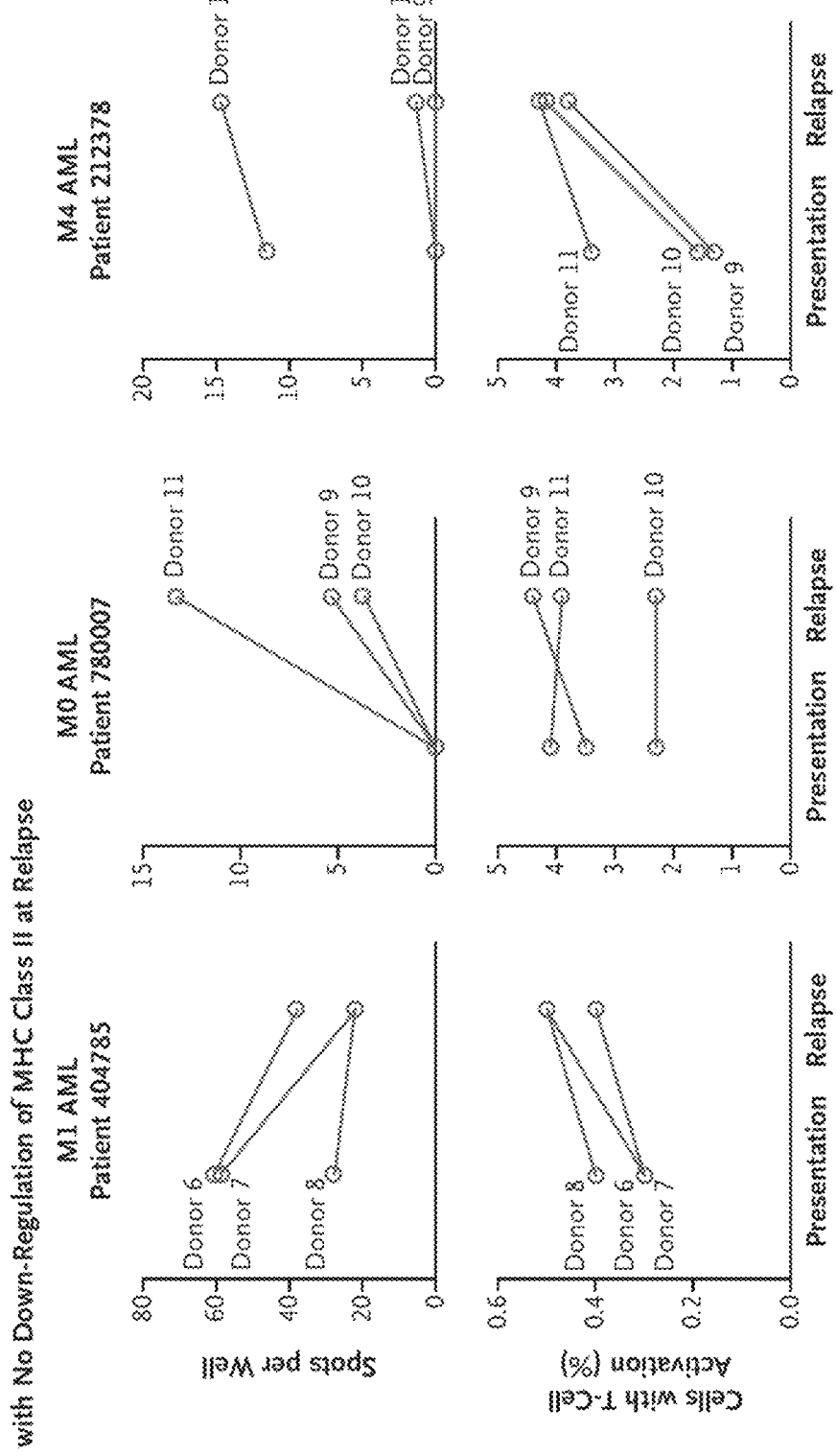

To test the capacity of presentation and relapse samples of AML cells to stimulate an immune response from allogeneic T cells, cryopreserved AML cells from seven patients were cocultured with purified CD4+ T cells from HLA-mismatched third-party donors. As expected, the presentation samples (all of which had high expression of MHC class II genes) activated a subset of allogeneic CD4+ T cells, as measured by interferon-γ production and co-expression of activation markers CD137 and CD279 (see e.g., FIG. 3A-FIG. 3B). In contrast, the post-transplantation relapse samples that had decreased expression of MHC class II proteins had a significantly diminished capacity to stimulate third-party CD4+ T cells (see e.g., FIG. 3A-FIG. 3B).

Analysis of Expression of Immune-Related Genes with Single-Cell RNA Sequencing

Figure 4A:
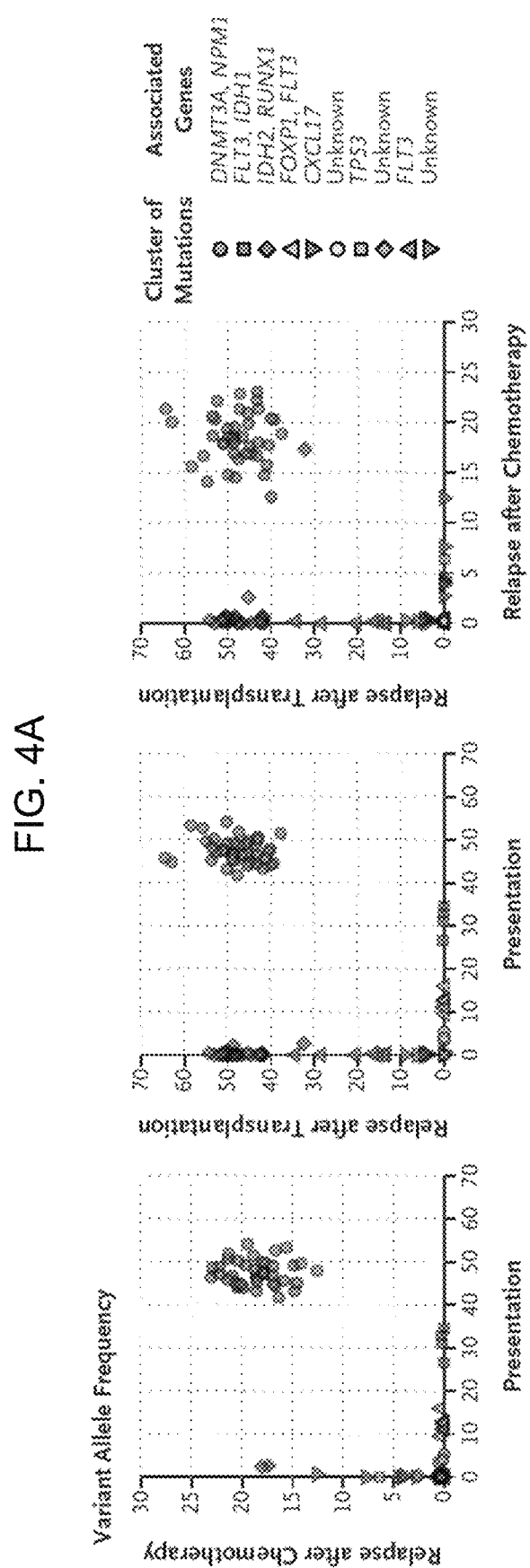
Figure 4B:
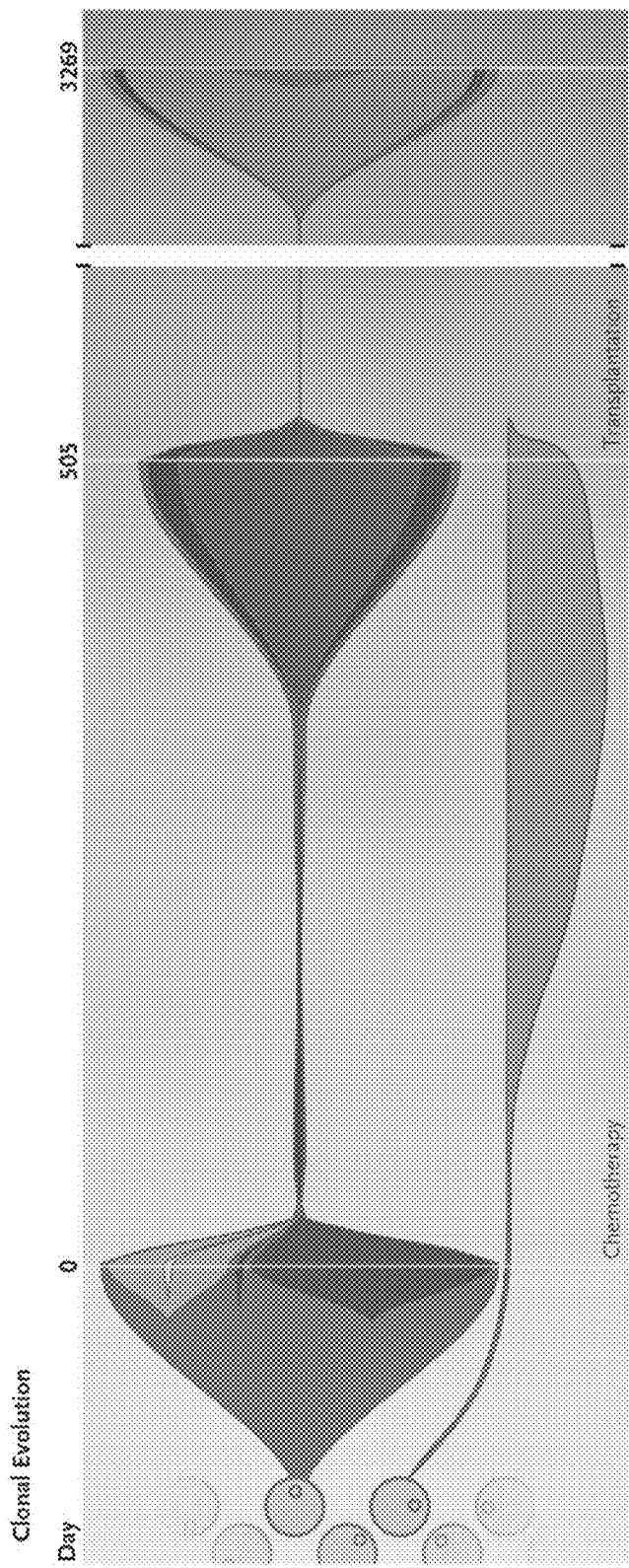
Figures 4C, 4D, 4E:
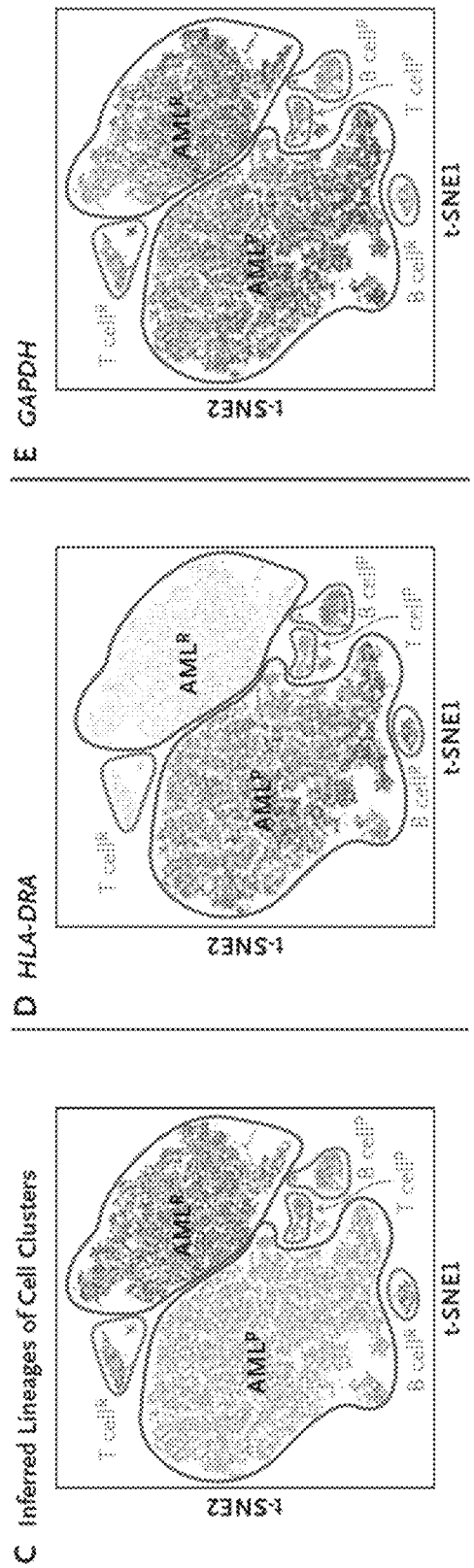

To better characterize the expression of immune-related genes in individual AML cells, single-cell RNA sequencing was performed on bone marrow samples obtained at initial presentation and at post-transplantation relapse from Patient 452198 (a patient known in previous studies as AML31), who had post-chemotherapy and post-transplantation relapses. Both samples were composed of more than 95% monoblasts (indicating a French-American-British classification of M5 AML). The clonal evolution of AML at post-chemotherapy relapse and at post-transplantation relapse is shown in FIG. 4A-FIG. 4B. The post-chemotherapy relapse arose from a small subclone that was detected at presentation. This same subclone, which contained mutations in IDH2 and RUNX1, evolved further into the post-transplantation relapse, but no new AML-specific driver mutations were present at that time and no structural variants were identified on whole-genome sequencing (see e.g., FIG. 4A-FIG. 4B, FIG. 6, and Christopher et al. (2018) Immune Escape of Relapsed AML Cells after Allogeneic Transplantation N Engl J Med 379; 24 2330-2341, incorporated herein by reference).

In FIG. 4C-FIG. 4G, data from single-cell RNA sequencing are shown, with all the cells from the presentation and post-transplantation relapse bone marrow samples plotted together with t-distributed stochastic neighbor embedding (t-SNE), a graph layout algorithm that places cells with similar expression profiles near one another. In this schema, there are two large cell clusters—each with a distinct expression profile—that correspond to AML cells from the presentation and post-transplantation relapse samples (see e.g., FIG. 4C); small clusters with expression profiles consistent with B cells and T cells were also detected in both samples. Expression of HLA-DRA (and the other MHC class II genes) was high in most of the AML cells at presentation but was virtually undetectable in all the cells at relapse (see e.g., FIG. 4D), a finding consistent with the results of bulk RNA sequencing. At presentation, a distinct cluster of HLA-DRA$^{low}$ cells was not detected, which could have represented a preexisting subclone with low MHC class II gene expression.

Given the clinical interest in the use of checkpoint inhibitors to restore graft-versus-leukemia activity after transplantation, T-cell exhaustion after relapse was also studied in this patient. There was no detectable expression of ICOS or PD1 in the T-cell population at relapse (see e.g., FIG. 4F and FIG. 4G), even though expression of these genes was detected in a subset of T cells in normal bone marrow (see e.g., FIG. 14A-FIG. 14F). Expression of the gene encoding the T cell activation marker granzyme A (GZMA) was detected in many T cells at presentation and at relapse (see e.g., FIG. 4H); the genes encoding activation markers granzyme B and CCL5 were also expressed in those T cells. This combination of findings suggests that, in this patient, relapse may have been driven by rare AML cells that randomly developed a loss of MHC class II gene expression by means of an epigenetic mechanism. These cells were strongly selected for and contributed to relapse because they escaped the immune surveillance exerted by the graft-versus-leukemia effect.

Exon Sequencing of Extramedullary Relapse

Extramedullary relapse occurs more commonly after hematopoietic stem cell transplant than after chemotherapy or at presentation. This may be due in part to differences in immune surveillance in extramedullary sites, and in fact has been associated with deletion of genes encoding MHC class I. It is presently thought that extramedullary relapse of AML may be associated with mutations involving genes important for immune surveillance or AML cell trafficking. 136 somatic mutations were observed in 6 cases of extramedullary relapse. None occurred in more than a single case and none were in genes that had known immune function, including MHC class I or class II genes (see e.g., FIG. 5). An analysis of the pathways of genes with mutations in extramedullary relapse and bone marrow relapse was performed, and no significant enrichment for cell adhesion or trafficking pathways was observed. Given the small sample, however, it should not be ruled out that the observed mutations may contribute to extramedullary relapse through unknown mechanisms.

Analysis of Putative Neoantigens

Figure 15:
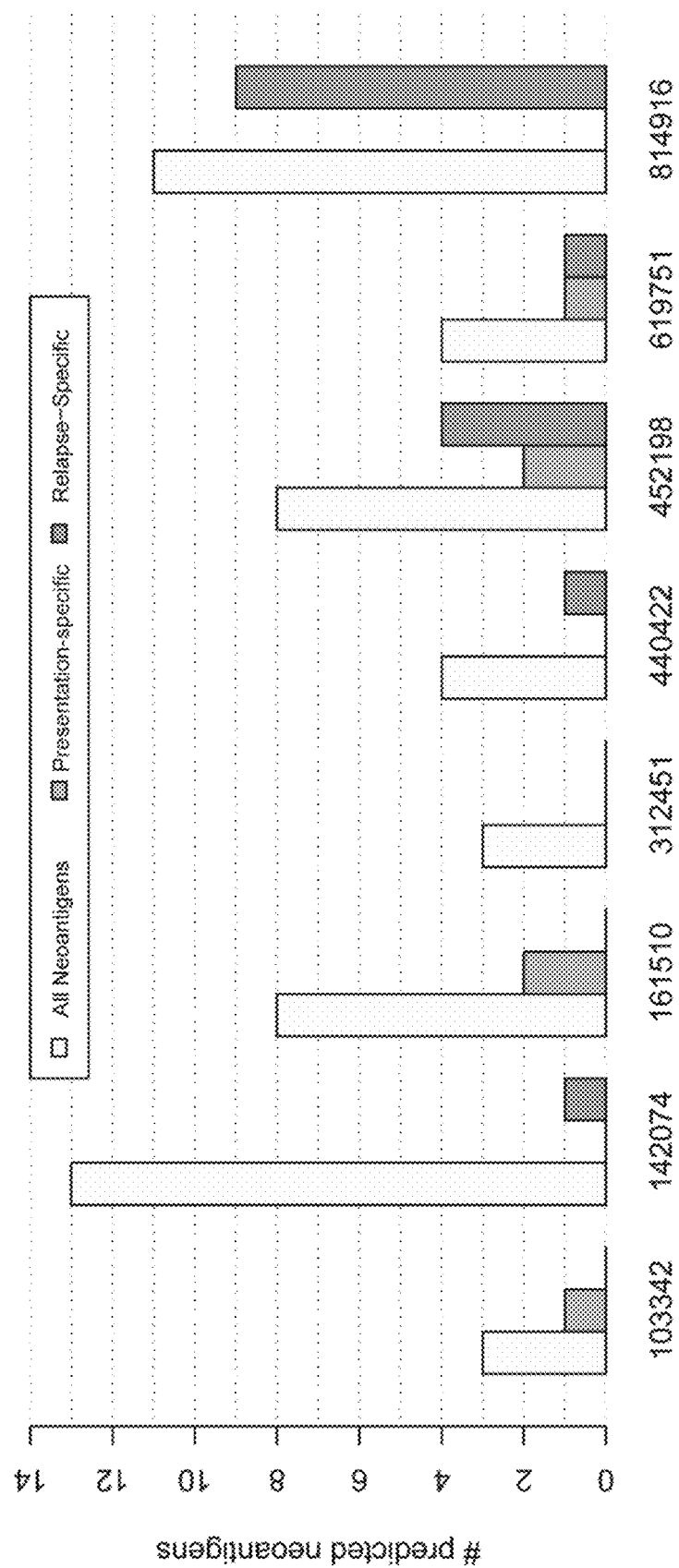
FIG. 15 is a graph showing bioinformatic analysis of putative neoantigens at presentation and relapse. Expressed variants that were detected by exome sequencing in each sample were determined bioinformatically as likely to be presented by MHC class I molecules on AML cells at presentation, relapse, or both. Few potential neoantigens identified in this way from presentation samples were cleared at relapse (orange bars).

Loss of cancer-associated neoantigens has also been proposed as a mechanism of immune escape. Using a previously published bioinformatic approach, potential neoantigens in presentation and relapse samples from patients whose HLA typing was available were identified (n=8 patients). An average of 6.6 possible neoantigens were identified per sample (range 3-13), most of which were present in both presentation and relapse samples. Four patients had possible neoantigens that were cleared at relapse (mean 1.5 per case, range 1-2, see e.g., FIG. 15 and Christopher et al. (2018) Immune Escape of Relapsed AML Cells after Allogeneic Transplantation N Engl J Med 379; 24 2330-2341 for a list of bioinformatically predicted neoepitopes present at presentation, relapse, or both in 8 cases, incorporated herein by reference), significantly fewer than have been reported for solid tumors.

Whether the clearance of these particular variants contributed to relapse in these cases will require further study.

CIITA Downregulation and Promoter Methylation

The coordinate downregulation of MHC class II gene RNA in post-transplant relapse cases raised the possibility they may be regulated by a single master regulatory gene or pathway. A potential candidate is CIITA, a transcriptional transactivator that has long been known to play a key role in activating the expression of MHC class II genes. Expression of CIITA was decreased in 4/6 cases with decreased MHC class II expression (see e.g., FIG. 1A-FIG. 1F). In this subset of cases, CIITA expression correlated with MHC class II expression, raising the possibility that in some instances, MHC class II downregulation may be mediated via CIITA downregulation (see e.g., FIG. 16C). CIITA is not known to affect the expression of many of the other genes that were dysregulated in post-transplant relapses, so other mechanisms are likely relevant for many of these events.

Since CIITA silencing has been associated with increased methylation of its promoter region, whole genome bisulfite sequencing was performed on presentation and relapse samples from 3 post-transplant and 3 post-chemotherapy relapse samples (both the post-chemotherapy and post-transplant relapses were evaluated in one patient). Two of the three post-transplant relapse samples had decreased MHC class II expression and the remaining samples had similar expression at presentation as at relapse. Although 1196 differentially methylated regions were identified when comparing the presentation and relapse samples (see e.g., Christopher et al. (2018) Immune Escape of Relapsed AML Cells after Allogeneic Transplantation N Engl J Med 379; 24 2330-2341 for a table showing differentially methylated regions discovered from whole genome bisulfite sequencing performed on 3 post-chemotherapy and 3 post-transplant relapse cases, incorporated herein by reference), virtually none were consistently dysregulated and unique to the post-transplant setting.

No MHC class II gene loci were among these regions, and there was no correlation between DNA methylation at MHC class II gene loci and MHC class II mRNA expression.

Figure 16A:
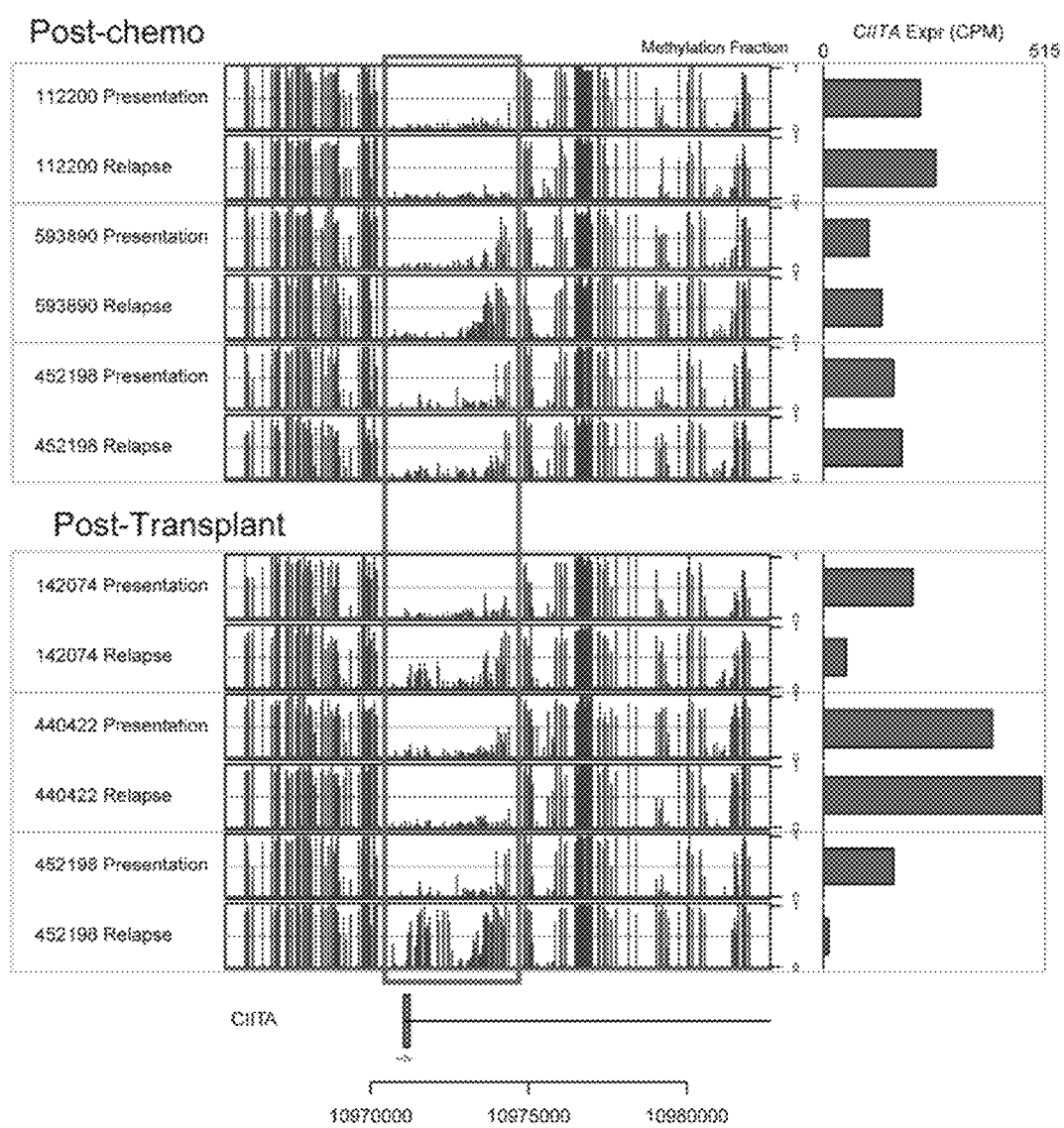
FIG. 16A-FIG. 16C is a series of graphs showing DNA methylation of the CIITA promotor region in AML samples.
Figure 16B:
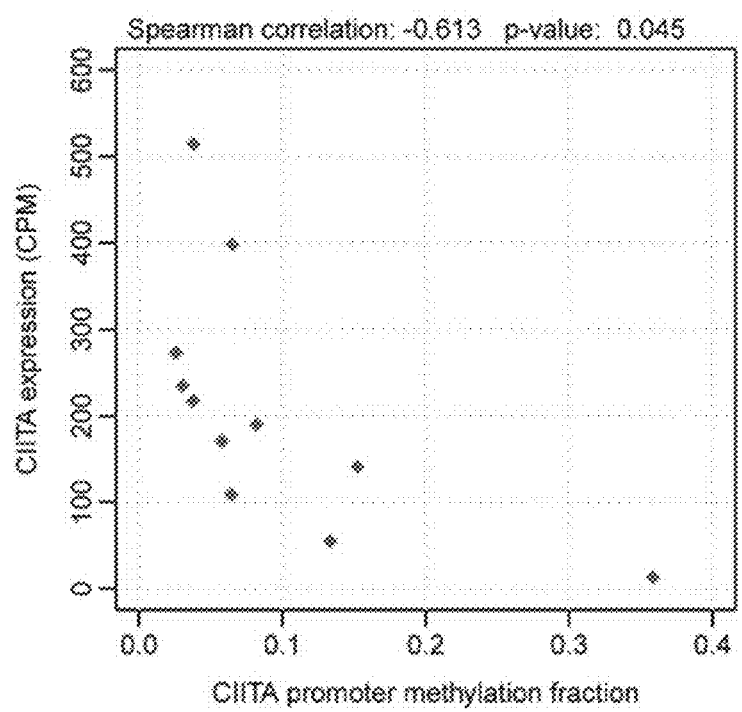
Figure 16C:
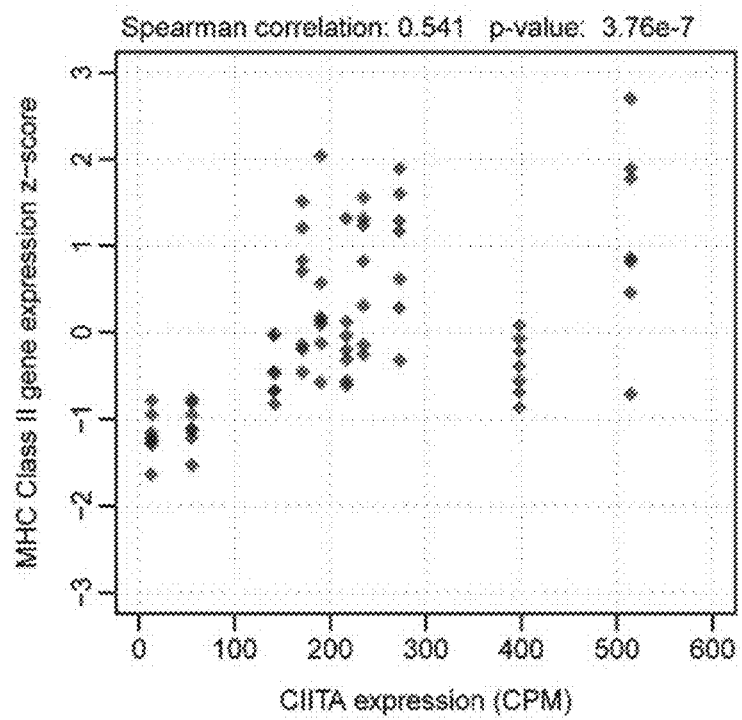

However, increased DNA methylation was observed in the region of the CIITA promotor/intron 1 in the two post-transplant samples with decreased CIITA (and MHC class II) expression (cases 142074 and 452198), but not the samples with unchanged MHC class II mRNA expression (see e.g., FIG. 16A). While preliminary, these data raise the possibility that in some cases, decreased CIITA expression and subsequent downregulation of MHC class II genes may be related to increased methylation of the CIITA promotor/intron 1 region.

In Vivo Validation of IFN-γ Treatment-Induced MHC Class II Expression

IFN-γ treatment of mice engrafted with human AML cells induces MHC class II expression. Here, it was shown that in vivo treatment with interferon gamma (IFN-γ) induces MHC class II expression on MHC class II low AML cells. Immunodeficient mice were engrafted with primary AML cells from a patient with low MHC class II expression at relapse after hematopoietic stem cell transplantation. After engraftment, mice were treated with IFN-γ 10 µg per dose, three doses weekly x two weeks (see e.g., FIG. 17A-FIG. 17B).

Discussion

Since the graft-versus-leukemia effect contributes to the therapeutic benefit of allogeneic hematopoietic stem-cell transplantation in patients with AML, it is presently thought that relapse of AML after transplantation might be driven by genetic changes that influence immune function. In this small sample, mutations in known immune regulatory genes were uncommon in post-transplantation relapses, a finding consistent with the idea that such changes are not a common cause of relapse.

To determine whether post-transplantation relapse was associated with recurrent epigenetic changes, an analysis of all genes with detectable RNA expression was performed in paired samples obtained at initial presentation and at post-transplantation relapse, and it was found that a large proportion of the 221 differentially expressed genes were classified as having a known or likely role in immune function. Downregulated genes included the classical MHC class II genes, a result that confirmed findings described previously in three of six patients who had a relapse of chronic myeloid leukemia or AML after transplantation. Because a decrease in antigen presentation could plausibly contribute to escape from the graft-versus-leukemia effect, measuring MHC class II expression in additional patients was performed (even though it is currently unclear whether a change in this expression contributes causally to relapse). Using flow cytometry and immunohistochemical analysis, decreased expression of MHC class II proteins was detected in post-transplantation relapse samples from a total of 17 of 34 patients. The four tested post-transplantation relapse samples with decreased expression of MHC class II did not stimulate third-party CD4+ T cells in vitro. Although in vivo evidence shown here indicates that the administration of IFN-γ resulted in upregulated MHC class II expression, further research will be performed to determine whether this phenomenon is sufficient to mediate AML relapse in vivo.

The reversibility of downregulation of MHC class II by interferon-γ suggests that this event is epigenetic in nature. Single-cell RNA sequencing in one patient (Patient 452198) revealed high expression of MHC class II genes in the vast majority of AML cells at presentation. This finding suggests that immunologically resistant AML cells were rare or absent at presentation; furthermore, there was no evidence of a subclone with low MHC class II gene expression. Selection of these cells presumably occurred after the transplanted immune cells exerted selective pressure against AML cells that could be recognized immunologically. This process has been described as immunoediting in solid tumors, in which tumor clones evolve in response to immune-mediated selective pressure and ultimately escape, leading to relapse. Although the use of immunosuppression after transplantation could potentially contribute to downregulation of MHC class II, a significant correlation between loss of MHC class II expression and use of graft-versus-host disease prophylaxis at the time of relapse was not observed (see e.g., Christopher et al. (2018) Immune Escape of Relapsed AML Cells after Allogeneic Transplantation N Engl J Med 379; 24 2330-2341, incorporated herein by reference).

In conclusion, this study showed that AML cells that escaped the immune surveillance provided by allogeneic T cells after allogeneic hematopoietic stem-cell transplantation frequently had dysregulation of a number of pathways that regulate immune function. These changes appeared to be epigenetic in nature in at least some cases, which suggests that therapeutic strategies to re-sensitize AML cells to the graft-versus-leukemia effect may be feasible. This study also showed that, in vitro and in vivo administration of IFN-γ resulted in upregulation of MHC class II expression in AML cells.

What is claimed is:

1. A method of upregulating an MHC class II gene of a hematological cancer cell in a subject having a hematological cancer, the method comprising administering IFN-γ to the subject, wherein the administering occurs following a post-transplantation relapse associated with downregulation of the MHC class II gene in the hematological cancer cell, and wherein the post-transplantation relapse is a relapse after a hematopoietic stem cell transplant (HCT) comprising donor T cells to the subject.

2. The method of claim 1, wherein the administering IFN-γ results in:
increasing or restoring sensitivity of the hematological cancer cell to immune attack from an immune cell;
sensitizing the hematological cancer cell to graft-versus-leukemia effect;
stimulating an immune response from the donor T cells;
restoring the ability of the hematological cancer cell to stimulate the donor T cells; or
restoring recognition of an antigen of the hematological cancer cell by the donor T cells.

3. The method of claim 2, wherein the immune cell is an allogenic or donor immune cell.

4. The method of claim 2, wherein the immune cell is an allogenic CD4+ T cell.

5. The method of claim 1, wherein the post-transplantation relapse is a relapse after receiving a hematopoietic stem cell transplant (HCT) and at least one of chemotherapy, immunotherapy, or radiation.

6. The method of claim 1, wherein the hematological cancer is acute myeloid leukemia (AML).

7. The method of claim 1, wherein the hematological cancer cell has reduced MHC class II expression compared to a control or fails to stimulate an immune response from T cells.

8. The method of claim 1, wherein the hematological cancer cell has a downregulated MHC class II gene selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

9. The method of claim 1, wherein the MHC class II gene is selected from the group consisting of: HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, CIITA, and combinations thereof.

* * * * *